US009528918B2

(12) United States Patent
Reinhardt et al.

(10) Patent No.: US 9,528,918 B2
(45) Date of Patent: Dec. 27, 2016

(54) AUTOMATED HIGH VOLUME SLIDE PROCESSING SYSTEM

(71) Applicant: Ventana Medical Systems, Inc., Tucson, AZ (US)

(72) Inventors: Kurt Reinhardt, Tucson, AZ (US); Charles D. Lemme, Tucson, AZ (US); Glen Ward, Tucson, AZ (US); William L. Richards, Tucson, AZ (US); Wayne Showalter, Tucson, AZ (US); Brandon Ambler, Tucson, AZ (US); Austin Micheil Ashby, Tucson, AZ (US); Chris Borchert, Tucson, AZ (US); Devon C. Campbell, Oro Valley, AZ (US); Kimberly Christensen, Tucson, AZ (US); Matthew Freeman, Tucson, AZ (US); Andrew Ghusson, Tucson, AZ (US); Rick Griebel, Tucson, AZ (US); Kendall B. Hendrick, Tucson, AZ (US); Miroslav Holubec, Tucson, AZ (US); Parula Mehta, Oro Valley, AZ (US); Vince Rizzo, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 21 days.

(21) Appl. No.: 14/082,092

(22) Filed: Nov. 15, 2013

(65) Prior Publication Data
US 2014/0178858 A1    Jun. 26, 2014

Related U.S. Application Data

(60) Continuation of application No. 11/181,625, filed on Jul. 13, 2005, now Pat. No. 8,663,991, which is a
(Continued)

(51) Int. Cl.
G01N 1/30 (2006.01)
B01L 9/00 (2006.01)
(Continued)

(52) U.S. Cl.
CPC . *G01N 1/30* (2013.01); *B01L 9/52* (2013.01); *G01N 1/312* (2013.01); *G01N 1/36* (2013.01);
(Continued)

(58) Field of Classification Search
None
See application file for complete search history.

(56) References Cited

U.S. PATENT DOCUMENTS 3,219,416 A    11/1965 Natelson
3,574,064 A    4/1971 Binnings et al.
(Continued)

FOREIGN PATENT DOCUMENTS

AU    2005203557    8/2006
AU    2003224987    9/2009
(Continued)

OTHER PUBLICATIONS

"Coverslips and Stainers," Hacker Instruments and Industries, Inc., 3 pages, [retrieved on Apr. 18, 2001]. Retrieved from the Internet <URL:http://hackerinstruments.com/coverslippers.htm>.
(Continued)

*Primary Examiner* — Brian R Gordon
(74) *Attorney, Agent, or Firm* — Perkins Coie LLP

(57) ABSTRACT

An automated system is provided for performing slide processing operations on slides bearing biological samples. In one embodiment, the disclosed system includes a slide tray holding a plurality of slides in a substantially horizontal position and a workstation that receives the slide tray. In a particular embodiment, a workstation delivers a reagent to slide surfaces without substantial transfer of reagent (and
(Continued)

reagent borne contaminants such as dislodged cells) from one slide to another. A method for automated processing of slides also is provided.

36 Claims, 35 Drawing Sheets

Related U.S. Application Data division of application No. 11/116,676, filed on Apr. 27, 2005, now Pat. No. 7,468,161, which is a continuation-in-part of application No. 10/414,804, filed on Apr. 15, 2003, now Pat. No. 7,303,725.

(60) Provisional application No. 60/372,506, filed on Apr. 15, 2002.

(51) Int. Cl.
  *G01N 1/31* (2006.01)
  *G01N 1/36* (2006.01)
  *G01N 35/00* (2006.01)

(52) U.S. Cl.
  CPC .. *B01L 2300/0822* (2013.01); *G01N 35/00732* (2013.01); *Y10T 436/11* (2015.01); *Y10T 436/112499* (2015.01); *Y10T 436/25* (2015.01); *Y10T 436/2575* (2015.01)

(56) References Cited

U.S. PATENT DOCUMENTS

| | | | |
|---|---|---|---|
| 3,650,437 A | 3/1972 | Binnings et al. |
| 3,665,148 A | 5/1972 | Yasenchak et al. |
| 3,695,281 A | 10/1972 | Leon |
| 3,853,092 A | 12/1974 | Amos et al. |
| 3,854,703 A | 12/1974 | Gibbs et al. |
| 3,979,576 A | 9/1976 | Janson |
| 4,013,038 A | 3/1977 | Rogers et al. |
| 4,043,292 A | 8/1977 | Rogers et al. |
| 4,058,367 A | 11/1977 | Gilford |
| 4,092,952 A | 6/1978 | Wilkie et al. |
| 4,245,967 A | 1/1981 | Busselet |
| RE30,730 E | 9/1981 | Duff |
| 4,286,637 A | 9/1981 | Wilson |
| 4,298,571 A | 11/1981 | DiFulvio et al. |
| 4,346,056 A | 8/1982 | Sakurada |
| 4,358,470 A | 11/1982 | Rasmussen |
| 4,384,193 A | 5/1983 | Kledzik et al. |
| 4,406,547 A | 9/1983 | Aihara |
| 4,430,299 A | 2/1984 | Horne |
| 4,447,395 A | 5/1984 | Englar et al. |
| 4,453,807 A | 6/1984 | Faulkner et al. |
| 4,455,280 A | 6/1984 | Shinohara et al. |
| 4,484,293 A | 11/1984 | Minucciani et al. |
| 4,528,159 A | 7/1985 | Liston |
| 4,539,855 A | 9/1985 | Jacobs |
| 4,543,236 A | 9/1985 | Von Gise |
| 4,577,514 A | 3/1986 | Bradley et al. |
| 4,584,275 A | 4/1986 | Okano et al. |
| 4,629,862 A | 12/1986 | Kitagawa et al. |
| 4,643,879 A | 2/1987 | Hanaway |
| 4,647,431 A | 3/1987 | Sekine et al. |
| 4,648,023 A | 3/1987 | Powell |
| 4,659,971 A | 4/1987 | Suzuki et al. |
| 4,670,974 A | 6/1987 | Antoszewksi et al. |
| 4,676,951 A | 6/1987 | Armes et al. |
| 4,678,752 A | 7/1987 | Thorne et al. |
| 4,681,741 A | 7/1987 | Hanaway |
| 4,695,430 A | 9/1987 | Coville et al. |
| 4,708,886 A | 11/1987 | Nelson |
| 4,720,463 A | 1/1988 | Farber et al. |
| 4,727,409 A | 2/1988 | Conner et al. |
| 4,727,494 A | 2/1988 | Boute |
| 4,729,661 A | 3/1988 | Bell |
| 4,731,335 A | 3/1988 | Brigati |
| 4,731,355 A | 3/1988 | Iwasaki et al. |
| 4,738,824 A | 4/1988 | Takeuchi |
| 4,764,342 A | 8/1988 | Kelln et al. |
| 4,774,055 A | 9/1988 | Wakatake et al. |
| 4,777,020 A | 10/1988 | Brigati |
| 4,781,891 A | 11/1988 | Galle et al. |
| 4,795,710 A | 1/1989 | Muszak et al. |
| 4,798,706 A | 1/1989 | Brigati |
| 4,801,431 A | 1/1989 | Cuomo et al. |
| 4,805,469 A | 2/1989 | Commarmot |
| 4,807,152 A | 2/1989 | Lane et al. |
| 4,815,978 A | 3/1989 | Mazza et al. |
| 4,835,711 A | 5/1989 | Hutchins et al. |
| 4,837,159 A | 6/1989 | Yamada |
| 4,843,566 A | 6/1989 | Gordon et al. |
| 4,844,868 A | 7/1989 | Rokugawa |
| 4,847,208 A | 7/1989 | Bogen |
| 4,852,001 A | 7/1989 | Tsushima et al. |
| 4,855,109 A | 8/1989 | Muraishi et al. |
| 4,857,272 A | 8/1989 | Sugaya |
| 4,858,155 A | 8/1989 | Okawa et al. |
| 4,865,986 A | 9/1989 | Coy et al. |
| 4,895,706 A | 1/1990 | Root et al. |
| 4,896,269 A | 1/1990 | Tong |
| 4,902,481 A | 2/1990 | Clark et al. |
| 4,911,098 A | 3/1990 | Tabata |
| 4,911,915 A | 3/1990 | Fredenburgh |
| 4,919,887 A | 4/1990 | Wakatake |
| 4,928,540 A | 5/1990 | Kido et al. |
| 4,933,146 A | 6/1990 | Meyer et al. |
| 4,935,875 A | 6/1990 | Shah et al. |
| 4,961,906 A | 10/1990 | Andersen et al. |
| 4,964,544 A | 10/1990 | Hanna et al. |
| 4,965,049 A | 10/1990 | Lillig et al. |
| 4,971,913 A | 11/1990 | Manabe et al. |
| 4,975,250 A | 12/1990 | Mordecki |
| 4,979,093 A | 12/1990 | Laine et al. |
| 4,979,128 A | 12/1990 | Seki et al. |
| 4,985,206 A | 1/1991 | Bowman et al. |
| 5,002,736 A | 3/1991 | Babbitt et al. |
| 5,023,187 A | 6/1991 | Koebler et al. |
| 5,030,418 A | 7/1991 | Miyata |
| 5,035,866 A | 7/1991 | Wannlund |
| 5,040,123 A | 8/1991 | Barber et al. |
| 5,051,238 A | 9/1991 | Umetsu et al. |
| 5,073,504 A | 12/1991 | Bogen |
| 5,075,079 A | 12/1991 | Kerr et al. |
| 5,089,229 A | 2/1992 | Heidt et al. |
| 5,093,557 A | 3/1992 | Lok et al. |
| 5,096,670 A | 3/1992 | Harris et al. |
| 5,104,621 A | 4/1992 | Pfost et al. |
| 5,105,066 A | 4/1992 | Houdy et al. |
| 5,116,496 A | 5/1992 | Scott |
| 5,122,342 A | 6/1992 | McCulloch et al. |
| 5,122,959 A | 6/1992 | Nathanson et al. |
| 5,148,370 A | 9/1992 | Litt et al. |
| 5,154,889 A | 10/1992 | Muraishi |
| 5,168,453 A | 12/1992 | Nomaru et al. |
| 5,180,606 A | 1/1993 | Stokes et al. |
| 5,181,259 A | 1/1993 | Rorvig |
| 5,207,987 A | 5/1993 | Kureshy et al. |
| 5,209,903 A | 5/1993 | Kanamori et al. |
| 5,218,645 A | 6/1993 | Bacus |
| 5,229,074 A | 7/1993 | Heath et al. |
| 5,231,029 A | 7/1993 | Wootton et al. |
| 5,232,664 A | 8/1993 | Krawzak et al. |
| 5,232,665 A | 8/1993 | Burkovich et al. |
| 5,233,533 A | 8/1993 | Edstrom et al. |
| 5,246,665 A | 9/1993 | Tyranski et al. |
| 5,266,272 A | 11/1993 | Griner et al. |
| 5,273,905 A | 12/1993 | Muller et al. |
| 5,280,156 A | 1/1994 | Niori et al. |
| 5,282,149 A | 1/1994 | Grandone et al. |
| 5,304,347 A | 4/1994 | Mann et al. |
| 5,311,426 A | 5/1994 | Donohue et al. |
| 5,314,825 A | 5/1994 | Weyrauch et al. |
| 5,316,452 A | 5/1994 | Bogen et al. |

(56) References Cited

U.S. PATENT DOCUMENTS

| | | | |
|---|---|---|---|
| 5,316,726 A | 5/1994 | Babson et al. |
| 5,332,549 A | 7/1994 | MacIndoe, Jr. |
| 5,334,353 A | 8/1994 | Blattner |
| 5,352,612 A | 10/1994 | Huber et al. |
| 5,355,439 A | 10/1994 | Bernstein et al. |
| 5,355,695 A | 10/1994 | Kawaguchi |
| 5,356,595 A | 10/1994 | Kanamori et al. |
| 5,356,814 A | 10/1994 | Carrico, Jr. et al. |
| 5,358,691 A | 10/1994 | Clark et al. |
| 5,376,313 A | 12/1994 | Kanewske, III et al. |
| 5,402,350 A | 3/1995 | Kline |
| 5,424,036 A | 6/1995 | Ushikubo |
| 5,425,918 A | 6/1995 | Healey et al. |
| 5,428,470 A | 6/1995 | Labriola, II |
| 5,431,309 A | 7/1995 | Ophardt |
| 5,439,645 A | 8/1995 | Saralegui et al. |
| 5,439,649 A | 8/1995 | Tseung et al. |
| 5,446,652 A | 8/1995 | Peterson et al. |
| 5,475,610 A | 12/1995 | Atwood et al. |
| 5,479,581 A | 12/1995 | Kleinschnitz |
| 5,496,518 A | 3/1996 | Arai et al. |
| 5,512,248 A | 4/1996 | Van |
| 5,523,056 A | 6/1996 | Miller |
| 5,525,302 A | 6/1996 | Astle |
| 5,525,515 A | 6/1996 | Blattner |
| 5,573,727 A | 11/1996 | Keefe |
| 5,575,976 A | 11/1996 | Choperena et al. |
| 5,576,215 A | 11/1996 | Burns et al. |
| 5,578,455 A | 11/1996 | Tosa et al. |
| 5,595,707 A | 1/1997 | Copeland et al. |
| 5,601,141 A | 2/1997 | Gordon et al. |
| 5,614,376 A | 3/1997 | Copley et al. |
| 5,629,201 A | 5/1997 | Nugteren et al. |
| 5,639,665 A | 6/1997 | Arai et al. |
| 5,645,114 A | 7/1997 | Bogen et al. |
| 5,645,800 A | 7/1997 | Masterson et al. |
| 5,646,046 A | 7/1997 | Fischer et al. |
| 5,646,049 A | 7/1997 | Tayi |
| 5,650,327 A | 7/1997 | Copeland et al. |
| 5,654,199 A | 8/1997 | Copeland et al. |
| 5,654,200 A | 8/1997 | Copeland et al. |
| 5,656,493 A | 8/1997 | Mullis et al. |
| 5,672,512 A | 9/1997 | Shaw |
| 5,674,454 A | 10/1997 | Karl et al. |
| 5,675,715 A | 10/1997 | Bernstein et al. |
| 5,690,892 A | 11/1997 | Babler et al. |
| 5,695,718 A | 12/1997 | Imai et al. |
| 5,696,887 A | 12/1997 | Bernstein et al. |
| 5,700,346 A | 12/1997 | Edwards |
| 5,736,105 A | 4/1998 | Astle |
| 5,737,498 A | 4/1998 | Murray |
| 5,737,499 A | 4/1998 | Bernstein et al. |
| 5,819,842 A | 10/1998 | Potter et al. |
| 5,839,091 A | 11/1998 | Rhett et al. |
| 5,854,075 A | 12/1998 | Levine et al. |
| 5,861,094 A | 1/1999 | Goehde |
| 5,869,006 A | 2/1999 | Fanning et al. |
| 5,871,696 A | 2/1999 | Roberts et al. |
| 5,875,286 A | 2/1999 | Bernstein et al. |
| 5,895,628 A | 4/1999 | Heid et al. |
| 5,909,674 A | 6/1999 | Schaffer et al. |
| 5,917,675 A | 6/1999 | Yang |
| 5,930,461 A | 7/1999 | Bernstein et al. |
| 5,947,167 A | 9/1999 | Bogen et al. |
| 5,948,349 A * | 9/1999 | Beurotte et al. ................ 266/44 |
| 5,948,359 A | 9/1999 | Kalra et al. |
| 5,958,341 A | 9/1999 | Chu |
| 5,975,740 A | 11/1999 | Lin et al. |
| 5,985,669 A | 11/1999 | Palander |
| 5,985,672 A | 11/1999 | Kegelman et al. |
| 6,004,512 A | 12/1999 | Titcomb et al. |
| 6,017,495 A | 1/2000 | Ljungmann |
| 6,054,099 A | 4/2000 | Levy |
| 6,068,393 A | 5/2000 | Hutchins et al. |
| 6,076,583 A | 6/2000 | Edwards |
| 6,080,363 A | 6/2000 | Takahashi et al. |
| 6,093,574 A | 7/2000 | Druyor-Sanchez et al. |
| 6,096,271 A | 8/2000 | Bogen et al. |
| 6,110,425 A | 8/2000 | Gao et al. |
| 6,136,270 A | 10/2000 | Maes et al. |
| 6,180,060 B1 | 1/2001 | Green et al. |
| 6,180,061 B1 | 1/2001 | Bogen et al. |
| 6,183,645 B1 | 2/2001 | DeWitt |
| 6,183,693 B1 | 2/2001 | Bogen et al. |
| 6,193,933 B1 | 2/2001 | Sasaki et al. |
| 6,258,322 B1 | 7/2001 | Meikle |
| 6,284,543 B1 | 9/2001 | Alvarez |
| 6,296,764 B1 | 10/2001 | Guirguis et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,368,067 B1 | 4/2002 | Stutz |
| 6,372,144 B1 | 4/2002 | Vassarotti |
| 6,387,326 B1 | 5/2002 | Edwards et al. |
| 6,395,554 B1 | 5/2002 | Regan et al. |
| 6,436,348 B1 | 8/2002 | Ljungmann et al. |
| 6,451,551 B1 | 9/2002 | Zhan et al. |
| 6,471,958 B2 | 10/2002 | Dimitrijevich et al. |
| 6,472,217 B1 | 10/2002 | Richards et al. |
| 6,495,106 B1 | 12/2002 | Kalra et al. |
| 6,537,818 B2 | 3/2003 | Richards et al. |
| 6,585,936 B1 | 7/2003 | Shah |
| 6,594,537 B1 | 7/2003 | Bernstein et al. |
| 6,626,224 B1 | 9/2003 | Ljungmann |
| 6,632,598 B1 | 10/2003 | Zhang et al. |
| 6,635,225 B1 | 10/2003 | Thiem et al. |
| 6,649,128 B1 | 11/2003 | Meyer et al. |
| 6,685,884 B2 | 2/2004 | Stylli et al. |
| 6,703,247 B1 | 3/2004 | Chu |
| 6,746,851 B1 | 6/2004 | Tseung et al. |
| 6,759,011 B1 | 7/2004 | Richards et al. |
| 6,821,072 B2 | 11/2004 | Thiem et al. |
| 6,827,900 B2 | 12/2004 | Thiem et al. |
| 6,827,901 B2 | 12/2004 | Copeland et al. |
| 6,881,579 B2 | 4/2005 | Hilson et al. |
| 6,887,428 B2 | 5/2005 | Wernz et al. |
| 6,979,425 B1 | 12/2005 | Ganz et al. |
| 6,998,094 B2 | 2/2006 | Haslam et al. |
| 6,998,270 B2 | 2/2006 | Tseung et al. |
| 7,153,474 B2 * | 12/2006 | Thiem ............................ 422/63 |
| 7,262,022 B2 * | 8/2007 | Chu ........................... 435/40.5 |
| 7,270,785 B1 | 9/2007 | Lemme et al. |
| 7,271,006 B2 | 9/2007 | Reinhardt et al. |
| 7,273,591 B2 | 9/2007 | Sellers et al. |
| 7,303,725 B2 | 12/2007 | Reinhardt et al. |
| 7,314,595 B2 | 1/2008 | Honkanen et al. |
| 7,368,081 B2 | 5/2008 | Thiem |
| 7,435,383 B2 | 10/2008 | Tseung et al. |
| 7,468,161 B2 | 12/2008 | Reinhardt et al. |
| 7,501,283 B2 | 3/2009 | Hersch et al. |
| 7,553,672 B2 | 6/2009 | Bogen et al. |
| 7,584,019 B2 | 9/2009 | Feingold et al. |
| 7,744,817 B2 | 6/2010 | Bui |
| 7,860,727 B2 | 12/2010 | Showalter et al. |
| 8,048,373 B2 | 11/2011 | Reinhardt et al. |
| 8,663,991 B2 * | 3/2014 | Reinhardt et al. .............. 436/46 |
| 8,719,053 B2 | 5/2014 | Showalter et al. |
| 2001/0004449 A1 | 6/2001 | Suzuki et al. |
| 2001/0016358 A1 | 8/2001 | Osawa et al. |
| 2001/0019702 A1 | 9/2001 | Watari et al. |
| 2001/0019703 A1 | 9/2001 | Thiem et al. |
| 2001/0055545 A1 | 12/2001 | Takii et al. |
| 2002/0018733 A1 | 2/2002 | Kapplein et al. |
| 2002/0037239 A1 | 3/2002 | Komatsu |
| 2002/0054830 A1 | 5/2002 | Bogen et al. |
| 2002/0057992 A1 | 5/2002 | Eckert et al. |
| 2002/0064482 A1 | 5/2002 | Tisone et al. |
| 2002/0110494 A1 | 8/2002 | Lemme et al. |
| 2002/0116132 A1 | 8/2002 | Rhett et al. |
| 2003/0026732 A1 | 2/2003 | Gordon et al. |
| 2003/0047863 A1 | 3/2003 | Lang et al. |
| 2003/0049104 A1 | 3/2003 | Thiem et al. |
| 2003/0092186 A1 | 5/2003 | Pressman et al. |
| 2003/0099580 A1 | 5/2003 | Pressman et al. |

(56) References Cited

U.S. PATENT DOCUMENTS

| | | |
|---|---|---|
| 2003/0161761 A1 | 8/2003 | Williams et al. |
| 2003/0203493 A1 | 10/2003 | Lemme et al. |
| 2003/0211630 A1 | 11/2003 | Richards et al. |
| 2003/0215357 A1 | 11/2003 | Malterer et al. |
| 2003/0215936 A1 | 11/2003 | Kallioniemi et al. |
| 2004/0002163 A1 | 1/2004 | Reinhardt et al. |
| 2004/0009098 A1 | 1/2004 | Torre-Bueno |
| 2004/0038408 A1 | 2/2004 | Abbott et al. |
| 2004/0052685 A1 | 3/2004 | Richards et al. |
| 2004/0092024 A1 | 5/2004 | Reinhardt et al. |
| 2004/0121485 A1 | 6/2004 | Hopkins et al. |
| 2004/0136868 A1 | 7/2004 | Bevirt et al. |
| 2004/0197230 A1 | 10/2004 | Lemme et al. |
| 2005/0042137 A1 | 2/2005 | Petersen et al. |
| 2005/0047971 A1 | 3/2005 | Clements et al. |
| 2005/0053526 A1 | 3/2005 | Angros |
| 2005/0089444 A1 | 4/2005 | Justin et al. |
| 2005/0118670 A1 | 6/2005 | Lihl et al. |
| 2005/0186114 A1 | 8/2005 | Reinhardt et al. |
| 2005/0238534 A1 | 10/2005 | Chu |
| 2005/0250211 A1 | 11/2005 | Reinhardt et al. |
| 2006/0088928 A1 | 4/2006 | Sweet et al. |
| 2006/0120621 A1 | 6/2006 | Larkin et al. |
| 2006/0120921 A1 | 6/2006 | Elliot et al. |
| 2006/0120925 A1 | 6/2006 | Takayama et al. |
| 2006/0127276 A1 | 6/2006 | Ljungmann et al. |
| 2006/0134732 A1 | 6/2006 | Kram et al. |

FOREIGN PATENT DOCUMENTS

| | | |
|---|---|---|
| CA | 2321823 | 9/1999 |
| CA | 2482441 | 10/2003 |
| EP | 0240134 | 10/1987 |
| EP | 0517835 | 2/1996 |
| EP | 0722363 | 4/1999 |
| EP | 0600939 | 10/1999 |
| EP | 1052497 | 11/2000 |
| EP | 1477838 | 11/2004 |
| EP | 1890127 | 2/2008 |
| FR | 2239167 | 2/1975 |
| FR | 2528122 | 12/1983 |
| GB | 2143205 | 2/1985 |
| GB | 2216259 | 10/1989 |
| JP | 55-014157 | 1/1980 |
| JP | 55-107957 | 8/1980 |
| JP | 61-219847 | 9/1986 |
| JP | 63-208761 | 8/1988 |
| JP | 04-356845 | 12/1992 |
| JP | 05-504627 | 7/1993 |
| JP | 09-503304 | 3/1997 |
| JP | 2001-242175 | 9/2001 |
| JP | 2001-516869 | 10/2001 |
| JP | 2002-511600 | 4/2002 |
| JP | 2002-267642 | 9/2002 |
| JP | 2002-267942 | 9/2002 |
| JP | 2003-344242 | 12/2003 |
| JP | 2004-506228 | 2/2004 |
| JP | 2013-092532 | 5/2013 |
| WO | 8700086 | 1/1987 |
| WO | 8802865 | 4/1988 |
| WO | 9113335 | 9/1991 |
| WO | 9201919 | 2/1992 |
| WO | 9219952 | 11/1992 |
| WO | 9323732 | 11/1993 |
| WO | 9510035 | 4/1995 |
| WO | 9524498 | 9/1995 |
| WO | 9909390 | 2/1999 |
| WO | 9944032 | 9/1999 |
| WO | 9953357 | 10/1999 |
| WO | 0014534 | 3/2000 |
| WO | 0062035 | 10/2000 |
| WO | 0151909 | 7/2001 |
| WO | 0173399 | 10/2001 |
| WO | 0212857 | 2/2002 |
| WO | 02074525 | 9/2002 |
| WO | 03045560 | 6/2003 |
| WO | 03052386 | 6/2003 |
| WO | 03089140 | 10/2003 |
| WO | 03091710 | 11/2003 |
| WO | 03106157 | 12/2003 |
| WO | 2004001390 | 12/2003 |
| WO | 2004008106 | 1/2004 |
| WO | 2004074845 | 9/2004 |
| WO | 2005031312 | 4/2005 |
| WO | 2006073910 | 7/2006 |

OTHER PUBLICATIONS

"DAKO Autostainer Features and Specifications," DAKO Corporation, 3 pages, [retrieved on Dec. 7, 2000]. Retrieved from the Internet <URL: http://www.dakousa.com>.
"i 6000," Article from BioGenex, 2000, 4 pages.
"Laboratory Equipment 1998 and 1999," article from Shandon, Inc., pp. 37-51.
"Sakura Tissue-Tek DRS 2000 Slide Stainer," article from Sakura Finetek U.S.A., Inc., 1998, 1 page.
"Tissue-Tek DRS 2000 Automatic Multiple Slide Stainer: Multiple with Double Quality," Article from Sakura Fintek Europe B.V., 1998, 4 pages.
"Tissue-Tek DRS 2000 Slide Stainer: Computer-Assisted Flexibility for Unmatched Productivity," Article from Sakura Finetek, U.S.A., Inc., 1998, 4 pages.
"Varistain 24-4: Flexible, Efficient Automatic Slide Stainer," article from Shandon, Inc., 1991, 8 pages.
"Varistain 24-4K: High Throughput Continuous Slide Stainer," article from Shandon, Inc., 1991, 2 pages.
"Varistain XY Multi-Program Robotic Slide Stainer," article from Shandon, Inc., 1991, 8 pages.
Bartusch, M. et al., "Scheduling Project Networks with Resource Constraints and Time Windows," Annals of Operations Research, vol. 16, 1988, pp. 201-240.
Brigati, D. J. et al., "Immunocytochemistry is Automated: Development of a Robotic Workstation Based Upon the Capillary Action Principle," The Journal of Histotechnology, vol. 11, No. 3, Sep. 1998, pp. 165-183.
Conference Proceedings Presented at the 2000 National Society for Histotechnology Convention, "An Automated In Situ Hybridization System with High Throughput Capabilities," Biogenex, 2000, 2 pages.
Critchlow, A. J., "Introduction to Robotics," MacMillan Publishing Co., New York, 1985, pp. 37-56, 151-213.
Driscoll, R. C. et al., "II Analytical Systems: Discrete Automated Chemistry System with Tableted Reagents," Clinical Chemistry, vol. 29, No. 9, 1983, pp. 1609-1615.
Flore, M. et al., "The Abbott IMx Automated Benchtop Immunochemistry Analyzer System," Clinical Chemistry, vol. 34, No. 9, 1988, pp. 1726-1732.
Fouda, H. G. et al., "Robotics for the Bioanalytical Laboratory: A Flexible System for the Analysis of Drugs in Biological Fluids," Trac Trends in Analytical Chemistry, 1987, 10 pages.
Hamacher, V. C. et al., "Computer Organization," 2nd Edition, McGraw-Hill Book Company, New York, pp. 1-14, 1984.
Hayes, F. et al., "A Guide to GUIs," Byte, Jul. 1989, pp. 250-257.
Innis, M. A. et al., "DNA Sequencing with Thermus Aquaticus DNA Polymerase and Direct Sequencing of Polymerase Chain Reaction-Amplified DNA," Proceedings of the National Academy of Sciences USA, vol. 85, Dec. 1988, pp. 9436-9440.
International Search Report for PCT/US2003/11651 (related to present application); Applicant: Ventana Medical Systems, Inc., Mailed on Jul. 30, 2003, 2 pages.
Isenhour, T. L. et al., "Intelligent Robots—The Next Step in Laboratory Automation," Analytical Chemistry, vol. 61, No. 13, Jul. 1989, pp. 805-814.
Isenhour, T. L. et al,, "Laboratory Robotics and Artificial Intelligence," Clinical Chemistry, vol. 36, No. 9, 1990, pp. 1561-1566.
Isenhour, T. L. et al., "TORTS: An Expert System for Temporal Optimization of Robotic Procedures," Journal of Chemical Information an Computer Sciences, vol. 28, No. 4, 1998, pp. 215-221.

(56) References Cited

OTHER PUBLICATIONS

Isenhour, T. L., "Robotics in the Laboratory," Journal of Chemical Information and Computer Sciences, vol. 25, No. 3, 1985, pp. 292-295.
Kawaba, S. et al., "Robot Task Planning System Based on Product Modeling," IEEE, 1985, pp. 471-476.
Lindsey, J. S. et al., "Robotic Work Station for Microscale Synthetic Chemistry: On-Line Absorption Spectroscopy, Quantitative Automated Thin-Layer Chromatography, and Multiple Reactions in Parallel," Review of Scientific Instruments, vol. 59, No. 6, Jun. 1988, pp. 940-950.
Longnecker, D. S., "A Program for Automated Hernatoxylin and Eosin Staining," Technical Bulletin of the Registry of Medical Technologists, vol. 36, No. 1, 1966, p. 19.
MaWhinney, W. H. B. et al, "Automated Immunochemistry," Journal of Clinical Pathology, vol. 43, 1990, pp. 591-596.
McCahon, C. S. et al., "Job Sequencing with Fuzzy Processing Times," Computers & Mathematics with Applications, vol. 19, No. 7, 1990, pp. 31-41.
Montone, K. T. et al., "Anatomic Viral Detection is Automated: The Application of a Robotic Molecular Pathology System for the Detection of DNA Viruses in Anatomic Pathlogy Substrates, Using Immunocytochemical and Nucleic Acid Hybridization Techniques," The Yale Journal of Biology and Medicine, vol. 62, 1989, pp. 141-158.
Mueller N. J. et al., "Concurrent HPLC Analyses of Carbohydrate Distribution and 5-(Hydroxymethyl)-2-Furaldehyde Using Robotics," Journal of Chromatographic Science, vol. 25, 1987, pp. 198-201.
Okino, N. et al., "Robot Simulator in Tips/Geometric Simulator," Robotics and Computer Integrated Manufacturing, vol. 3, No. 4, 1987, pp. 429-437.
Plakhtin, D. L., "Use of Automatic Devices for Histological Processing and Staining of the Tissues and Certain Characteristics of Preparation of Histological Specimens," Arkh Patol, vol. 38, No. 11, 1976, pp. 76-77, Abstract Only.
Saiki, R. K. et al., "Enzymatic Amplification of β-Globin Genomic Sequences and Restriction Site Analysis for Diagnosis of Sickle Cell Anemia," Science, vol. 230, Dec. 1985, pp. 1350-1354.
Sjolund, P. et al., "Robot Task Planning: Programming Using Interactive Computer Graphics," Apr. 1983, pp. 7-122-7-135.
Solomon, M. M. et al., "Time Window Constrained Routing and Scheduling Problems," Transportation Science, vol. 22, No. 1, Feb. 1988, pp. 1-13.
Stark, E. et al., "An Automated Device for Immunocytochemistry," Journal of Immunological Methods, vol. 107, 1988, pp. 89-92.
Stelzner, M. et al., "The SimKit System: Knowledge-Based Simulation and Modeling Tools in Kee," An Intellicorp Technical Article, 1987, 22 pages.
Stross, W. P. et al., "Automation of APAAP Immunocytochemical Technique," Journal of Clinical Pathology, vol. 42, 1989, pp. 106-112.
Unger, E. R. et al., "Colorimetric In-Situ Hybridization in Clinical Virology: Development of Automated Technology," Current Topics in Microbiology and Immunology, vol. 143, 1989, pp. 21-31.
Unger, E. R. et al., "Viral Diagnosis by In Situ Hybridization: Description of a Rapid Simplified Colometric Method," The American Journal of Surgical Pathology, vol. 10, No. 1, 1986, pp. 1-8.
Viglierchio, D.R., et al., "Automatic Solvent Exchanger," Transactions of the American Microscopical Society 84, Department of Nematology, University of California, Davis, 1965, pp. 284-293.
"Capillary Action Slide Stainers for Histology and Cytology," Article from Fisher Scientific, Date: Unkown (for purposes of examination date is assumed to be prior to filing date of Apr. 15, 2002), 4 pgs.
"The New Protocol in Staining Technology," Article from Fisher Healthcare, Date: Unknown (for purposes of examination date is assumed to be prior to filing date of Apr. 15, 2002), 5 pgs.
Leica ST 4040 and Leica Autostainer XL, description, Date: Unknown (for purposes of examination date is assumed to be prior to filing date of Apr. 15, 2002).
"Advanta CV/AS," Article from Vision Instruments, Date: Unknown (for purposes of examination date is assumed to be prior to filing date of Apr. 15, 2002), 2 pgs.
"Leica Auto Stainer XL," Article from Leica, Date: Unknown (for purposes of examination date is assumed to be prior to filing date of Apr. 15, 2002), 4 pgs.
"Tissue-Stainer TST 40," Article from Medite, Date: Unknown (for purposes of examination date is assumed to be prior to filing date of Apr. 15, 2002), 2 pgs.
"TST Stainer Trio," Article from Mopec, Date: Unknown (for purposes of examination date is assumed to be prior to filing date of Apr. 15, 2002), 7 pgs.
"Robot-Stainer HMS 760, Automatic Slide Stainer for Routine Histology and Cytology Applications," Article from Microm Histology Products, Date: Unknown (for purposes of examination date is assumed to be prior to filing date of Apr. 15, 2002), 4 pgs.
"ST 5050 Zymed's Sensible IHC Automated Staining Solution," Article from Zymed Laboratories, Date: Unknown (for purposes of examination date is assumed to be prior to filing date of Apr. 15, 2002), 2 pgs.

* cited by examiner

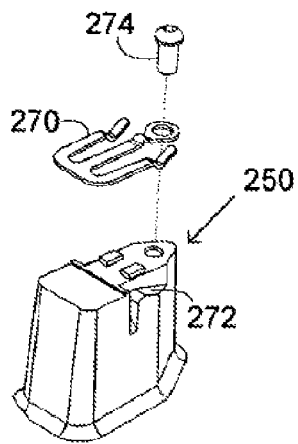
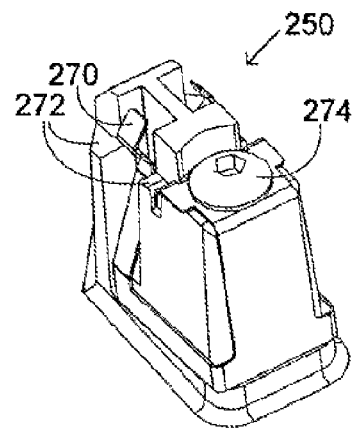
FIG. 8A  FIG. 8B
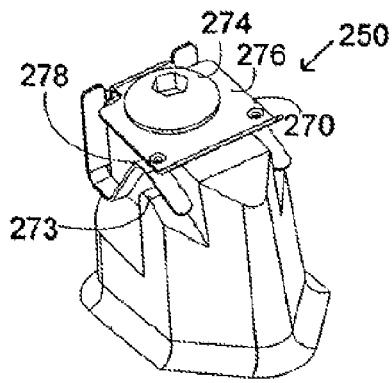
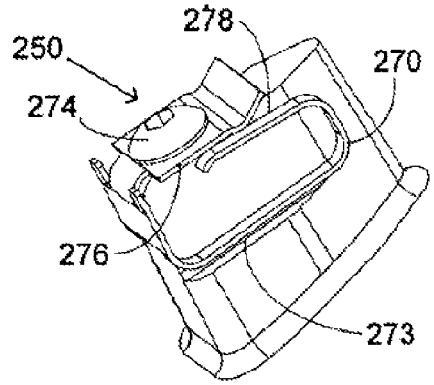
FIG. 8C  FIG. 8D
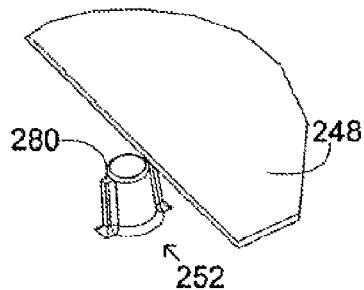
FIG. 8E

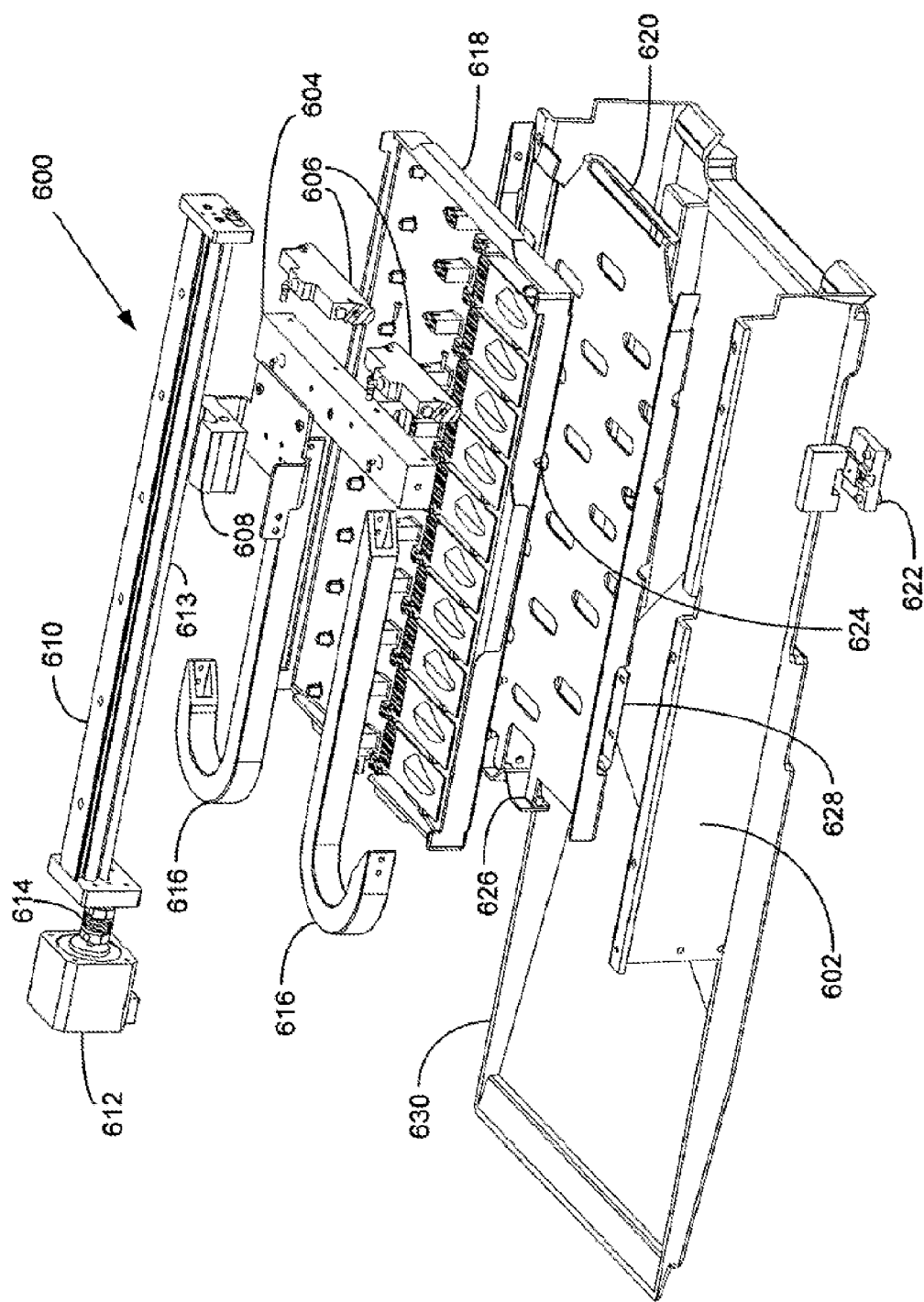

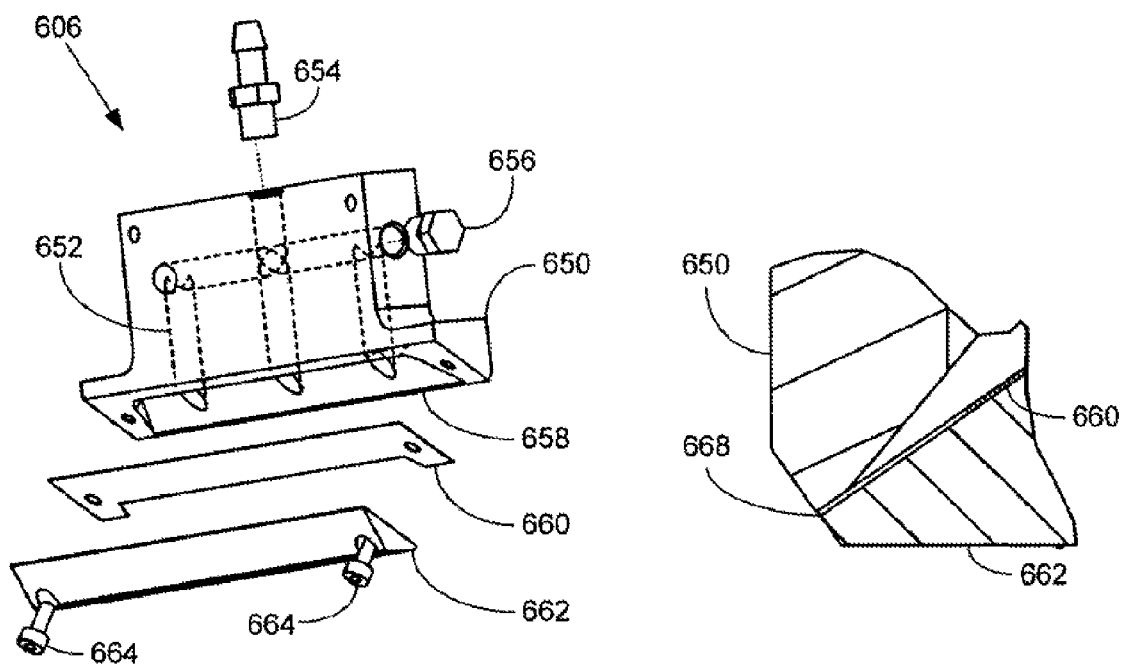
FIG. 17A
FIG. 17B
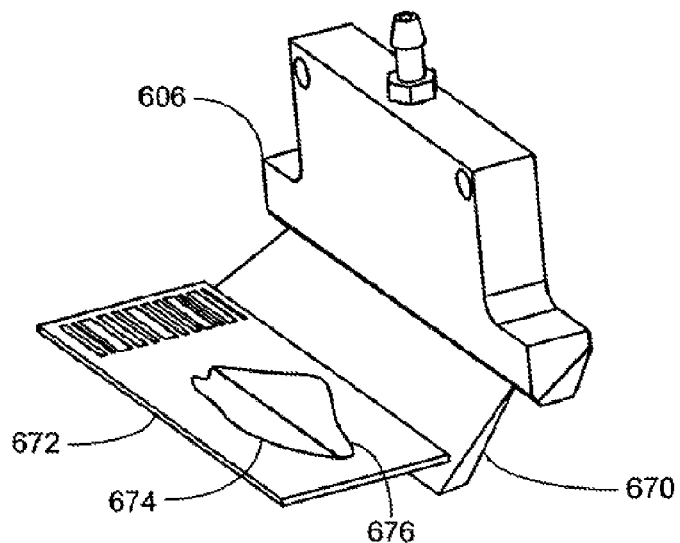
FIG. 17C

AUTOMATED HIGH VOLUME SLIDE PROCESSING SYSTEM

CROSS-REFERENCE TO RELATED APPLICATIONS

This application is a Continuation of U.S. patent application Ser. No. 11/181,625, filed Jul. 13, 2005, which is a Divisional of U.S. patent application Ser. No. 11/116,676, filed Apr. 27, 2005 (U.S. Pat. No. 7,468,161), which is a Continuation-in-Part of U.S. patent application Ser. No. 10/414,804, filed Apr. 15, 2003 (U.S. Pat. No. 7,303,725), which claims the benefit of U.S. Provisional Patent Application No. 60/372,506, filed Apr. 15, 2002, which are hereby incorporated by reference in their entireties.

BACKGROUND OF THE INVENTION

1. Field

The present invention relates to equipment and methods for preparing samples for analysis. In particular, equipment and methods are provided for automated staining of biological samples on microscope slides.

2. Background

Many tissues do not retain enough color after processing to make their components visible under a bright-field microscope. Accordingly, it is common practice to add color and contrast to tissue components by staining the tissue with various reagents. In the past, the steps of staining a tissue sample for histological or cytological analysis were performed manually, a process that is inherently inconsistent. Inconsistent staining makes it difficult for a Histologist or other medical personnel to interpret slides and to make comparisons between different samples. Thus, a number of devices and methods have been described that serve to automate the staining process and reduce staining inconsistency. Labor costs and the burgeoning demand for anatomical pathology services also are driving the push for increased automation of the staining process.

Prior art devices for automated staining, especially for high volume staining with traditional reagents such as hematoxylin and eosin (H&E), are primarily of a "dip and dunk" type, where racks of slides are automatically lowered into and removed from a series of reagent baths. For example, U.S. Pat. No. 4,911,098 to Tabata describes an automated staining apparatus, where microscope slides holding tissue specimens are dipped sequentially into a large number of chemical solution containers. The slides are mounted vertically in a slide holder basket and a clamp that engages and disengages the basket is used to move the slides from solution to solution. The clamp can include a mechanism to tilt the basket, which aids in removing excess solution before the basket is submerged in the next solution. Additional automated staining devices of the "dip and dunk" type are described in U.S. Pat. No. 5,573,727 to Keefe, U.S. Pat. No. 6,080,363 to Takahasi et al., U.S. Pat. No. 6,436,348 to Ljungmann et al. and U.S. Patent Application Publication No. 2001/0019703, naming Thiem et al. as inventors.

A common shortcoming of the automated "dip and dunk" staining devices is the possibility for cross-contamination of samples that are simultaneously or sequentially introduced into the same solution baths. For example, cells that become dislodged from one slide can settle onto other slides introduced into the same bath. Another problem inherent to these designs is that as slide baskets are transferred from one bath to another, solutions used in later steps of the staining process become contaminated with residual amounts of solutions used earlier in the process. Furthermore, degradation (such as through oxidation) of solution components over time can lead to inconsistent staining unless the solutions are regularly replenished or exchanged, which is a time-consuming and wasteful process that typically disrupts work-flow in these "dip and dunk" type of automated stainers.

Another type of automatic staining apparatus delivers fresh reagents directly to individual slides. For example, U.S. Pat. No. 6,387,326 to Edwards et al. describes an apparatus for staining slides where slides are expelled one at a time from a slide storage device and individually treated at various staining stations as they move along a conveyor belt transport apparatus. Additional devices for automatically staining individual slides are described in U.S. Pat. No. 6,180,061 to Bogen et al., PCT Publication WO 03/045560, naming Tseung et al. as inventors, and U.S. Patent Application Publication No. US2004/0052685 naming Richards et al. as inventors. While such devices can successfully minimize cross-contamination of slides and help ensure that samples are consistently treated with fresh reagent, the individual treatment of slides lowers throughput. Therefore, the throughput of these individual slide staining devices can be problematic for use in primary staining applications (such as H&E staining) where the number of samples processed in a histology laboratory can run into the hundreds or even thousands per day.

What is needed, therefore, is an apparatus and method for consistent, high-throughput staining of microscope slides that also minimizes the potential for cross-contamination between slides. Furthermore, an apparatus and method that can be replenished with fresh reagents without interruption of work-flow is desirable.

SUMMARY OF THE INVENTION

An automated system is provided for performing slide processing operations on slides bearing biological samples. The system enables high sample throughput and increased staining consistency while also minimizing the potential for cross-contamination of slides.

In one aspect of the disclosed system, a workstation for performing a step of a staining protocol is not a bath containing a reagent in which several slides are simultaneously immersed. Rather, according to this aspect, a workstation of the system dispenses a reagent to a plurality of microscope slides with minimal transfer of reagent (and contaminants therein) between individual slides. Thus, a workstation according to this aspect minimizes or substantially eliminates the type of cross-contamination of slides that occurs in prior art "dip and dunk" type automated slide staining systems, where contaminants such as dislodged cells can be transferred through the reagent bath from one slide to another.

In one embodiment, the disclosed system includes a slide tray holding a plurality of slides in a substantially horizontal position and a workstation that receives the slide tray. In a particular embodiment, a workstation delivers a reagent to slide surfaces without substantial transfer of reagent (and reagent borne contaminants such as dislodged cells) from one slide to another. In another particular embodiment, the slide tray holding the plurality of slides holds two or more rows or banks of slides, for example, two rows of 4-10 slides each.

In a more particular embodiment, slides are held in a rectangular slide tray in two rows such that their long dimensions are disposed outward from the central, long axis of the tray toward the long edges of the tray. A reagent dispenser in a workstation is positioned above one or more pairs of slides in the opposite rows, and delivers a reagent to one or more slides in one or the other of the two rows, for example, to a pair of slides that are opposite from each other in the two rows. If the reagent dispenser is positioned above fewer than the total number of slides that are held in the tray, the reagent dispenser can move to dispense reagent to other slides in each row of slides, and/or the slide tray can be moved to bring additional slides into position for reagent dispensing. Alternatively, two or more stationary or moving reagent dispensers can be included in the workstation, or one or more manifolds of dispense nozzles can be positioned above the two rows of slides, for example, along the central, long axis of the tray. Nozzles of a reagent dispenser can direct reagent downward and/or upward toward surfaces of slides.

In another particular embodiment, a workstation includes two or more sets of nozzles that are formed or inserted into a movable block that can be moved along the central, long axis of the tray to dispense reagents to one or more slides, for example, a pair of slides disposed toward opposite sides of the tray. Since slides are held in the slide tray so that they are not touching each other, and the slides are held parallel to one another along the direction in which a reagent is dispensed from the nozzles, reagent applied to one slide has a minimal or substantially non-existent chance of reaching another slide and thereby cross-contaminating the slides.

In another aspect, the disclosed system can include one or more workstations where biological samples on slides can be subjected to various treatments including drying, baking, de-paraffinizing, pre-stain prepping, staining, coverslipping and sealing, and combinations thereof. A transporter also is included for moving a slide tray carrying a plurality of slides between the plurality of workstations. Additionally, a fluidics module, a pneumatics module and a control module can be included to deliver reagents, deliver vacuum and/or pressurized gas, and coordinate function of system components, respectively.

In a particular working embodiment, the disclosed system includes a plurality of workstations that are arranged in a vertical stack and a transporter that comprises an elevator configured to move a slide tray between the vertically arranged workstations and an X-Y shuttle table configured to move a slide tray horizontally, such as in and out of a workstation, in and out of the system itself, or in and out of a parking garage. Particular examples of workstations that can be included in the system are a baking or drying station, a de-waxing or de-paraffinizing station, one or more staining stations and a coverslipping station. In a more particular embodiment, a workstation is provided that can perform two or more of de-paraffinizing, staining and solvent exchanging. In even more particular embodiments, such a workstation has a moveable nozzle assembly configured to deliver reagents to individual slides held in a slide tray. Workstations according to the disclosure can be modular and include common electrical, pneumatic and fluidic interfaces such that workstation can be easily added or removed to any of several positions within a slide processing system.

In another aspect, a fluidics module is disclosed for automated handling of reagents that can deliver reagents in packaged concentration or in diluted concentration to a workstation without the need to disrupt the delivery of such reagents by the workstation while replacing or replenishing reagents to the system. In more particular embodiments, the fluid-handling module includes a dual chamber fluid pump. The dual chamber fluid pump includes a pump chamber and a dispense chamber where the pump chamber is configured to alternate between vacuum and pressure. The two chambers and a set of valves allow the dispense chamber to be maintained at a constant pressure for dispensation of a reagent to slides even while additional reagent is added to the dispense chamber from the pump chamber. Alternatively, a pump chamber supplying a dispense chamber can further function as a dilution chamber, and a concentrate pump chamber can be added to provide concentrated solutions to the dilution chamber.

The disclosed system is capable of high throughput staining of biological samples on slides without the shortcomings of conventional dip and dunk systems, particularly by eliminating conventional dip-and-dunking de-paraffinizing and/or staining baths, which tend to degrade through oxidation and/or contamination by biological cells dislodged during the de-paraffinizing process. Instead, the disclosed system can employ fresh, clean reagents, thus minimizing the possibility of cell carryover from slide to slide. Moreover, the disclosed system provides for the first time a fully integrated high throughput system for staining slides from the baking step through the coverslipping step, a process that is not performed by any other commercially available system to date.

Further aspects, features and advantages of the disclosed embodiments will be apparent from the following detailed description of the invention, which proceeds with reference to the following drawings.

BRIEF DESCRIPTION OF THE DRAWINGS

FIGS. 8 A-E are a series of perspective views of several embodiments of slide holding components of a slide tray.

FIG. 16 is a perspective view showing the components of an embodiment of a solvent exchanger that can be included in the disclosed system.

FIGS. 17 A-C are a series of diagrams showing an embodiment of a blow-off nozzle that can also be used as an air broom.

DETAILED DESCRIPTION OF SEVERAL ILLUSTRATIVE EMBODIMENTS

Figure 1:
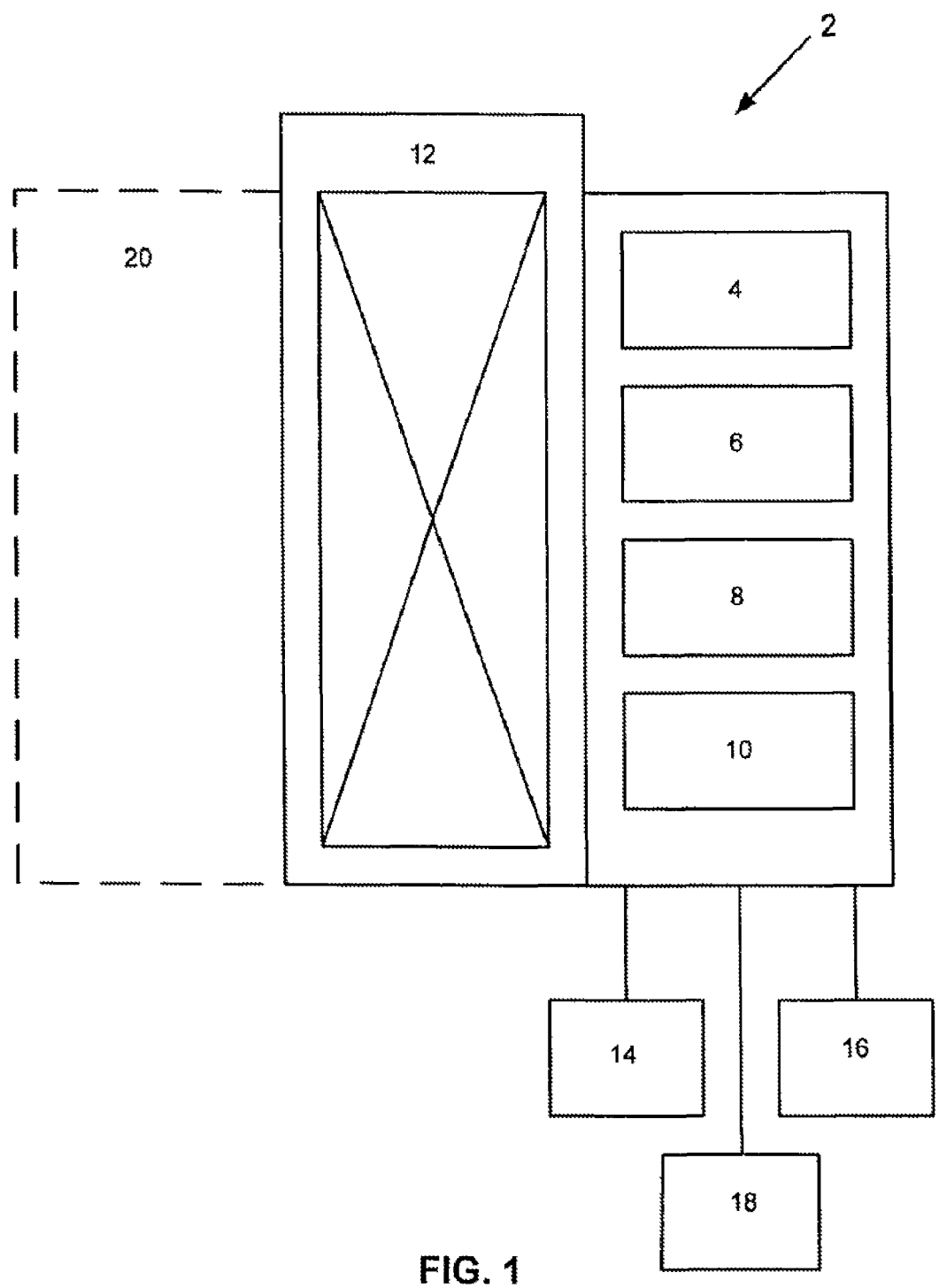
FIG. 1 is schematic diagram of an embodiment of the disclosed system.

The following description of several embodiments describes non-limiting examples of the disclosed system and methods to illustrate the invention. Furthermore, all titles of sections contained herein, including those appearing above, are not to be construed as limitations on the invention, rather they are provided to structure the illustrative description of the invention that is provided by the specification. Also, in order to facilitate understanding of the various embodiments, the following explanations of terms is provided.

I. Terms

The singular forms "a," "an," and "the" include plural referents unless the context clearly indicates otherwise. Thus, for example, reference to "a workstation" refers to one or more workstations, such as 2 or more workstations, 3 or more workstations, or 4 or more workstations.

The term "biological reaction apparatus" refers to any device in which a reagent is mixed with or applied to a biological sample, and more particularly to any automated device that performs one or more operations on a biological sample.

The term "biological sample" refers to any sample including biomolecules (such as proteins, peptides, nucleic acids, lipids, carbohydrates and combinations thereof) that is obtained from (or includes) any organism including viruses. Biological samples include tissue samples (such as tissue sections), cell samples (for example, cytological smears such as Pap or blood smears or samples of cells obtained by microdissection), samples of whole organisms (such as samples of yeast or bacteria), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules derived therefrom.

The term "code" refers to any type of optical symbology, magnetic pattern or electromagnetic or electrostatic signal containing information. A "code reader" is any type of device that can decipher the information contained in a code. Examples of optical symbologies include characters, barcodes and dataglyphs. Particular examples of barcodes include linear barcodes (such as EAN.UPC, EAN-128, ITF-14 and code 39) multi-dimensional barcodes such as 2D stacked symbologies and 2D matrix symbologies, and composite barcodes such as reduced space symbologies. Even more particular examples of 2D optical symbologies include (p, q) code, PDF417, data matrix, maxicode, vericode, codablock, aztec code, code 16K and QR code. Bar code readers for these and any number of other optical symbologies are well known. Where the code comprises characters (such as alphanumeric characters such as English text and Arabic numbers) the code reader can be an optical character reader (OCR). Magnetic stripes are only one example of a device that can store information in the form of a magnetic pattern. An example of an electromagnetic code is an RFID tag. RFID tags typically include a small metallic antenna and a silicon chip, and can be active or passive. RFID code readers are well known, and typically include an antenna and a transceiver that receives information from the RFID tag. The information content of an RFID tag can be fixed or changeable. In another embodiment, the code reader comprises a CCD camera and the CCD camera can be used for simultaneous detection of slides and reading of a barcode or characters.

The term "organic solvent compatible with coverslipping" refers to a non-aqueous solvent (or mixture of such solvents) that can dissolve a glue (such as on a pre-glued coverslip) used to affix a coverslip to a slide. Examples of such solvents include aliphatic and aromatic hydrocarbons including alkanes (such as branched or straight chain C6-C12 alkanes), terpenes (such as limonene) and benzene derivatives (such as toluene and xylene).

A "plurality" refers to two or more, for example, 3 or more, 4 or more, 5 or more, 10 or more, or even 20 or more.

As used herein, the term "reagent" refers to any liquid or liquid composition used in a slide processing operation that involves adding a liquid or liquid composition to a slide. Reagents include solutions, emulsions, suspensions and solvents (either pure or mixtures thereof). Reagents can be aqueous or non-aqueous. Examples of reagents include solutions or suspensions of antibodies, solutions or suspensions of nucleic acid probes, and solutions or suspensions of dye or stain molecules (such as H&E staining solutions and Pap staining solutions). Further examples of reagents include solvents and/or solutions for de-paraffinization of paraffin-embedded biological samples such as limonene, aqueous detergent solutions, and hydrocarbons (for example, alkanes, isoalkanes and aromatic compounds such as xylene). Additional examples of reagents include solvents (and mixtures thereof) that can be used to dehydrate or rehydrate biological samples, such as ethanol, water and mixtures thereof.

The term "slide" refers to any substrate (such as glass, quartz, plastic or silicon) of any dimensions on which a biological sample is placed for analysis, and more particularly to a "microscope slide" such as a standard 3"×1" glass slide or a standard 75 mm×25 mm glass slide. Examples of biological samples that can be placed on a slide include a cytological smear, a thin tissue section (such as from a biopsy), or alternatively, can be an array of biological samples, for example a tissue array, a DNA array, an RNA array, a protein array, or any combination thereof. Thus, in one embodiment, tissue sections, DNA samples, RNA samples, and/or proteins are placed on a slide at particular locations.

The term "slide processing operation" refers to any treatment or manipulation of a slide, either with or without a biological sample already placed thereon, or any treatment of a biological sample placed on a slide. Examples of slide processing operations include, but are not limited to, cleaning, heating, cooling, drying, baking, labeling, indexing, removing mercury deposits, re-hydrating, dehydrating, fixing, de-paraffinizing, decalcifying, bluing, digesting, preserving, pre-stain prepping, solvent exchanging, mounting, staining and coverslipping, and combinations thereof.

The term "staining" is used herein to refer to any treatment of a biological sample (such as a cellular smear or a tissue section) that detects and/or differentiates the presence, location and/or amount (such as concentration) of a particular molecule (such as a lipid, protein or nucleic acid) or particular structure (such as a normal or malignant cell, cytosol, nucleus, Golgi apparatus, or cytoskeleton) in the biological sample. For example, staining can provide contrast between a particular molecule or a particular cellular structure and surrounding portions of a biological sample, and the intensity of the staining can provide a measure of the amount of a particular molecule in the sample. Staining can be used to aid in the viewing of molecules, cellular structures and organisms not only with bright-field microscopes, but also with other viewing tools such as phase contrast microscopes, electron microscopes and fluorescence microscopes. Some staining methods can be used to visualize an outline of a cell. Other staining methods rely on certain cell components (such as molecules or structures) being stained without staining the rest of a cell. Examples of types of staining methods include histochemical methods, immunohistochemical methods and other methods based on reactions between molecules (including non-covalent binding interactions), for example, hybridization reactions between nucleic acid molecules. Particular staining methods include, but are not limited to, primary staining methods such as hematoxylin & eosin (H&E) staining and Pap staining, enzyme-linked immunohistochemical methods and in situ RNA and DNA hybridization methods such as fluorescence in situ hydbridization (FISH). Additional particular examples of staining methods can be found, for example, in Horobin and Kiernan, "Conn's biological stains: a handbook of dyes, stains and fluorochromes for use in biology and medicine," $10^{th}$ ed., Oxford: BIOS, ISBN 1859960995, 2002, and in Beesley, "Immunocytochemistry and in situ hybridization in the biomedical sciences," Boston: Birkhauser, ISBN 3764340657, 2002.

The term "substantially horizontal" generally refers to an angle within about +/−2 degrees of horizontal, for example, within about +/−1 degree of horizontal such as within about +/−0.8 degrees of horizontal. Substantially horizontal also refers to ranges of small angles from horizontal, for example, angles between about 0.1 degrees and 1.8 degrees from horizontal, such as angles between about 0.2 degrees and about 1.2 degrees, for example angles between about 0.3 degrees and about 0.8 degrees. A slide that is held substantially horizontal will have an orientation such that the large surfaces of the slide are generally facing up and down. In particular embodiments, a rectangular slide such as a microscope slide that is held substantially horizontal will have an angle with respect to horizontal of between about 0.0 degrees and about 2.0 degrees along its short axis and an angle with respect to horizontal of between about 0.0 degrees and 2.0 degrees along its long axis, again with the large surfaces of the slide generally facing up and down. Typically, if a slide has a barcode affixed to one end, a slide held in a substantially horizontal position will have a downward slope away from the barcode along its long axis.

The term "wicking member" refers to any structure (made from any material, for example, metal, plastic or glass) that can break the surface tension of a liquid held on a surface or in a container and facilitate liquid movement off of the surface or from the container. For example, a wicking member such as a small diameter fiber can come in contact with the edge of a slide, and facilitate movement of a liquid from a surface of the slide. A wicking member such as a wicking plate can also contact the edge of a slide tray surface (such as an edge of a bottom or side wall of a slide tray) to facilitate removal of a liquid accumulated in the slide tray. A wicking member is advantageously used in combination with a tilter that lifts a surface away from horizontal such that the surface slopes toward the wicking member. The combination of a wicking member and a tilter can substantially increase the efficiency with which a liquid can be removed from the surface or container.

The term "workstation" refers to a position or location in a disclosed system where at least one slide processing operation is performed, and more particularly to a modular unit inside of which one or more slide processing operations are performed on a plurality of slides held in a slide tray (for example, a plurality of slides held in a substantially horizontal position in a slide tray). A workstation can receive a slide tray in substantially a single position so that moveable components of the workstation can locate individual slides within the slide tray and precisely perform a slide processing operation on one or more slides in the tray (such as deliver a reagent to a particular slide or portion thereof). Examples of slide processing operations that can be performed by a workstation include heating, drying, de-paraffinizing, pre-stain prepping, rinsing, solvent exchanging, staining and coverslipping, and combinations thereof. In some embodiments, a workstation dispenses two or more reagents to a slide without the slides being moved from one workstation to another during a slide-processing operation or operations such as de-paraffinizing, staining and/or solvent exchanging. Thus, in one embodiment, a workstation includes a reagent delivery means such as a nozzle or a manifold of nozzles through which reagents are delivered to slides held in a slide tray, which delivery means can be moveable or fixed in position within the workstation. Thus, in contrast to some prior art "workstations" which are merely containers holding a reagent in which slides are immersed, a workstation according to the disclosure can be an active, mechanical device that delivers reagents (such as two or more reagents) to groups of slides held together in a slide tray. Thus, in one aspect a work station is not a reagent bath in which slide are immersed. In other embodiments, a workstation can include a heating element and can further include a heat directing element. A heat directing element can help to spread heat more evenly between slides held in a slide tray. A workstation also can include one or more radiant heaters. A workstation also can include a tray tilter (such as a tilt pan) to lift one end of a slide tray to assist with liquid removal from the tray. Alternatively a workstation can include a mechanism to tilt one or more individual slides in a slide tray away from a horizontal position. Workstations can further include various components that move or control other workstation components, such as stepper motors, screw drives and microprocessors. Other components that can be included in a workstation include hoses, belts, tracks, fluidics connections, metering pumps, metering valves, electrical connections, sensors and the like. In another embodiment, a workstation is a modular unit that can be interchanged between two or more positions within a disclosed system and electrically and fluidically connected to the system via a common electronics backplane and a common fluidics manifold. In yet another embodiment, a workstation can include a light source, such as a UV light source for curing an adhesive for holding a coverslip in place on a slide.

Additionally, sensors located at or near reagent supplies for a workstation (or at or near pumps that deliver reagents to a workstation) can monitor reagent volumes in the system and alert a user to a low reagent condition. Furthermore, sensors (such as RFID antennae) can also be used to track reagent data such as reagent identity, amounts and expiration dates to help ensure accurate and consistent reagent use in the system. Overflow conditions in workstations and/or in a waste management system can also be monitored with sensors.

II. Overview

The disclosed staining system can perform all the steps of processing, staining and coverslipping of slide mounted biological samples in an efficient high-speed operation (baking through coverslipping). In a particular embodiment, slides bearing biological samples are placed on a slide tray, and the slide tray bearing the sample slides is loaded into the system. Then, the slides in the slide tray are detected and indexed, and conducted through a sequence of slide processing operations, for example, baking, de-waxing, staining, coverslipping and drying.

In one aspect, the disclosed system is an automated slide processing system that includes a slide tray holding a plurality of slides in a substantially horizontal position (such as in two rows where the slides are held at an angle between about 0.2 degrees and about 1.2 degrees from horizontal) and one or more workstations (for example, arranged in a vertical stack) that receive the slide tray and perform one or more slide processing operations on slides in the slide tray. The workstation can perform a slide processing operation on one or more individual slides in a slide tray, for example, at least two or four slides in a slide tray, or it can simultaneously perform a slide processing operation on all of the slides in a slide tray. In particular embodiments, one or more workstations dispense a reagent to slides in the slide tray without a substantial amount of the reagent that contacts a first slide contacting a second slide, thereby minimizing cross-contamination between slides. Such workstations can include one or more directional nozzles that dispense the reagent onto the slides, for example, the one or more directional nozzles can include a pair of directional nozzles that dispense the reagent in opposite directions across a surface of a slide. In more particular embodiments, the one or more directional nozzles can further include a directional nozzle that dispenses the reagent towards a bottom surface of a slide. In other particular embodiments, the one or more workstations can simultaneously dispense a reagent (for example, the same reagent) to at least two slides held in a slide tray within a given workstation, or the one or more workstations can simultaneously dispense a reagent (such as the same reagent) to all of the slides held in the slide tray within a given workstation.

The disclosed system also can include a transporter to move a slide tray into and out of one or more workstations. Another example of a component or workstation that can be part of the disclosed system is a radiant heater, for example, a radiant heater that has a heat profile that provides substantially uniform heating of slides held in a slide tray positioned below the radiant heater. Yet another example of a workstation is a combined de-paraffinizer/stainer. In a particular embodiment, a combined de-paraffinizer/stainer includes a moveable nozzle assembly, wherein the nozzle assembly includes one or more nozzles through which reagent is dispensed to a slide. The nozzles in the nozzle assembly can be dispense nozzles, forward top surface rinse nozzles that can direct a stream of reagent toward a top surface of a slide (such as at an angle of between about 20 degrees and about 30 degrees relative to the top surface), backward top surface rinse nozzles that can direct a stream of reagent toward a top surface of a slide (such as at an angle of between about 20 degrees and about 50 degrees relative to the top surface), jet drain nozzles, and bottom surface rinse nozzles and combinations thereof. One or more splash guards can also be included on the nozzle assembly as can one or more air brooms or blow-off nozzles.

Yet another type of workstations that can be included in the disclosed system is a coverslipper. Other examples include a drying oven and a solvent exchanger. A transporter that can move a slide tray between workstations also can be included. In more particular embodiments, a workstation can include a slide tray tilter (such as a tilt pan) and a wicking member that facilitates removal of liquids from the slide tray. In conjunction, a slide tray can include an opening in a side wall of the slide tray, wherein the opening in the side wall is contacted by the wicking member in the workstation.

In a more particular embodiment, a disclosed system includes one or more workstations selected from the group consisting of a combined de-paraffinizer/stainer, a drying oven, a solvent exchanger, and a coverslipper, a radiant heater, and combinations thereof. The radiant heater can have a heat profile that provides substantially uniform heating of the slides held in the slide tray.

In another aspect an automated slide processing apparatus is provided that includes a plurality of workstations including a combined de-paraffinizer/stainer, a solvent exchanger, and a coverslipper; a slide tray holding a plurality of slides; and a transporter. The slides can be held substantially horizontal in the tray, and the workstations can be arranged in a vertical stack, such as a vertical stack where multiple workstations are arranged so they are essentially above or below other workstations in the stack. In a particular embodiment, the combined de-paraffinizer/stainer and the solvent exchanger dispense a reagent to slides in the slide tray without a substantial amount of the reagent that contacts a first slide contacting a second slide, thereby minimizing cross-contamination between slides. In more particular embodiments, the combined de-paraffinizer/stainer and the solvent exchanger each can include a moveable nozzle assembly can be positioned to dispense a reagent (such as the same reagent) to one or more slides in the plurality (either one at a time in series or simultaneously to any number less than the total number of slides in the tray), or the combined de-paraffinizer/stainer and the solvent exchanger each can simultaneously dispense a reagent (such as the same reagent) to one or more, (for example, all) of the slides in the plurality through a stationary nozzle manifold. In this aspect, the apparatus can further include a radiant heater and/or a drying oven, wherein the drying oven can be a convection oven, such as a convection oven including a heating element and a blower to distribute heat generated by the heating element across the slides held in the slide tray. A dehumidifier can also be included in the system to reduce humidity within a cabinet enclosing at least a portion of the system. Furthermore, a sensor such as code reader for identifying individual slides on the slide tray can be included in the system where one or more slides are marked with a code. Examples of codes that can be used to mark slides include one-dimensional barcodes, multidimensional barcodes, glyphs such as dataglyphs, RFID tags and magnetic stripes. One or more sensors (such as optical sensors) to detect the presence of individual slides (with or without a code) in particular positions within a slide tray can be included in the system, and one or more sensors (such as magnet/Hall-effect sensor combinations) can be included to detect the presence of a slide tray at particular positions within the system. Sensors for detecting individual slides in a slide tray can be used to ensure that reagents are not dispensed to positions in a slide tray where no slide has been placed, thereby reducing wasteful reagent consumption by the system. In a working embodiment, an optical reflectance detector is used to detect slides in the slide tray, and if a slide is detected, a barcode reader is used to read a barcode on a slide.

In a working embodiment of the apparatus, the transporter comprises an X-Y-Z transport mechanism, which can be an X-Y shuttle table carried on an elevator. A counterweight can be attached to the shuttle table by a cable. Either the counterweight can be driven by a lead screw and a stepping motor, or the slide tray can be driven by a lead screw and a stepping motor. In a more particular working embodiment, the cable suspends the counterweight substantially at its center of gravity and the cable also suspends the shuttle table substantially at its center of gravity, thereby reducing moments that could cause binding as they are moved. A sensor (such as an optical or magnetic sensor) on the elevator stepping motor (such as a drive encoder) and or one or more sensors on the workstations can be used for sensing a location of the elevator relative to a workstation in the plurality of workstations. Within one or more workstations, an overflow sensor (such as a thermistor) for detecting a fluid overflow condition can be included.

In a particular embodiment, the solvent exchanger can include a top surface nozzle that is directed to a top surface of a slide during at least a portion of a slide processing operation. It can also include a bottom surface nozzle directed towards a bottom surface of a slide during at least a portion of a slide processing operation. An inline mixer can further be included in the solvent exchanger, as well as one or more blow-off nozzles that can be used for removing and/or spreading solvents from the slides or over the slides, respectively. A metering pump can also be included so that a controlled amount of a reagent fluid is applied to a surface of a slide.

A working embodiment of the disclosed system also includes a cabinet and a powered exhaust for exhausting fumes from the cabinet. A radiant heater also is included where the radiant heater provides a substantially uniform heating profile across the slides held in the slide tray. A portal formed in a wall of the cabinet for loading and unloading slide trays also is provided in the working embodiment, and further, a de-humidifier is added to decrease humidity within the cabinet.

Any workstation included in the disclosed system can further include a pan forming a bottom wall thereof. The pan can further have a gravity drain formed therein and/or an overflow sensor attached thereto such as a thermistor for detecting an overflow condition in the pan.

In a particular embodiment of a slide tray according to the disclosure, individual slides are held in the slide tray spaced from one another in two rows, and, for example, held substantially horizontal. As such, a code reader in some embodiments is positioned to read codes on slides in one row of the slide tray as the slide tray and/or code reader are moved in one direction relative to one another, and the code reader is re-positioned to read codes on slides on the other row as the tray and/or bar code reader are moved in an opposite direction relative to one another.

Since it is desirable that individual slide positions can be accurately located by moving parts within a workstation in order that slide processing operations are performed precisely a workstation (such as a combined de-paraffinizer/stainer, a solvent exchanger, or a coverslipper) can receive a slide tray in substantially a single position. Therefore, a workstation can include a mechanism to hold a slide tray substantially in a single position, for example, one or more springs can be used to hold the slide tray substantially in the single position.

A workstation according to the disclosure (such as a solvent exchanger, a combined de-paraffinizer/stainer or a workstation that functions as a solvent exchanger, de-paraffinizer and stainer) can include one or more nozzles that dispense a reagent to a top and/or bottom surface of a slide held in a slide tray. In some embodiments, the one or more nozzles include one or more backward top surface rinse nozzles, one or more bottom surface rinse nozzles, one or more forward top surface rinse nozzles, one or more dispense nozzles, and one or more jet drain nozzles. The one or more backward top surface rinse nozzles and the one or more forward top surface rinse nozzle can be positioned to deliver a reagent to substantially the same area on a slide. The nozzles can be fixed in position within the workstation or can be moveable within the workstation such as on a moveable nozzle assembly. In particular embodiments, the backward top surface rinse nozzles and the forward top surface rinse nozzles are positioned to deliver the reagent at an angle between about 20 degrees and about 50 degrees relative to a top surface of a slide and between about 20 degrees and about 35 degrees relative to the top surface of the slide, respectively. An air jet or jets that can be used for mixing of reagents dispensed to a slide surface (see for example, U.S. Pat. No. 5,650,327, which is incorporated by reference herein), an air broom and/or a blow-off nozzle can be included in a workstation. For example, a moveable nozzle assembly can include one or more backward top surface rinse nozzles, one or more bottom surface rinse nozzles, one or more forward top surface rinse nozzles, one or more dispense nozzles, one or more jet drain nozzles, one or more air jets, one or more air brooms and/or one or more blow-off nozzles.

A coverslipper according to the disclosure can include a moveable coverslipping head, and the coverslipping head can further include an air broom. The coverslipping head also can further include one or more moveable pins that hold a coverslip in position on a slide while a hook attached to the head that is holding the coverslip is removed. In one embodiment, a coverslipper includes a moveable coverslipping head, wherein the coverslipping head comprises a coverslip gripper that includes a flexible backing plate and a sealing member connected to or integral with a bottom of the flexible backing plate; the coverslipper further comprising a vacuum source communicating with the gripper, and a mechanism for moving the coverslipping head between a source of coverslips and a dispense position where a coverslip is applied to a slide. A cassette for holding individual coverslips for pick-up by the gripper can further be included, and in particular embodiments, the cassette is keyed to prevent misloading in the apparatus. The coverslipper can also include an RFID antennae connected to an RFID tag reader (for example, located elsewhere in the system) and an RFID tag can be included on the cassette.

Slide processing operations performed by the disclosed system and consumables tracking within the system can be controlled by a computer, which can be physically a part of the system control module or connected to the system's control module from another location. In particular embodiments, the disclosed system can employ two or more distinct layers of computer/microcomputer electronics hardware (see, for example, FIG. 42).

In some embodiments of the disclosed system, for example, systems having a single combined de-paraffinizer/stainer, the system can process up to about 100 slides per hour. In other embodiments, such as in embodiments having two or three combined de-paraffinizer/stainers or two or three workstations configured to perform steps of de-paraffinization, solvent exchange and staining, the system can process 150 or 200 or more slides per hours, respectively. In some embodiments two or more drying ovens and two or more radiant heaters also are included in the system to increase throughput.

A particular working embodiment of the disclosed automated slide processing apparatus includes a slide tray holding a plurality of slides in a substantially horizontal position; a plurality of workstations arranged in a vertical stack where the plurality of workstations includes a barcode reader, a combined de-paraffinizer/stainer; a solvent exchanger; a drying oven and a coverslipper; a transporter, where the transporter includes an X-Y-Z mechanism, wherein the X-Y-Z mechanism includes an X-Y shuttle table and an elevator in an elevator space; a garage adjacent to the elevator space for storing the slide tray; a radiant heater located above an uppermost parking station in the garage; a cabinet enclosing the plurality of workstations, a dehumidifier for lowering humidity within the cabinet; and a portal through which the slide tray is introduced into or taken out of the apparatus. In a more particular working embodiment, the combined de-paraffinizer/stainer and the solvent exchanger dispense a reagent to slides in the slide tray without a substantial amount of the reagent that contacts a first slide contacting a second slide, thereby minimizing cross-contamination between slides.

In another aspect, the disclosure provide a fluidics module that can be included in the disclosed slide processing system where the fluidics module is configured to allow replenishment of reagent solutions in the system without interruption of workflow in the system. In one embodiment, the fluidics module includes one or more dual chamber reagent pumps, one or more dual chamber dilution and dispensing pumps, and/or one or more single chamber concentrate pumps. Disclosed pump configurations used in disclosed methods of operation can enable uninterrupted delivery of reagents to system workstations, even while reagents are being replenished in the system.

In another embodiment, two or more consumables used by the apparatus during operation are provided in separate packages, wherein the separate packages are keyed (such as color keyed, mechanically keyed, optically keyed and/or electronically keyed) to help prevent misloading of the packages into the apparatus. In addition, separate packages used in the system can include a code (such as an RFID tag) and the apparatus can further include code readers (such as an RFID reader and antennae) located adjacent installation locations of the packages. In a more particular embodiment, a reagent container is provided for containing a reagent (such as a biological stain) for use in a biological reaction apparatus such as the disclosed system. The disclosed container includes a casing having a bottom, sidewalls and a cover, and a collapsible bag compatible with a reagent to be contained therein, held within the casing. The collapsible bag includes a bottom, sidewalls and a top wall configured and dimensioned to substantially fill the casing when expanded (such as when filled with reagent to capacity). The collapsible bag also has a tube sealed to the top wall of the bag and extending into an interior of the bag. The top wall of the casing is keyed to mate with a corresponding key in the biological reaction apparatus. In particular embodiments, the collapsible bag is formed of a flexible polymer such as a laminated material, for example, a three layer laminate. In other particular embodiments, the tube is sealed to the top wall of the casing and typically one end of the tube extends to or near the bottom of the bag. A fitting can be attached to a distal end of the tube, which in particular embodiment includes an elastomeric seal. The elastomeric typically includes a thin material (or septum) that is easily punctured by insertion of a piercing tube mounted on the apparatus. The fitting can be fixedly located under or to the casing lid and the casing cover can include a cutout for providing access to the fitting. A removable sealing tape can be placed over the cutout. In more particular embodiments, the key can include a color code and/or an interference fit. A barcode and/or an RFID tag also can be affixed to an outer wall of the container to, for example, provide information about the contents of the container.

Another aspect of the disclosure is a method for automated processing of a plurality of biological samples on slides where the slides are held in substantially horizontal positions in a slide tray. In one embodiment, the biological samples comprise paraffin-embedded biological samples. The method includes moving the slide tray to a first workstation and automatically staining the samples in the first workstation and/or automatically de-paraffinizing the sample slides in the first workstation and/or automatically solvent exchanging the samples in the first workstation. The method can further include moving the slide tray to a position under a radiant heater and melting paraffin in the biological samples prior to moving the slide tray to the first workstation. Additionally, the method can include moving the slide tray to a second workstation and automatically solvent exchanging the samples through a series of two or more different solvents in the second workstation. The method can yet further include moving the slide tray to a coverslipper workstation and coverslipping the slides in the slide tray in the coverslipper workstation. An alternative embodiment of the method includes moving the slide tray to the first workstation, de-paraffinizing the samples in the first workstation, staining the samples in the first workstation and also solvent exchanging the samples through a series of two or more different solvents in the first workstation. In more particular embodiments, staining comprises H&E staining or Pap staining. In an even more particular embodiment, staining includes dispensing a hematoxylin solution and an eosin solution to the samples. In another even more particular embodiment, staining includes dispensing a hematoxylin solution, an Orange-G solution and an Eosin-azure solution to the samples. The method can further include rinsing the samples (one or more times with a solution or solvent such as a solution of a surfactant and/or buffer, an alcohol/water solution, or an alcohol solvent. The method also can further include bluing the samples.

III. Slide Processing System

A schematic diagram of one embodiment of the disclosed slide processing system is shown in FIG. 1. System 2 of this embodiment includes a plurality of workstations 4, 6, 8 and 10, a transporter 12, a fluid supply 14, a pneumatics module 16, a computer 18, and a second, optional bank of workstations 20. A slide tray bearing a plurality of slides (not shown) is carried by transporter 12 between the workstations, and the transporter and workstations are under the control of computer 18, which can be part of a larger laboratory information management system that can be connected, for example, to additional automated staining systems (see, for example, U.S. patent application Ser. No. 10/893,725, filed Jul. 16, 2004, and U.S. patent application Ser. No. 11/032, 324, filed Jan. 10, 2005, both of which applications are incorporated by reference herein). Workstations 4, 6, 8 and 10 can be present in any number and arranged in any configuration in relationship to each other. For example, the workstations can be arranged side-by-side in a horizontal configuration, in a vertical stack where the workstations are positioned substantially directly above and below one another, or in a sloped vertical stack where workstations can be side-by-side at any intermediate level in the sloped stack. Examples of workstations that can be included in the disclosed system include, but are not limited to, a radiant heater, a code reader, a stainer, a de-paraffinizer, a solvent exchanger, a coverslipper, a baking oven (radiant heat oven or convection oven), a combined baking oven and de-paraffinizer, a combined de-paraffinizer/stainer, a combined de-paraffinizer/stainer/solvent exchanger, and other types of workstations that can perform one or more slide processing operations (such as two or more) in a single workstation. As a tray of slides is processed by system 2, fluids are supplied to one or more of the workstations by fluid supply 14, and pneumatics (pressurized gas and vacuum) are supplied to one or more of the workstations by pneumatics module 16. Additional workstations 20 can be added to the system to provide any number of functionalities for processing slides.

In a particular embodiment of the system shown in FIG. 1, the slides are held in a substantially horizontal position in the slide tray that is moved from workstation to workstation by transporter 12. In a more particular embodiment, workstation 4 comprises a combined de-paraffinizer/stainer, workstation 6 comprises a solvent exchanger, workstation 8 comprises a slide tray drying oven and workstation 10 comprises a coverslipper. In yet another particular embodiment, the workstations are arranged in a vertical stack, and transporter 12 also comprises an elevator.

Figure 2:
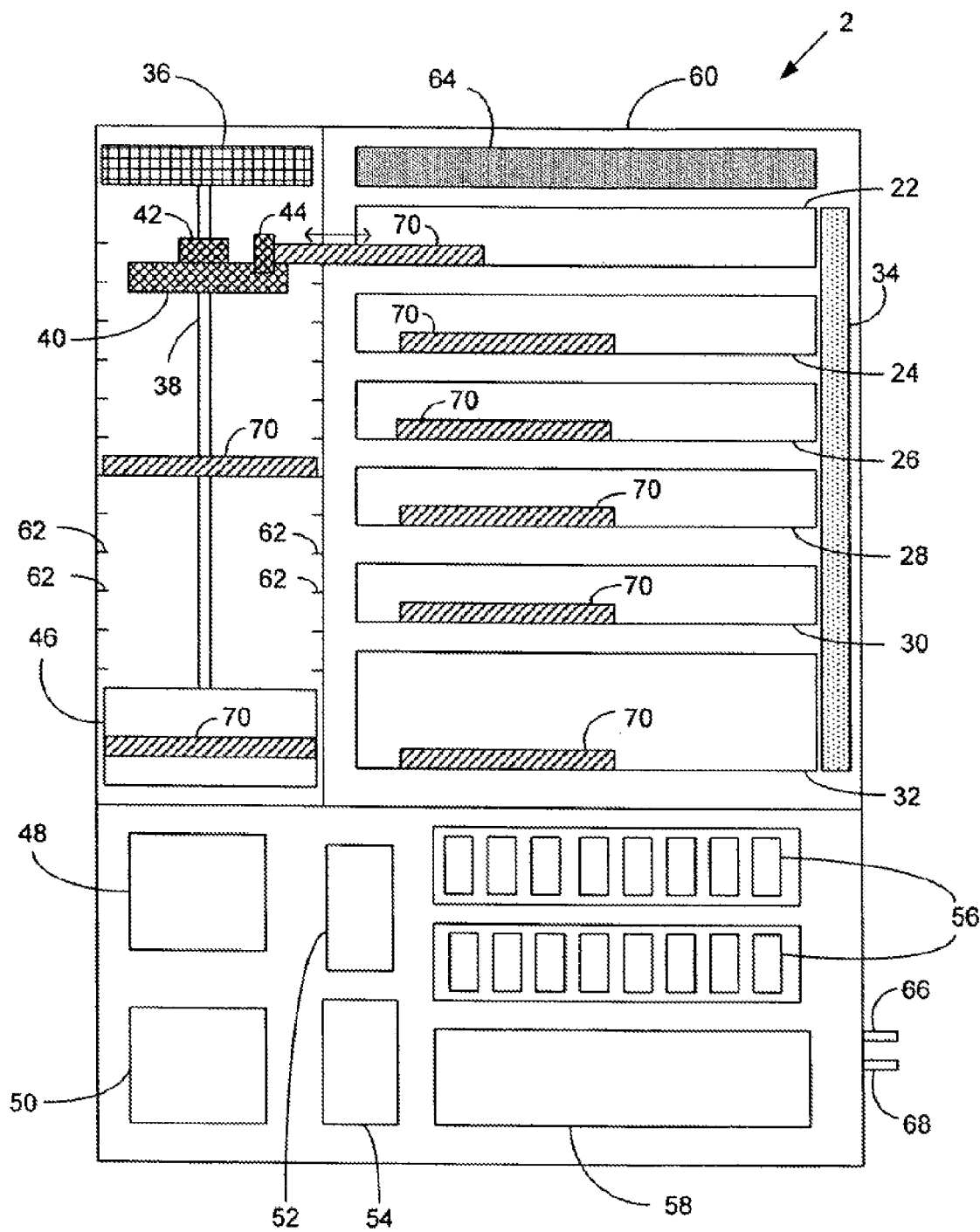
FIG. 2 is a schematic diagram of a working embodiment of the disclosed system.

A schematic diagram of another embodiment of system 2 is shown in FIG. 2. In this embodiment, the workstations include a code reader 22 (which is not required for system operation, but offers certain advantages for sample tracking), a combined de-paraffinizer/stainer 24, a second, optional de-paraffinizer/stainer 26, a solvent exchanger 28, a slide tray drying oven 30, and a coverslipper 32. One or more of the workstations (for example, the de-paraffinizer/stainer(s) 24, 26 and the solvent exchanger 28) are connected to fluidics manifold 34, which supplies reagents such as water, solvents (such as alcohol and limonene) and staining solutions (such as hematoxylin solutions and eosin solutions) to the workstations. An electronics manifold (not shown) links the workstations to control module 48 to provide power and control over the workstations. In a particular embodiment, individual workstations are connected to the fluidics manifold and the electrical manifold through common interfaces and plugs, respectively. The interchangeability afforded by using common interfaces and plugs makes it possible to add and remove workstations quickly and easily, thereby facilitating reconfiguration and repair of the system.

Additional components of the embodiment of FIG. 2 include radiant heater 36 that can be used to bake biological specimens onto microscope slides and to facilitate de-paraffinization of the sample as part of a disclosed method. In the particular embodiment illustrated in FIG. 2, radiant heater 36 is located above a garage 62 (see discussion below) that is adjacent to transporter/elevator 38. Transporter/elevator 38 includes tray table 40 that moves slide trays within the system, for example, in and out of the workstations, and in and out of user interface portal 46. Tray table 40 includes two tray sliders 42 and 44 that can engage and move a slide tray onto and off of tray table 40, either from side to side (44) or from front to back (42) within the system, and then release the tray once it is placed in a location off of the slide tray. User interface portal 46 can be of any design, but in a particular embodiment is selectively closed off by a power door hinged at a front wall such that it is inwardly swingable, and linked via a pivot arm and a cam follower to an electric motor or air valve (all not shown). The power door can be similar to a conventional video cassette recorder (VCR) loading and unloading door as is described, for example, in U.S. Pat. No. 5,917,675.

Control module 48 of FIG. 2 distributes electric power to system components and includes at least one microprocessor or microcontroller that controls one or more aspects of system operation. Pneumatics module 50 supplies pressurized air and vacuum for various slide processing operations and for moving fluids within the system. Bulk reagent containers 52 and 54, which can be filled by a user, provide reagents used in larger volumes by the system (for example, limonene and ethanol). Reagent containers 56 provide fluids and solutions that are used in smaller volumes by the system (such as dye solutions, for example, hematoxylin and eosin solutions). In a particular embodiment, reagent containers 56 are bag-in-a-box containers that can only be placed in particular positions in the system. Fluid movement into, out of, and within the system is controlled by fluidics module 58 that includes, for example, pumps and valves that supply reagents to system components.

Cabinet 60 of FIG. 2 includes a plurality of tray parking stations 62 located adjacent to the transporter, collectively referred to herein as a "garage." Tray parking stations 62 can be used to store trays before, during or after processing in one or more workstations. Also included within cabinet 60 is dehumidifier 64. A deionized water inlet 66 and a waste outlet 68 also are components of the working embodiment of FIG. 2. Slide trays 70 are shown in various positions (such as within individual workstations) in FIG. 2 to illustrate how a plurality of slide trays can be simultaneously processed in the workstations and stored in the system. For example, FIG. 2 shows a slide tray in user-interface portal 46, which is where slide trays are added to or removed from the system by a user. Another slide tray is shown partially inside of code reader 22 to illustrate one method by which slides in a slide tray are detected by sensors and/or codes on individual slides can be read by the code reader. Namely, the slide tray can be moved into and out of a workstation using the transporter such that sensors (such as optical reflective sensors) located on the partition between the workstation and the elevator space can detect the presence of slides in particular positions in the slide tray, and such information can be used by the system to apply reagents selectively to the positions where slides actually reside in a given slide tray. Furthermore, movement of the slide tray into and out of a code reader workstation permits the codes on the slides to pass the component of the code reader 22 that detects the codes (such as a bar code reader), thereby simplifying the code reader workstation by eliminating the need to move the code reading component of the workstation. Yet another slide tray is shown in a parking station 62 in the garage. In a particular embodiment, slide tray 70 holds a plurality of slides in a substantially horizontal position.

Figure 3:
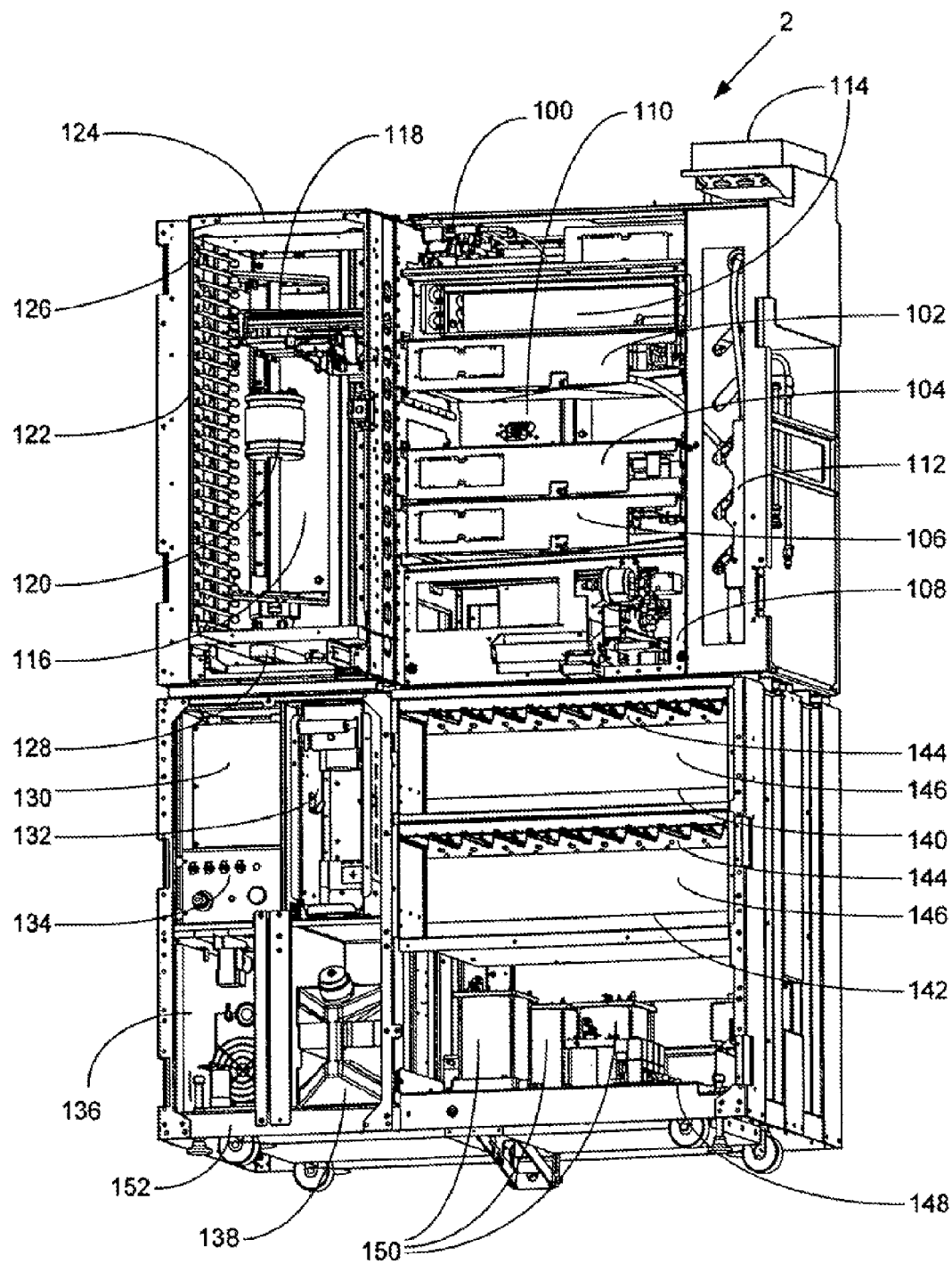
FIG. 3 is a perspective view showing a working embodiment of the disclosed system.

A perspective diagram of a working embodiment of the disclosed system is shown in FIG. 3. System 2 includes a vertical stack of workstations that includes, from top to bottom, bar code reader 100, combined de-paraffinizer/stainer 102, solvent exchanger 104, convection oven 106, and coverslipper 108. In this embodiment, the workstations are connected to electronics backplane 110 (which can be seen at the back of the workstation bay that is unoccupied and can provide power and a data link to a system's computer). Combined de-paraffinizer/stainer 102, solvent exchanger 104 and coverslipper 108 also are connected to waste drain 112, which is part of a fluidics manifold that supplies reagents to the workstations and drains spent reagents from the workstations. The workstations can be interchanged in position because in this embodiment, common connections are provided on the electrical and fluidic backplanes at several of the bays. Furthermore, this configuration permits rapid removal and replacement of individual workstations to aid reconfiguration (such as adding a second combined de-paraffinizer/stainer to increase system throughput potential) and repair (should a workstation fail or need scheduled maintenance). In other embodiments, one or more combined de-paraffinizer/stainers can be operated as combined de-paraffinizer/stainer/solvent exchangers and the solvent exchanger is not included. In such other embodiments, coverslipper 108 can further include heaters to assist in drying of slide trays by, for example, pre-heating the slide trays before they are transported to convection oven 106.

A dehumidifier 114 also is included in the embodiment of FIG. 3. The dehumidifier can lower humidity levels within the system to minimize moisture uptake by reagents and reduce condensation within the system. Adjacent to and to the left of the vertical stack of workstations is transporter/elevator assembly 116 that occupies an elevator space. As can be seen in the empty bay of the vertical workstation stack, access ports are provided through which slide trays can be shuttled from the elevator space to the individual workstations in the vertical stack. Transporter/elevator assembly 116 includes X-Y shuttle table 118, and the combination of the elevator and the shuttle table comprises a particular embodiment of an X-Y-Z transport mechanism (X—left to right; Y—front to back; Z—up and down). Although not shown in detail in FIG. 3, X-Y shuttle table 118 is suspended from a cable that is connected to counterweight 120. In a particular embodiment, counterweight 120 is raised and lowered by a drive screw, which in turn is driven by a stepper motor. Sensors (not shown) can be placed adjacent the elevator space to detect the position of the shuttle table, and indexing of the shuttle table at the sensor locations provides precise control over the elevator position using stepper motors.

Adjacent to and in front of the transporter/elevator assembly 118 in FIG. 3 is garage 122. Above garage 122 in this embodiment is radiant heater 124. The topmost parking station of the garage thus comprises a baking workstation 126. A slide tray can be placed in the baking station 126 underneath the radiant heater 124 to bake biological samples onto slides held in the slide tray. In a particular embodiment, radiant heater 124 has a heat profile that provides substantially uniform heating of the slides in the slide tray. Differences in heat generating power/unit area across radiant heater 124 compensate for differences in the distance of a particular slide from the edge of the slide tray. Otherwise, slides that are at the edge of the slide tray would not be heated to the same extent as slides near the middle of the tray due to greater heat loss rates for slides on the edges of the tray and the greater heating rates for slides in the middle of the tray. Located below garage 122 is portal assembly 128 through which slide trays can be introduced to and retrieved from the system.

Below both the garage, elevator/transporter assembly and the vertical stack of workstations in FIG. 3 are several components that provide power, control and reagents to the system. In particular, printed circuit board 130 including a microprocessor that controls, for example, supply of reagents to the workstations and workstation functions. Additional printed circuit boards including microprocessors (not shown) on individual workstations and the elevator/transporter assembly further control the system. Limonene supply unit 132 (shown without the removable limonene container) includes an RFID antenna and sensors for detecting a fluid level in a removable container. Power supply 134 and pneumatics supply 136 provide power and pressure/vacuum, respectively. A bulk alcohol supply 138 also is shown.

On the right side of the lower portion of the system shown in FIG. 3 are 3 drawers of components that together comprise a fluidics module for supplying reagents to the system. Each of these drawers can be slid out toward the front of the system to permit access to additional components at the back of the system that are hidden in the view of FIG. 3. Two reagent drawers, the upper reagent drawer 140 and the lower reagent drawer 142, each include reagent container slots 144 for holding a plurality of reagent containers (such as keyed "bag-in-a-box" containers discussed below) and a backpanel 146 that can include a plurality of RFID antennae that can read RFID tags associated with the reagent containers, which, for example, encode the identity and expiration date of a particular reagent. The upper reagent drawer 140 and the lower reagent drawer 142 also include pneumatic reagent pumps, valves and tubing (not shown) to supply reagents to one or more workstations in the vertical stack above. Below the two reagent drawers is fluidics drawer 148 that includes a plurality of pneumatic reagent pumps 150. The components of the system of FIG. 3 are contained in modular cabinet 152.

In operation, system 2 of FIG. 3 can simultaneously process several slide trays, each of which carries a plurality of slides (such as a plurality of slides held in a substantially horizontal position). A user loads a slide tray into the system through portal assembly 128. Elevator/transporter then retrieves the slide tray from the portal assembly 128. Once the slide tray is pulled from the portal assembly 128 onto X-Y shuttle table 118, the slide tray can be moved to any of the workstations or placed in a parking station of the garage to await retrieval at another time.

Although a particular slide tray can be processed according to any arbitrary user-defined or pre-defined set of operations, a particular sequence of operations includes first taking a slide tray to barcode reader 100 where slides in the tray are detected by optical sensors on a partition between the transporter space and the code reader and any barcodes on detected slides are read by the code reader. The slide tray is then moved to baking station 126 where biological samples on the slides are heated under radiant heater 124. The baking step can be used, for example, to adhere the samples to the slides and/or to melt an embedding material in the sample. It has been surprisingly discovered that baking the slides under radiant heater 124 greatly aids removal of paraffin from paraffin-embedded tissue samples, as it tends to melt and spread the paraffin in the sample across the surface of the slide. The thin layer of paraffin, having greater surface area now that it has spread across the slide, is more easily removed by a paraffin-dissolving solvent such as limonene, making it possible to remove the paraffin with the solvent, without either heating the solvent before it is applied to the slide or after it has been applied to the slide. Once the slides have been baked, the slide tray is moved to combined de-paraffinizer/stainer 102 where the biological samples on the slides in the slide tray are de-paraffinized if necessary and stained. Since many staining protocols make use of aqueous-based solvents, and cover-slipping of a sample is best accomplished once water in the sample has been removed, the slide tray is then moved to solvent exchanger 104 where the sample is treated with a series of solvents to remove water and prepare the slides for coverslipping. In an alternative embodiment, solvent exchange also is performed in workstation 102, which can function to de-paraffinize, stain and solvent exchange samples.

It also has been surprisingly discovered that it is possible to apply a controlled amount of a solvent that is compatible with coverslipping (such as limonene) in solvent exchanger 104 and use that solvent in a coverslipping operation once the slide tray has been moved to coverslipper 108, thereby reducing system complexity in a particular embodiment since the coverslipper 108 can be operated without the need to supply it with fluids. Thus, in this particular embodiment, the slide tray is moved from solvent exchanger 104 (with an amount of a coverslipping compatible solvent on its top surface) to coverslipper 108. Once coverslips are placed onto the slides in coverslipper 108, the slide tray can then be moved to convection oven 106 to cure the coverslip onto the slides (at least partially) and also to dry the tray itself (at least partially). A particular advantage of a disclosed system and a method in which slides are cured in an oven after coverslipping (for example, either a convection oven or a radiant oven) is that even if the coverslipping solvent underneath the coverslip is not completely removed, a skin of glue forms around the coverslip, which holds the coverslip in place during subsequent handling by a health care professional such as a pathologist. Processing slides held in a substantially horizontal position aids curing since the large exposed surface area of the slides facilitates quick and efficient removal of solvents from slide surfaces. Once the slides are cured and the tray dried, the slide tray can be moved back to portal assembly 128 for retrieval by a user. Parking garage 122 can be used to store slide trays at any point during the series of slide processing operations, and as is described below, computer control of the sequence of movements/operations can maximize workflow by helping to ensure that workstations are not idle because no slide tray is available for processing therein.

Figure 4A:
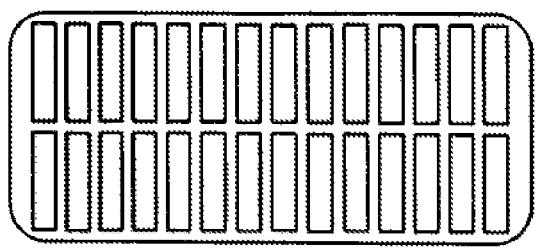
FIGS. 4 A-F are a series of schematic drawings showing several different slide tray arrangements that can be used in the disclosed system.
Figure 4B:
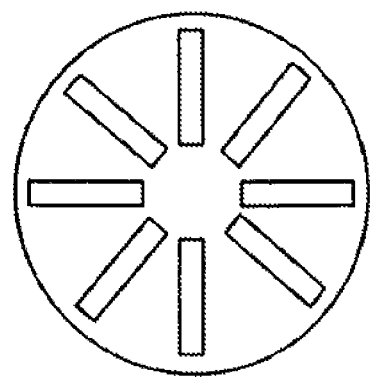
Figure 4C:
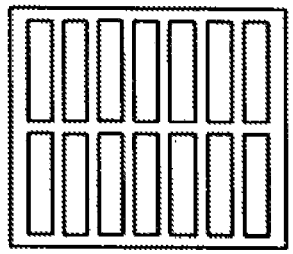
Figure 4D:
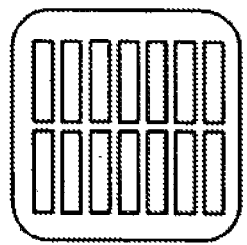
Figure 4E:
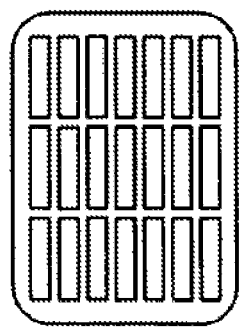
Figure 4F:
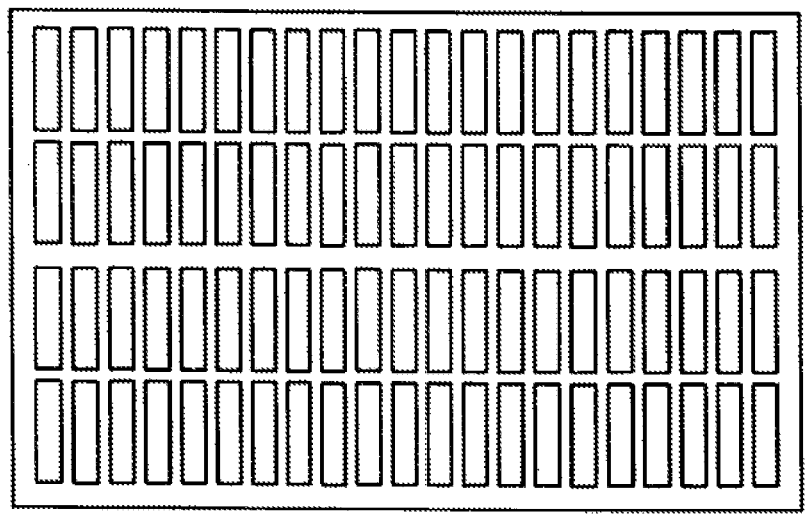

As described previously, a plurality of slides can be held (such as in substantially horizontal positions) in a slide tray. The slide tray may have any shape, and the slides held in a slide tray can be arranged in any manner. In addition, the slide tray can be configured to hold any number of slides, for example, 5 or more slides, 10 or more slides, 20 or more slides, or even 30 or more slides. Several examples of slide trays of different shapes, holding slides in various arrangements, are shown in top view in FIGS. 4A through 4F. FIG. 4A shows a rectangular tray holding two rows of slides that are held side-by-side on both sides of the central long axis of the slide tray so that the long dimensions of the slides are disposed outward from the long central axis of the tray. FIG. 4B shows a circular slide tray with slides held in radial positions with their long dimensions disposed inward from the outer edge of the tray toward the center of the tray. FIG. 4C shows another rectangular tray holding two rows of slides that are held side-by-side on both sides of the central long axis of the slide tray. FIG. 4D shows a square tray holding two rows of slides. FIG. 4E shows a rectangular tray holding three rows of slides, where slides are held such that their long dimensions are parallel to the long axis of the tray. FIG. 4F shows a larger, rectangular tray holding 4 rows of trays, with the slides held side-by-side in the four rows such that the long dimensions of the slides are disposed in the direction of the short axis of the tray.

IV. System Components/System Operation

A. Slide Tray

Figure 5:
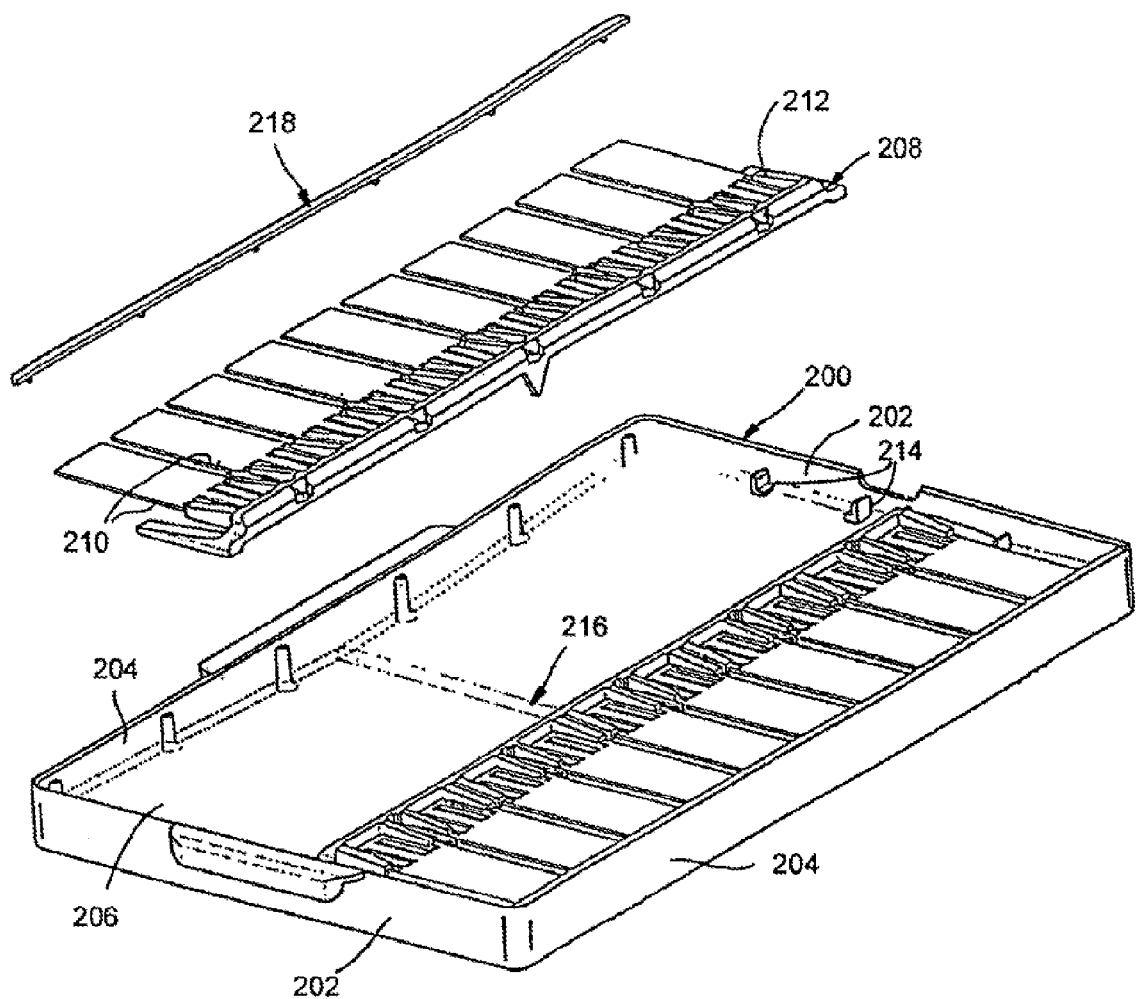
FIG. 5 is a perspective view showing an embodiment of a slide tray holding slides in a substantially horizontal position.

A particular embodiment of a slide tray that can be used in the disclosed system is shown in FIG. 5. Rectangular slide tray 200 having side walls 202, 204 and bottom 206 includes a specimen slide supporting rack 208 for holding a plurality of specimen slides 210 in a substantially horizontal position in the same plane. Holding all the slides in separation and in essentially the same substantially horizontal plane facilitates baking and drying can prevent cross-contamination of slides during de-paraffinizing, staining, washing and solvent exchanging, and other steps that involve dispensing reagents to slide surfaces. Rack 208 includes a plurality of slide spring supports 212 that limit the axial, lateral and vertical movement of specimen slides 210 once placed on the slide tray. Rack 208 snaps into tabs 214 and is supported above tray bottom 206 at sufficient height to minimize or prevent the formation of films or bubbles between the specimen slide bottom and the tray bottom. Slide spring supports 212 hold the individual specimen slides in position by exerting force on opposing sides of the specimen slides 210. The floor 206 of the slide tray is sloped towards nadir 216 in the middle of the tray. Spent reagents dispensed to slides that accumulate in nadir 216 can then be aspirated from the tray as will be described in detail below with reference to the description of particular embodiments of the system's workstations. Optional splash guard 218 can be added to further inhibit transfer of reagent from one slide to another. Tray 200 can be used for automated handling of a plurality of specimen slides through of the steps of drying/baking, de-paraffinizing, staining and coverslipping using workstations configured to treat the slides as they are held in the tray's particular configuration. In the embodiment of FIG. 5, slide tray 200 is configured to accommodate 16 specimen slides arranged in a generally horizontal grid of two rows of slides, each of which rows contain eight slides.

Figure 6:
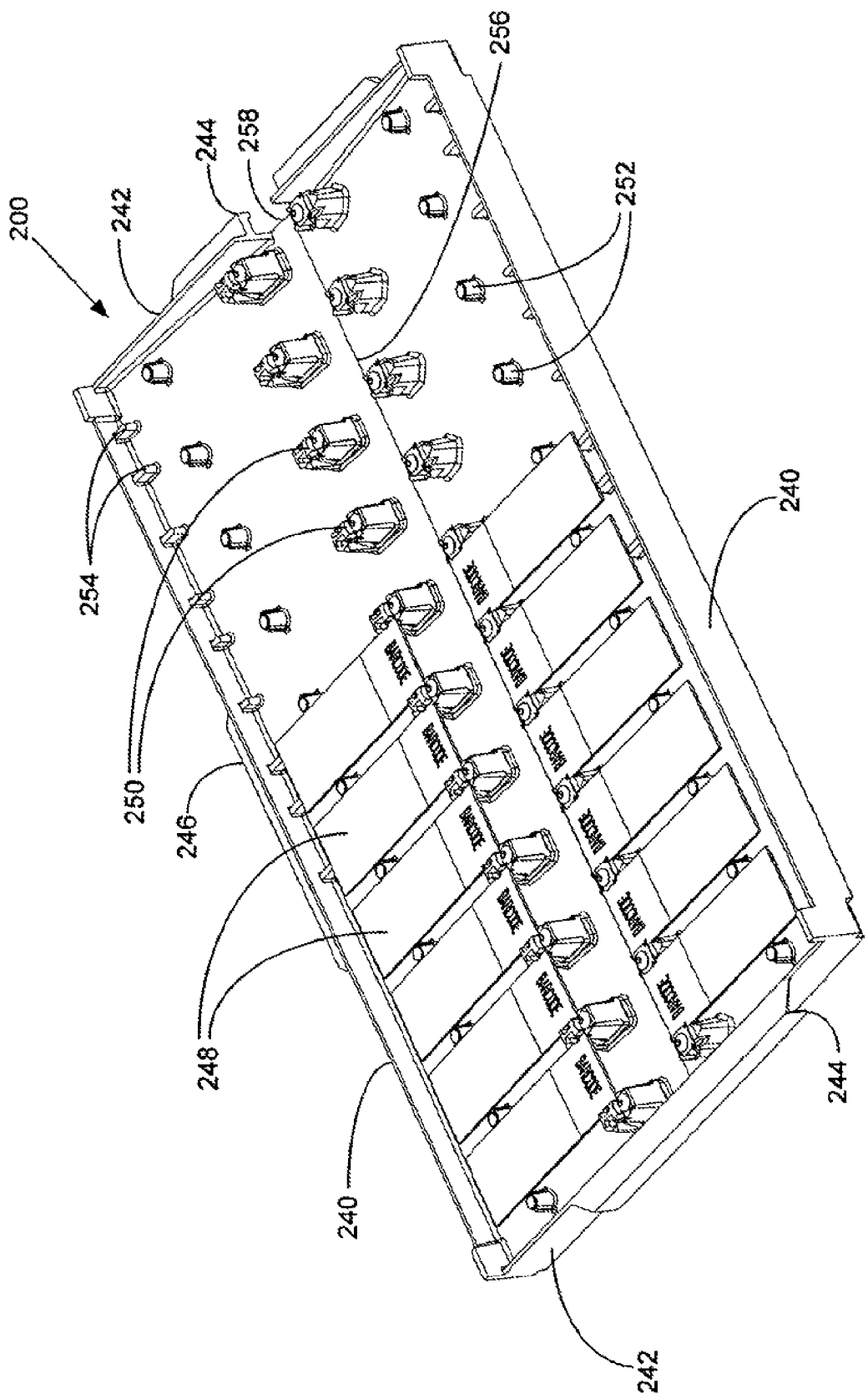
FIG. 6 is a perspective view showing another embodiment of a slide tray holding slides in a substantially horizontal position.

A second embodiment of slide tray 200 is shown in top perspective view in FIG. 6. In this embodiment, the rectangular slide tray having side walls 240 and end walls 242 further includes end hooks 244 and side hook 246 that can be engaged by a transporter as the slide tray is moved within the disclosed system. Slides 248 are held in the tray by slide clip pillars 250 and supported by slide support pillars 252. Optional slide end support tabs 254 also are shown in FIG. 6. Bottom 256 slopes from side walls 240 toward the center of the tray. An opening 258 in one end wall 242 is provided, and it is at this opening that a wicking member can contact the bottom 256 to break the surface tension of any liquids collected in the slide tray, thereby facilitating drainage of such liquids from the slide tray, especially if the slide tray is tipped in the direction of opening 258. In a particular embodiment, slides 248 are held substantially horizontal in the tray (when the tray itself is placed on a horizontal surface), and in more particular embodiments, the slides slope slightly downward (decline) from the slide clip pillars 250 to slide support pillars 252, for example, at an angle between about 0.2 degrees and 0.8 degrees from horizontal, such as angles between about 0.3 degrees and about 0.7 degrees, for example angles between about 0.4 degrees and about 0.6 degrees. A small angle of decline toward the sides of the tray is surprisingly helpful for removal of reagents from the slide surfaces during certain slide processing operations, yet does not prevent substantially even distribution of reagents across the slides upper surfaces. The side and end walls of a tray can rise to a level below the level of slides placed in the tray, can rise to the same level as slides placed in the tray or can rise above the level of slides held in the tray. Side and end walls that rise above the level of slides held in the tray can have the advantage of reducing splashing of reagents over the sides of the tray, and can eliminate the need for additional splash guards within a workstation, such as the optional splashguards discussed below with respect to the nozzle manifold of FIG. 14.

Figure 7:
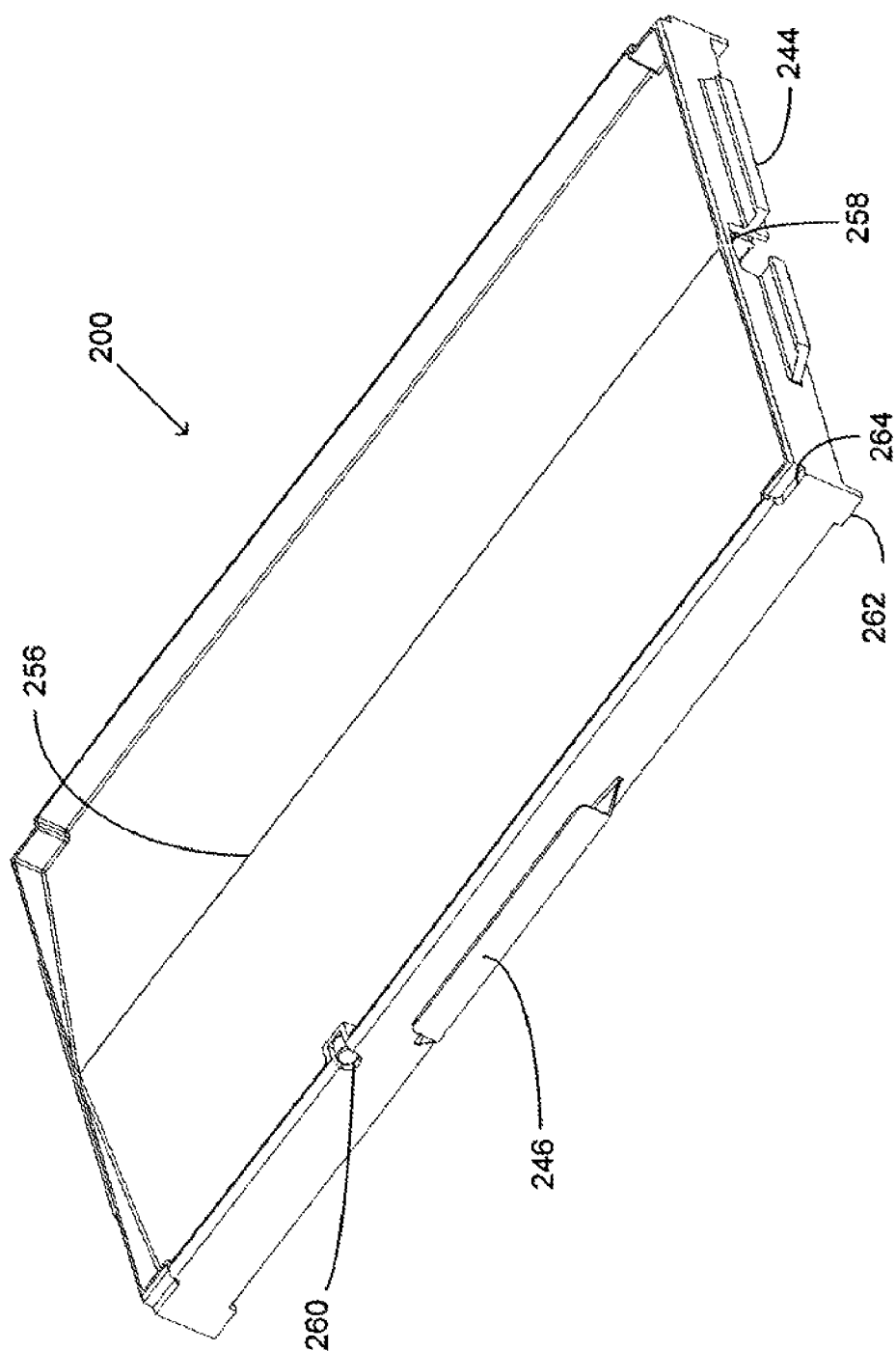
FIG. 7 is a perspective view showing the bottom of the slide tray of FIG. 6.

A bottom perspective view of the slide tray of FIG. 6 is shown in FIG. 7 to illustrate further the features of this particular embodiment of slide tray 200. The slope of bottom 256 toward the center midline of the slide tray is clearly visible in FIG. 7. An end hook 244 and side hook 246 also are shown. Additional features of slide tray 200 not shown in FIG. 6 include magnet 260 that can be used in conjunction with one or more Hall-effect sensors placed in one or more locations (such as in one or more workstations) in the disclosed system to detect when the slide tray occupies those locations. Tabs 262 and indents 264 at the corners (not all shown) of the tray can be used to stack several trays on top of one another without the slides touching so trays can be stored without taking up more laboratory bench space than necessary. Slide tray 200 can be constructed of any material including a metal (such as aluminum, magnesium or a lightweight metal alloy) or a plastic (such as ABS or a thermoplastic), and can be formed, for example, by machining, casting or molding. In a particular embodiment, lightweight slide trays are cast in magnesium and then covered with a tetrafluoroethylene, non-stick coating. Slide clip pillars 250, slide support pillars 252 and slide support tabs 254 can be formed at the same time as the tray (such as when the tray is cast) or added later, for example, by being glued into place.

FIG. 8 shows several different embodiments of slide clip pillar 250 and a close-up of a particular embodiment of a slide support pillar 252. FIG. 8A shows a slide clip pillar 250 having a spring clip 270 that is held to the slide clip pillar with screw 274. As was shown in FIG. 6, each slide is supported at one end by two slide clip pillars, one on each side of the slide. Spring clip 270 holds one edge of a slide against a slide support shelf 272. Slides are loaded into the tray by sliding them from the side of the tray and under the spring clips on adjacent slide clip pillars. The alternative embodiment of slide clip pillar 270 shown in FIG. 8B is a type of slide clip pillar that can be top-loaded by a user. In this alternative embodiment, a slide is pushed past the upper end of spring clip 270 to rest on slide support shelves 272 and is held there by the spring clip. Again, the spring clip 270 is held to the pillar with a screw 274. Another embodiment of a spring clip pillar 250 that is side-loaded by a user is shown in FIG. 8C. In this particular embodiment, the slide clip 270 includes a rigid top portion 276 and a flexible lower portion 278, where the slide clip is again held in place on the pillar by screw 274. As a slide is introduced into the slide clip 270, flexible lower portion 278 deflects toward spring clip support 273. Spring tension holds the slide firmly under the rigid top portion 276. Another embodiment of a side-loading slide clip pillar having a slide clip 270 with a rigid top portion 276 and a flexible lower portion 278 is shown in FIG. 8D. In this embodiment, as a slide is introduced, flexible lower portion again is deformed, but the deflection is not limited by contact with spring clip support 273 as in the previous embodiment. Spring tension holds the slide firmly under rigid top portion 276. A screw 274 can be used to secure the clip to the pillar portion. FIG. 8D also shows that a rigid top portion 276 can have an upward bend in the direction from which a slide is introduced into the clip that directs a slide toward the flexible lower portion 278, thereby aiding in deflection and loading of spring tension in the clip.

A close-up of slide support pillar 252 is shown in FIG. 8E. Slide 248 rests on support surface 280. The distance from the support surface to the top of the pillar can be made such that the top surface of slide 248 is above (as shown) and not in direct contact with slide support pillar 252. This arrangement is advantageous as it helps prevent wicking of reagents from the top surface of the slide. Again, as was shown in FIG. 6, each slide is supported by two such slide support pillars, one on either side of the slide. In another embodiment that is not illustrated, a single slide support pillar can be placed under the slide with the same advantage that it does not create a wicking path from the top surface of the slide. Additional embodiments of slide trays that can be used in the disclosed system are described in U.S. patent application Ser. No. 10/621,761, filed Jul. 16, 2003, which is incorporated by reference herein.

B. Drying Oven

Figure 9A:
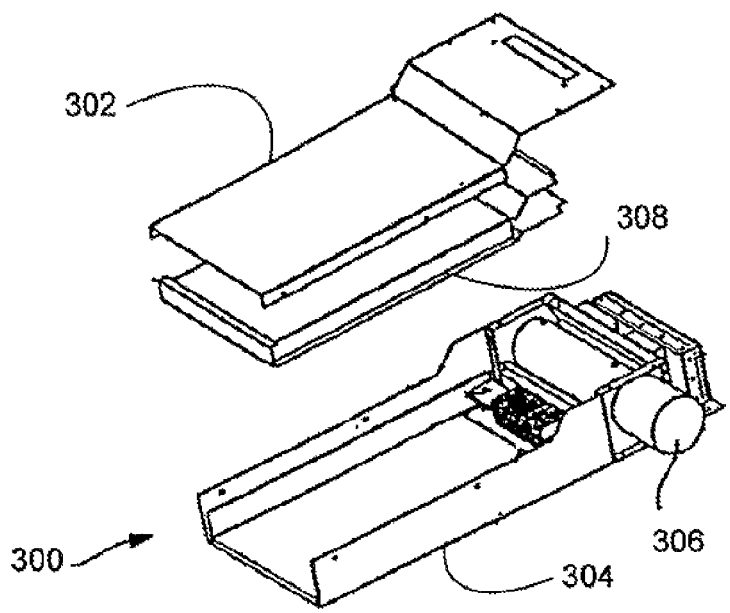
FIGS. 9 A-B are a pair of perspective views showing two different embodiments of a drying oven workstation that can be included in the disclosed system.

A drying oven, which includes a thermally insulated compartment and a heat source, can be used to cure slides after coverslipping (to set the coverslips in place and thus prevent their inadvertent removal during slide handling by a user) and to dry slide trays before they are retrieved from the disclosed system by a user. In one embodiment, as shown in FIG. 9A, drying oven 300 includes a top portion 302 and a bottom portion 304 that form a compartment that receives a slide tray. A convection heat source 306 (including one or more heating elements and one or more blowers) configured to blow heated air across the slides is located at the back of the slide tray receiving compartment. An insulating layer 308 can be included to reduce heat loss from the drying oven workstation, thereby increasing its thermal efficiency.

A second embodiment of the drying oven 300 is shown in FIG. 9B, and again includes a top portion 302 and a bottom portion 304 that together form a compartment that receives a slide tray. In this embodiment, the convection heat source is positioned above the slide tray compartment rather than at the back of the workstation as in the embodiment of FIG. 9A. The convection heat source includes blower 309, heat directing shield 310 (configured to circulate heated air evenly across the slides in a slide tray) and heating element 312. A slide tray tilt pan assembly 314 receives the slide in the compartment of the drying oven and can hold the slide tray firmly in position, for example, with one or more springs that grip the side of a slide tray as it is pushed into the drying oven by a transporter. In a particular embodiment, slide tray tilt pan assembly 314 includes a wicking member (not shown in full view) that contacts an edge of the bottom of a slide tray at an opening in an end wall and a tilting mechanism (not shown) that tilts the tilt pan assembly to drain the slide tray toward the rear of the workstation. Draining of a slide tray reduces the fluid volume that must be evaporated by the workstation. Thus, a pan 316 is provided to accept any liquids such as residual reagents that are drained from a slide tray as it is tipped in the workstation. The pan can include a drain tube (not shown) to carry liquids away from the workstation, and a overflow condition sensor 318 such as a thermistor to detect an overflow condition in the workstation that could occur, for example, if the drain tube became clogged. In addition, drying oven 300 can further include a sensor, such as an optical or Hall-effect sensor, that detects the presence of a tray in the workstation. One advantage of a horizontal presentation of slides in a slide tray is that convection drying is particularly efficient since liquids tend to spread across slides, and the greater surface area of the liquid aids in its evaporation. A heat sensor also can be included and used in a feedback control loop with the heating element to maintain a particular temperature within the drying oven, for example, to prevent excessive heating of the slides that could damage the biological specimens that they carry.

Figure 9B:
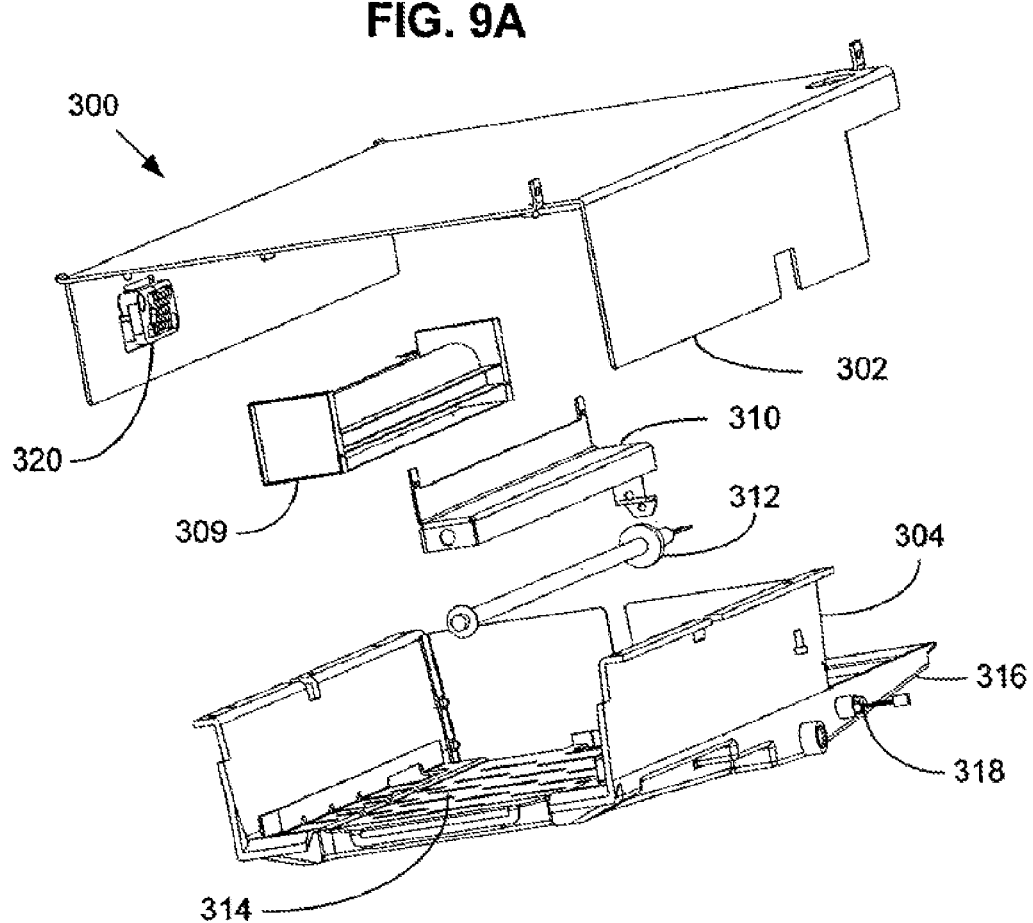

As was discussed with respect to FIGS. 2 and 3, the workstations of the disclosed system can include standardized data and power plugs that mate with corresponding plugs on an electronics manifold so that individual workstations can be interchanged in position within the system. Such a standardized power and data plug 320 is shown in the embodiment of FIG. 9B. In some embodiments, a convection drying oven can also function as a baking station for slides in an initial baking operation in a set of automated slide processing operations.

C. De-paraffinizer/Combined Baking Oven and De-paraffinizer

Figure 10:
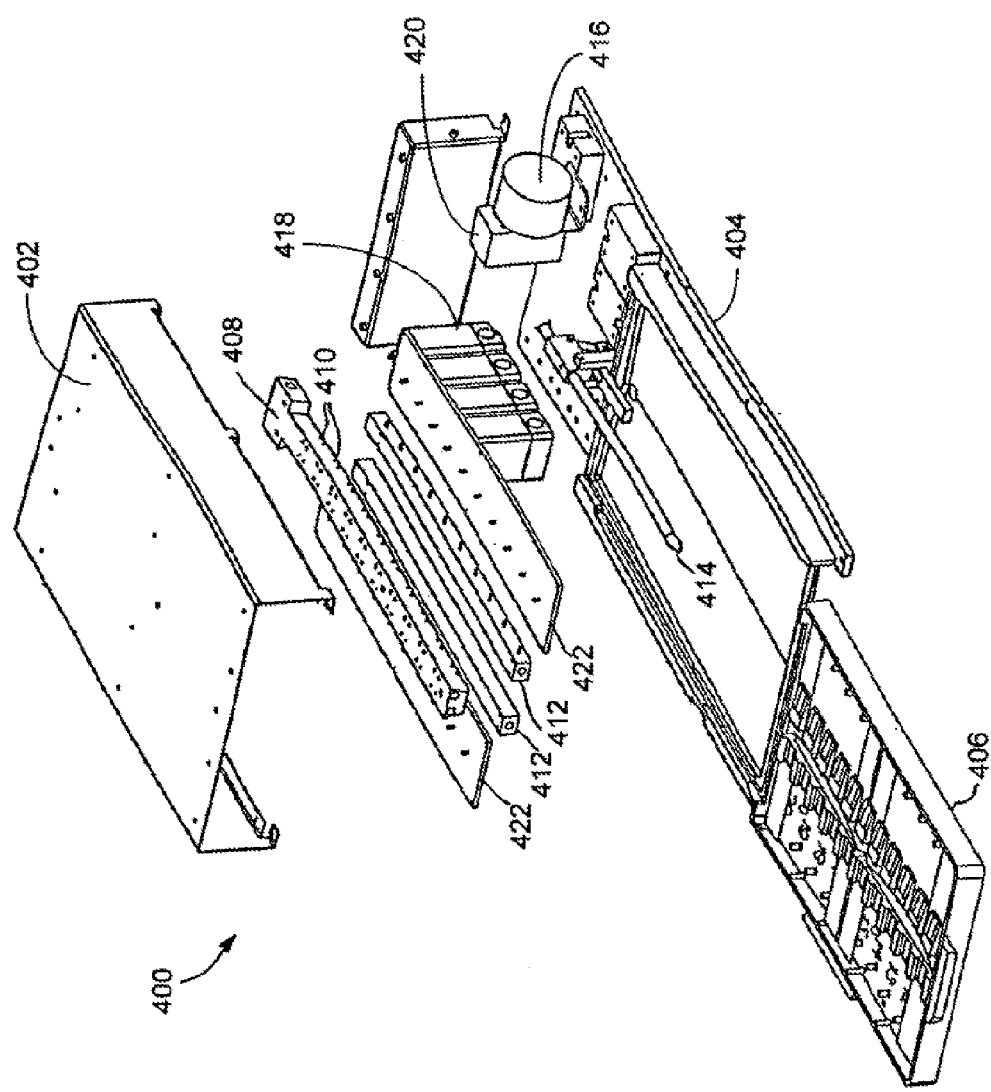
FIG. 10 is a perspective view showing an embodiment of a de-paraffinizer workstation that can be included in the disclosed system.

FIG. 10 shows a particular embodiment of a de-paraffinizer workstation that can be optionally configured to also function as a baking station, for example, to aid in de-paraffinizing biological specimens on slides. De-paraffinizing station 400 comprises a compartment having a top portion 402 and a bottom portion 404 into which a slide tray 406 holding a plurality of slides can be received, and within which one or more slide processing operations can be performed. In this embodiment, dispense manifold 408 having a plurality of dispense nozzles 410 is positioned above a slide tray docked in the workstation. The dispense nozzles 410 are configured to dispense reagents onto and along the top surfaces of the slides toward the sides of the slide tray, thereby minimizing the potential that reagent reaching one slide will thereafter contact another slide. Dual rinse manifolds 412 including rinse nozzles positioned to dispense another reagent such as deionized water also are included in the illustrated embodiment. In operation, a de-paraffinizing reagent is dispensed to the slides in the slide tray, and collects in the bottom of slide tray 406. Aspirator 414 can be positioned to remove the accumulating reagent from the slide tray.

In a particular optional embodiment, aspirated de-paraffinizing reagent is re-circulated by pump 416 and heated in heaters 418 before it is again dispensed from the dispense nozzles 410 in manifold 408. Filter 420 can be used to remove any cells that might become dislodged from the biological specimens on the slides before the reagent is reapplied to the slides, thereby minimizing the potential for cross-contamination of slides. It should be understood, however, that the use of fresh reagent each time a reagent is applied to a slide is the optimal approach.

In a more particular embodiment, optional radiant heater banks 422 also are included in the workstation, and these heater banks can be used to heat up the slides that rest below them when a slide tray is docked in the workstation. As such, the workstation becomes a combined de-paraffinizer and baking station. As mentioned previously, a baking station can melt and spread paraffin in a biological sample over a greater surface area, thereby facilitating its removal. The radiant heater banks 422 can be used alone, or in combination with recirculation and heating in heaters 418. If desired, accumulated paraffin in the reagent stream can be removed from the re-circulating fluid, for example, by skimming the paraffin from the top or bottom of the fluid, depending upon whether the de-paraffinizing reagent is more or less dense, respectively, than the liquefied paraffin.

Pre-heating the slides, i.e., to soften the paraffin, improves the efficiency of the de-paraffinizing step. Depending on ambient conditions and the amount and type of wax, it may be sufficient to apply the de-paraffinizing fluid to the pre-heated slides, let the fluid work for a few seconds or minutes, and then wash the fluid and wax from the slides using, for example, deionized water dispensed from rinse nozzles 412. If necessary, the de-paraffinizing fluid covered slides can be baked for several minutes or more, for example, about 5 minutes, before being washed. Thus, the de-paraffinizing process is enhanced. Moreover, less de-paraffinizing fluid can be used, and it may not be necessary to filter and recycle de-paraffinizing fluid. Rather, the spent de-paraffinizing fluid may be passed directly to drain, or filtered, and then passed to drain.

Various de-paraffinizing agents can be used in the workstation, and can comprise, for example, aqueous-based fluids such as disclosed in U.S. Pat. Nos. 6,544,798 and 6,855,559 (both of which are incorporated by reference herein), including deionized water, citrate buffer (pH 6.0-8.0), tris-HCl buffer (pH 6-10), phosphate buffer (pH 6.0-8.0), FSC buffer, APK Wash™, acidic buffers or solutions (pH 1-6.9), and basic buffers or solutions (pH 7.1-14). If desired, the aqueous-based fluid may also contain one or more ionic or non-ionic surfactants such as Triton X-100™, Tween™, Brij, Saponin and Sodium Dodecylsulfate. The de-paraffinizing fluid can be heated, however this is optional, especially if radiant heaters 422 are included in the workstation and employed in the de-paraffinization process. For example, if the embedding medium is paraffin, which has a melting point between 50-57 degrees C., the fluid can be heated to a temperature greater than the melting point of paraffin, e.g. between 60-70 degrees C. Typically, the fluid is heated in the fluid supply. The use of heated aqueous de-paraffinization fluids is described in more detail in U.S. Pat. No. 6,544,798, which is incorporated by reference herein.

Alternatively, any non-aqueous de-paraffinizing fluid such as limonene, xylene or an alkane-based fluid (such as an n-alkane or isoalkane, or a mixture thereof; see, for example, U.S. Provisional Patent Application No. 60/640,477, filed Dec. 30, 2004, which is incorporated by reference herein), or a combination thereof, can be used. While conventional de-paraffinizing fluid such as xylene may be used, one particular de-paraffinizing fluid that has been used in a working embodiment of the disclosed system is D-Limonene, which is a hydrocarbon of the monoterpene group having a molecular formula $C_{10}H_{16}$. D-Limonene, which has been used in the food and cosmetic industry for many years is non-toxic, and has become a preferred replacement for xylene in pathology laboratories. D-Limonene is commercially available from a variety of sources under various names including Safsolvent (Ajax Chemicals, Auburn, NSW, Australia), Hemo-De (PMP Medical Industries, Los Angeles, Calif.), Histo-clear (National Diagnostics, Manville, N.J.), BDH xylene substitute (BDH Chemicals Ltd., Toronto, Ontario, Canada), and AmeriClear (Baxter Health Care Diagnostics Inc., McGraw Park, Ill.). D-Limonene performs well as a paraffin solvent and cleaning agent, and also may present a reduced fire risk compared to xylene.

D. Radiant Heater/Baking Station

As discussed previously, a radiant heater can be used to bake biological specimens onto slides and/or to soften and spread paraffin in paraffin-embedded tissue specimens as an aid to paraffin removal. Although a baking station can be located anywhere in the disclosed system (for example, as a discrete workstation in a vertical stack of workstations) in the particular embodiments of FIGS. 2 and 3, a radiant heater is placed above the uppermost parking station in the garage portion of the system, and this parking station thus functions as the baking station. If the baking station is located in the garage adjacent to the code reader, it helps to minimize handling of the tray by the transporter and also helps to minimize the amount of moisture that accumulates in the system as water is driven off of biological specimens. Temperature in a baking station can be controlled by measuring the temperature with a temperature probe such as a thermocouple, which can provide feedback control of the amount of heat generated by the radiant heater.

In a more particular embodiment, the radiant heater is configured to provide substantially uniform heating of slides held in a slide tray. A general method by which the heating profile of a radiant heater can be configured is discussed below using the particular example of a rectangular slide tray holding a plurality of slides in a substantially horizontal position.

Figure 11A:
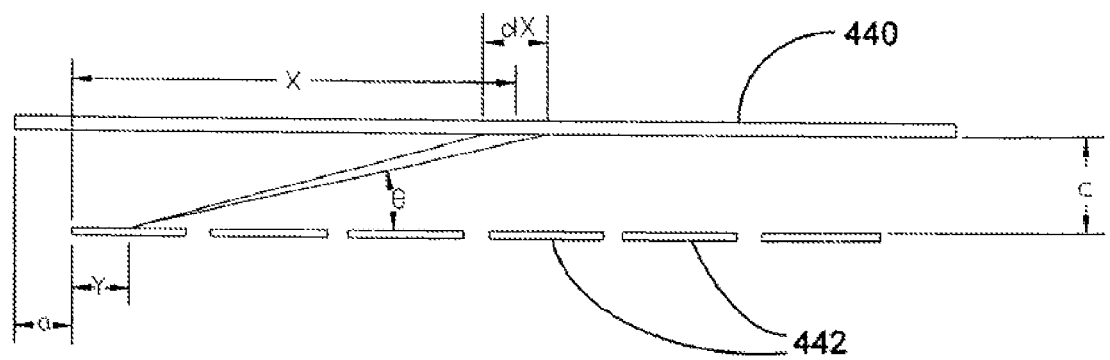
FIGS. 11 A-B are diagrams showing geometric considerations used to determine a heat profile for a radiant heater that heats slides in a slide tray substantially uniformly, and a perspective view showing a heat profile that can be configured into a radiant heater to provide substantially uniform heating of slides in a rectangular slide tray such as the slide tray of FIG. 6.

In general, in order to radiantly heat a tray full of slides substantially uniformly with a radiant heater of finite size, the temperature of the radiant heater needs to be hotter around the edges than in the center since heat loss from the edges of the heater occurs at a higher rate than in the center of the radiant heater, and because the slides in the center get heat from both sides while the slides near the edges get heat only from one side. FIG. 11A illustrates relevant parameters used to determine a heat profile of a radiant heater 440 that will heat slides 442 in a substantially uniform manner.

Advantageously the heater is sized to overlap the outer edges of the slides as far as possible, in this case by amount "a". The heater plate is displaced by distance "c" above the slides. A temperature distribution as a function of X along the heater plate that produces uniform radiant heat flux as a function of Y is desired.

The effective area of a narrow strip on the slide, dY, as seen from X is dY cos(θ), therefore, the radiant heat energy falling on a slide at Y on a strip of width dY from a strip at X on the heater of dX width is:

$$dq = I dX r d\theta \cos(\theta)$$

where dq=energy falling on strip dY wide emanating from dX, I=intensity of radiation (and I=k $T^4$), where T is the absolute temperature in Kelvins.

From geometry this can be reduced to:

$$dq = kT^4 dX dY c^2/[(X-Y)^2 + c^2]$$

For a fixed value of Y on the slide, dq(Y) is calculated as an integral over all X on the heater (from −a to X max).

$$dq(Y) = k \int_{-a}^{X_{max}} T_x^4 [c^2 / \{(Y-X) + c^2\}] dX$$

Figure 11B:
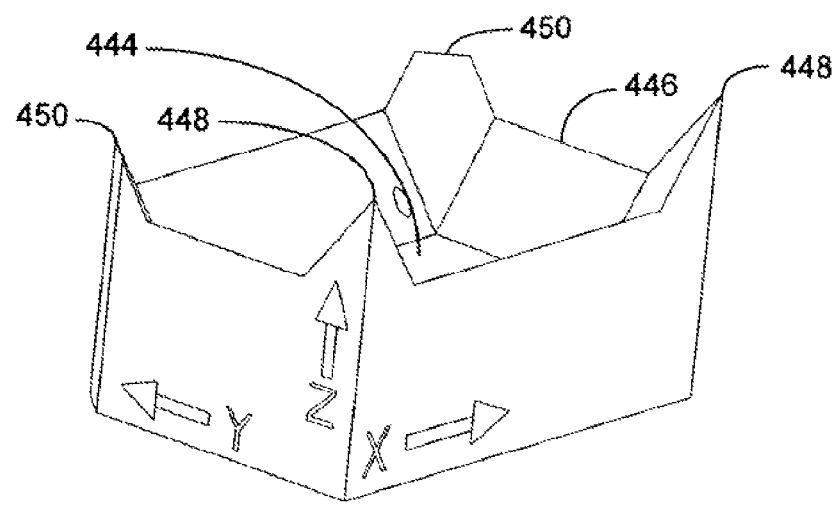

A distribution of $T_x$ such that dq(Y) is the same for all Y is desired, i.e., the amount of heat impinging on any part of any slide should be substantially the same. A solution can be found if some temperature distribution is assumed, thereby allowing the equation above to be numerically integrated. A temperature distribution that works well for solving the equation is an error function where the temperature is maximum at "−a" and asymptotically approaches a constant value somewhere inside the edge of the first slide. A similar analysis is then performed to find the heat distribution required in the heater to produce the desired temperature distribution. This also is an error function, but surprisingly can be approximated by a linearly decreasing heat load. FIG. 11B shows a heat distribution (Z represents the magnitude of heat production from the radiant heater) of a nearly rectangular heater used in a working embodiment of the disclosed system. The heat production is uniform over the central region 444, then linearly increases near the edges to a maximum value 446, as indicated. At the corners, the heat increases linearly in both directions, giving rise to the peaks at the corners 448. As positioned in a working embodiment of the system, the corners of the otherwise rectangular heater had to be cut off for the heater to fit within the system's cabinet frame, giving rise to the truncated corners 450 of the heat profile. However, the cut corners overhung the slide tray in the baking station by sufficient distance that the lower heat production at these cut corners did not significantly affect heating uniformity across slides. Experimental testing of the heater showed that the slide temperature was uniform to within about 2 K (such as within 1 K) over all slides in a tray positioned below the radiant heater.

E. Stainer/Combined De-Paraffinizer and Stainer/Combined Stainer, De-Paraffinizer and Solvent Exchanger.

A workstation is provided that can be used to apply one or more reagents to slides during one or more slide processing operations. Since the workstation typically includes one or more nozzles, and more typically one or more banks of nozzles, the workstation is actually a highly versatile workstation that can function not only as a workstation for applying staining reagents to slides, but also for applying de-paraffinizing, wash and solvent exchange reagents or any other type of reagent used in a particular slide processing operation. Thus, the workstation can also be used as a de-paraffinization workstation and/or a solvent exchange workstation. In a working embodiment of the disclosed system, a single workstation functions as a combined de-paraffinizer/stainer, and in another working embodiment, a single workstation functions as a combined de-paraffinizer/stainer/solvent exchanger. In performing each of these functions, multiple reagents can be applied in any particular series to slides held in a slide tray without moving the slides to another workstation.

Figure 12:
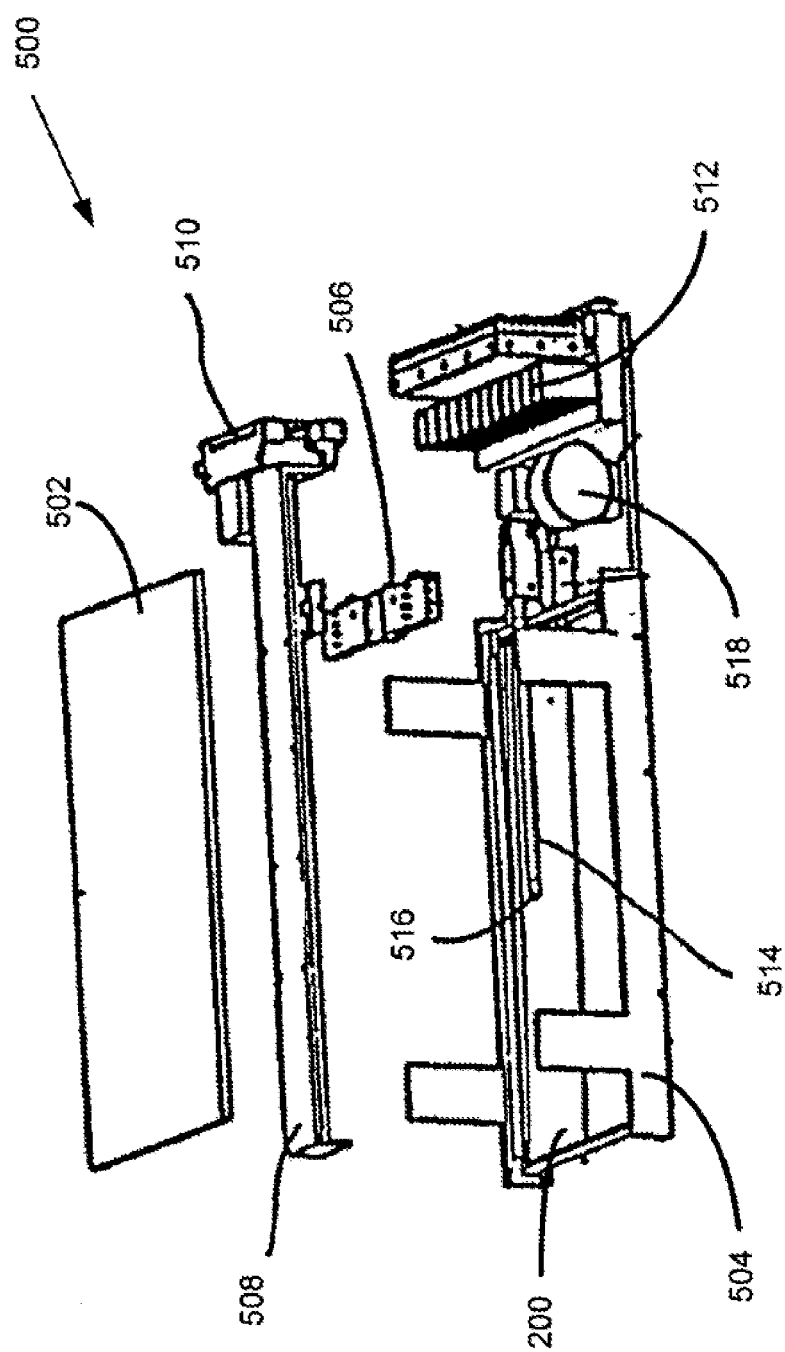
FIG. 12 is a perspective view showing an embodiment of a stainer workstation that can be included in the disclosed system.

FIG. 12 shows a particular embodiment of a stainer 500 that includes a top portion 502 and a bottom portion 504 that form a compartment housing a nozzle manifold 506 (including one or more nozzles, or banks of nozzles, such as at least two banks of nozzles, for adding reagents simultaneously to a pair of slides held in a slide tray) that is mounted on rail 508 and driven back and forth along the rail 508 by a drive screw (not shown) and stepper motor 510 combination so that it can be moved into position over a pair of slides held in a slide tray like the one illustrated in FIGS. 5 and 6. Valve block 512 is connected to the nozzle manifold 506 and functions to control the type of reagent that is dispensed from the nozzle manifold. Excess reagent that collects in slide tray 200 is removed from the tray in this embodiment by aspirator 514 that includes distal end 516 that is dipped to the bottom of the slide tray. Pump 518 then removes spent reagent from the tray through aspirator 514.

Figure 13:
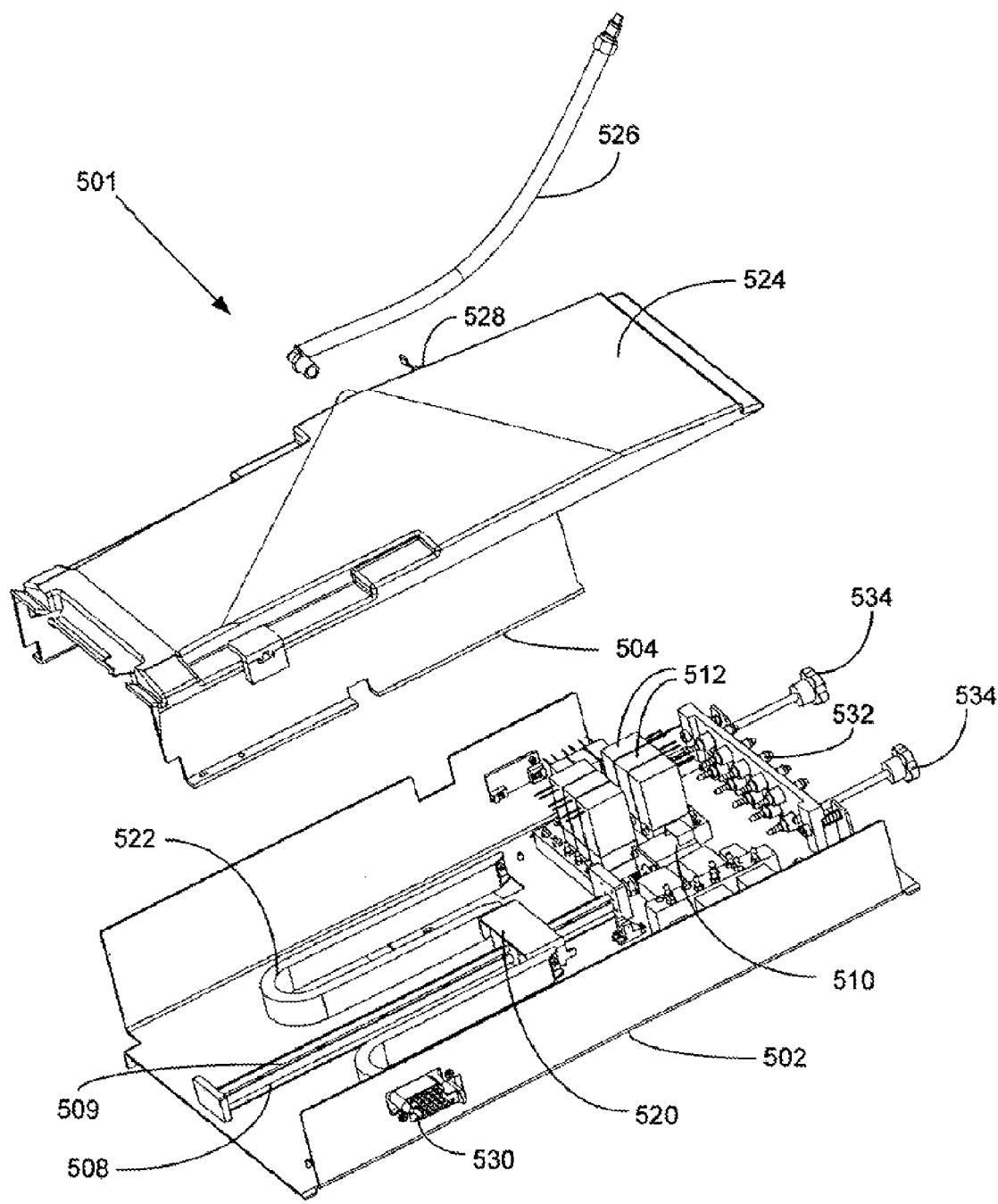
FIG. 13 is perspective view from below showing an embodiment of a combined de-paraffinizer/stainer workstation that can be included in the disclosed system.

FIG. 13 shows a working embodiment of workstation that can be used as a combined de-paraffinizer/stainer, or can be used to de-paraffinize, stain and solvent exchange. FIG. 13 shows such a workstation from a bottom perspective view. Workstation 501 includes a top portion 502 and a bottom portion 504 that form a compartment housing a rail 508 along which a nozzle manifold (not shown in FIG. 13, see FIG. 14) that is mounted to nozzle carriage 520 is driven back and forth within the workstation compartment by screw drive 509 and stepper motor 510. Valves 512 switch the reagent stream that is applied to slides through the stainer nozzle between different reagents and air during operation. Although the fluidics connections (such as hoses) are not shown in FIG. 13, these connections can be made through energy chain 522 that is attached to nozzle carriage 520. Attached to the lower portion 504 of the combined de-paraffinizer/stainer is drain pan 524 that is connected to drain tube 526, which can be used to carry spent reagents away from the workstation. An overflow sensor 528 such as a thermistor that can detect an overflow condition within the drain pan also can be included.

As was discussed with reference to FIGS. 2 and 3 workstations can be configured to include common electronics connections and fluidics connections such that workstations can be interchanged in position or replaced quickly and easily. The workstation of FIG. 13 includes data and power plug 530 configured to plug into an electronics manifold and fluidics interface 532 that includes a plurality of connectors that mate with corresponding connectors on a fluidics manifold. In a particular embodiment, the connectors on the workstation are male connectors that can be drawn tightly into a corresponding set of female connectors on a fluidics manifold using screws 534, thereby providing a tight seal between the fluidics interface 532 and a fluidics manifold.

Figure 14:
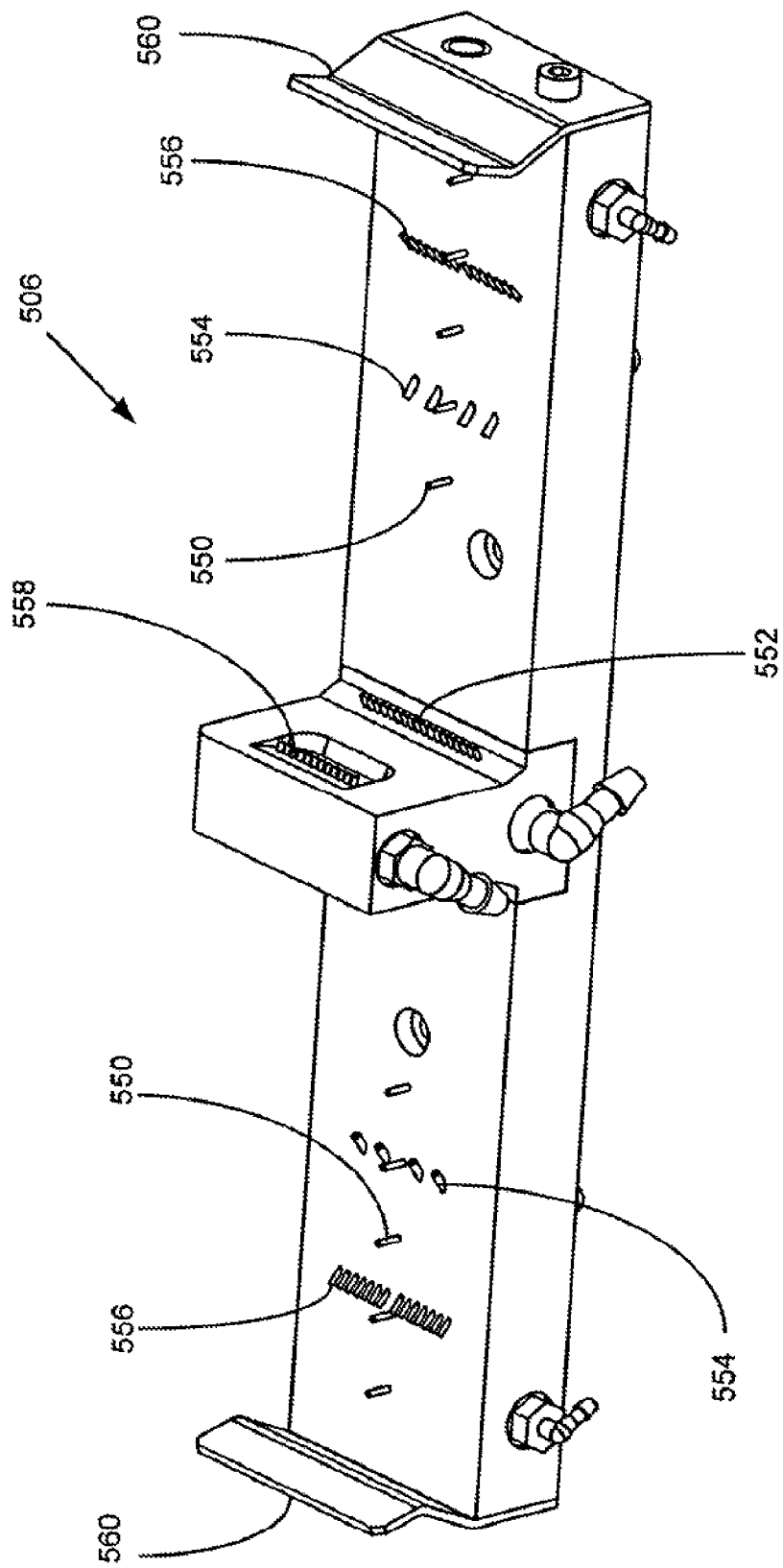
FIG. 14 is an elevational view of an embodiment of a nozzle manifold that can be used in the combined de-paraffinizer/stainer workstation of FIG. 13.

FIG. 14 shows a bottom perspective view of a working embodiment of a nozzle manifold 506 that can be used to apply reagents/pressurized air to pairs of slides held in each of two rows in a slide tray like the one shown in FIG. 6. Nozzle manifold 506 includes dispense nozzles 550, forward top surface rinse nozzles 552, backward top surface rinse nozzles 554, jet drain nozzles 556 (see, for example, U.S. Pat. No. 6,472,217, which is incorporated by reference herein), bottom surface rinse nozzles 558 and splashguards 560. In operation, nozzle manifold 506 is attached to nozzle carriage 520 of FIG. 13 and is moved over pairs of slides in a slide tray along rail 508 by stepper motor 510. Dispense nozzles 550 can be used to deposit reagent solutions onto the tops of slides, and air can be forced out of the same to distribute the reagent across the slide or even blow some of the reagent off of a slide. Forward top surface rinse nozzles 552 can be used to apply reagents to slides, for example, deionized water or other solvents, and air also can be forced through these nozzles to assist with spreading of reagents across the surface of a slide, to assist with clearing of liquids from the slide, or to clear reagents from the lines leading to the nozzles. In a particular embodiment, the angle of the forward top surface rinse nozzles 552 is such that streams of reagent exiting these nozzles will impinge on the top surface of a slide at an angle of between about 20 degrees and 30 degrees from the slide surface, for example at an angle of between about 22 degrees and about 28 degrees such as an angle of between about 24 degrees and about 26 degrees. Such angles of impingement are advantageous for reducing skipping of reagents past portions of the slide surface and for reducing the splashing of reagents off of the slide surface (which might, for example, cause cross-contamination of slides). Backward top surface rinse nozzles 554 can be used, for example, to rinse reagents from a label portion of a slide.

Air can also be directed through these nozzles to assist reagent removal, or to remove any reagent in the lines leading to the nozzles. In a particular embodiment, the backward top surface rinse nozzles are configured to deliver reagents so that they impinge on the top surface at an angle of between about 20 degrees and about 50 degrees relative to the slide surface, for example, an angle of between about 25 degrees and about 45 degrees such as an angle of between about 30 degrees and about 40 degrees. Again, such angles are advantageous. In a particular embodiment, streams of reagent from the backward top surface rinse nozzles are used in combination with streams of reagent from the forward top surface nozzles to produce "walls" of reagent solution, which travel down the slide and very effectively rinse the slide surface. In this particular embodiment, the forward top surface rinse nozzles and the backward top surface rinse nozzles can be configured to apply reagents to the slide at substantially the same position on the slide. By continuously streaming reagent (such as de-ionized water) from the forward top surface rinse nozzle and pulsing reagent from the backward top surface rinse nozzle a moving "wall" of reagent can be formed. The "wall" forms during the time when both sets of nozzles are on, and as a result of their opposing directions of flow at their intersection. When the backward top surface rinse nozzles are pulsed off, the wall of reagent then travels down the slide in the forward direction. Jet drain nozzles 556, which direct streams of reagent (such as de-ionized water) toward a slide near its edge, for example, within about 0.0200 in. of the edge of a slide, can break the surface tension of liquids on the slide and help draw such liquids off of the slide (for example, off the short edges of the slides near the side walls of the slide tray as shown in FIG. 6). Typically, jet drain nozzles 556 are directed toward the surface of a slide at its edge at an angle of less than 90 degrees, for example, at an angle of less than 45 degrees such as an angle of about 20 degrees. In a particular embodiment, jet drain nozzles 556 can be pulsed to coincide with the arrival of the "wall" at the slide's edge. Bottom rinse nozzles 558 can be used to remove reagent (such as staining reagents) that cling to the bottom surface of a slide during slide processing operations, and enable a method of rinsing the bottom of a slide during a slide processing operation. Splash guards 560 function to help prevent reagents from splashing out of the slide tray and into the workstation. They also can serve to reduce or minimize the potential for cross-contamination between slides in a slide tray. Although in the illustrated embodiment, the nozzle is designed to be moved into position over a pair of slides (or into a position over particular portions of a pair of slides) held in a slide tray, it is to be understood that a smaller moveable nozzle assembly that is moved to various positions over individual slides or a larger moveable nozzle assembly that is moved to positions over larger groups of slides (such as 3, 4, 5, 6 or more slides) are contemplated.

Figure 15:
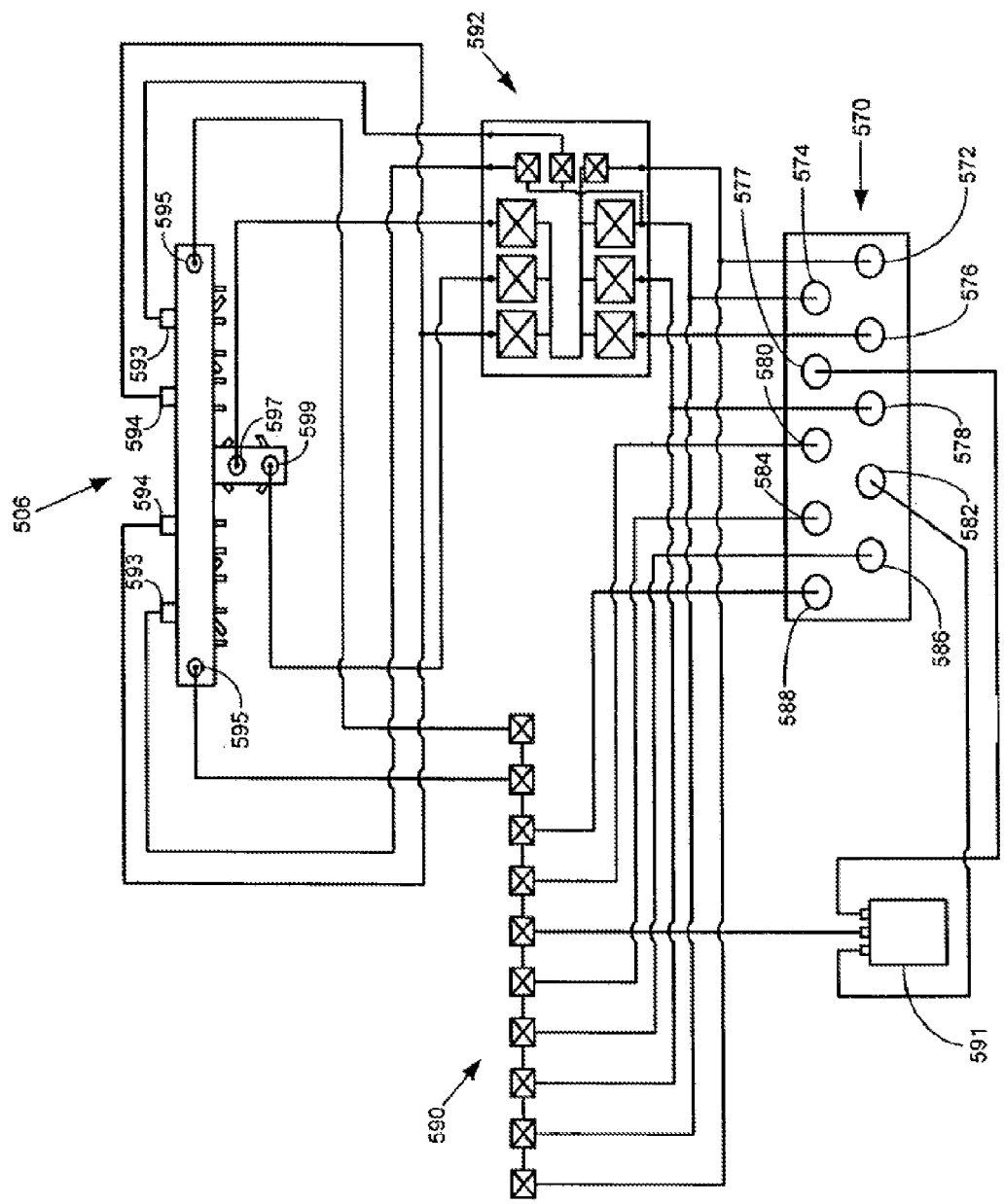
FIG. 15 is a schematic diagram showing an embodiment of a fluidics system supplying reagents to the nozzle manifold of FIG. 14.

FIG. 15 shows a representative schematic of a fluidics system that can supply reagents and pressurized air to the nozzle manifold of FIG. 14 for automated de-paraffinization and H&E staining (and in some instances solvent exchange) of biological samples placed on microscope slides. Reagent/air supply 570 (including, for example, the fluidics module discussed in detail below) includes pressurized air supply 572, deionized water supply 574, rinse solution supply 576 (for example a supply of a surfactant solution such as a 0.1% Tween 20 solution), a first concentration hematoxylin solution supply 577, an alcohol (typically ethanol) supply 578, an eosin solution supply 580, a second concentration hematoxylin solution supply 582, a bluing solution supply 584, a limonene supply 586 (or a supply of any other de-paraffinizing reagent such as those discussed above) and an acid solution supply 588. The various individual reagent supplies and the air supply included in reagent/air supply 570 can be connected as shown to one or more of a dispense manifold 590, a hematoxylin select valve 591 and a rinse manifold 592. Selection of reagents/air for delivery to slides is performed using valves in the dispense manifold 590, the hematoxylin select valve 591 and valves the rinse manifold 592. Selection can be performed under computer control. In some circumstances, more than one reagent can be introduced into the same line (continuously or in pulses) to provide mixtures of reagents, for example, deionized water/alcohol mixtures, and mixing chambers (such as inline mixing chambers) can also be included. Note that at least some of the nozzles on the two sides of the nozzle assembly are separately plumbed, making it possible to apply a reagent to only one slide in a pair of slides on opposite sides of a slide tray. Thus, a reagent can be applied to two slides in an opposed pair in series or simultaneously. Or, if no slide was detected in a position in a tray, no reagent need be applied to that position while a slide in an opposed position can be treated. In other embodiments, each different type of nozzle in a nozzle assembly can be separately plumbed or all nozzles of a particular type can be plumbed together.

Reagents/air are supplied to particular nozzles or sets of nozzles in nozzle manifold 506 (see discussion of FIG. 14) as shown in FIG. 15. Reagents are supplied to the jet drain nozzles through jet drain nozzle inlets 593, to backward top surface rinse nozzles through backward top surface rinse nozzle inlets 594, to dispense nozzles through dispense nozzle inlets 595, to forward top surface rinse nozzles through forward top surface rinse nozzle inlet 597 and to bottom surface rinse nozzles through bottom surface rinse nozzle inlet 599.

F. Solvent Exchanger

Most biological stains that are commonly used are aqueous or aqueous/alcohol based. Thus, biological samples such as paraffin-embedded tissue samples are first de-paraffinized and hydrated before staining since aqueous-based stains cannot penetrate paraffin and stain tissue components. Conversely, the fluids used to dissolve coverslip adhesives and mount coverslips onto microscope slides are generally immiscible with water. Therefore, after a biological sample has been stained, the water that remains in the sample is first replaced with a non-aqueous based fluid compatible with coverslipping before the sample is coverslipped. This function can be accomplished in a solvent exchanger workstation.

A working embodiment of a solvent exchanger is shown in FIG. 16. However, it should be understood that such a workstation can also perform additional slide processing operations, for example, staining or de-paraffinizing, either as shown or with some modification. The solvent exchanger 600 of FIG. 16 includes a top portion (not shown for clarity) and a bottom portion 602 that form a compartment that receives a slide tray and is configured to perform one or more slide processing operations. A nozzle manifold 604 (including one or more nozzles or banks of nozzles, for example, dispense nozzles as in the embodiment of FIG. 14) further includes a pair of blow-off nozzles 606. The nozzle manifold 604 is attached to nozzle carriage 608, which is itself attached to rail 610 (which can be attached directly to the unseen top portion). The nozzle manifold 604 attached to nozzle carriage 608 is moved along rail 610 within the workstation by stepper motor 612 coupled to screw drive 613 by drive coupling 614. Reagents are supplied to nozzle manifold 604 through tubing (not shown) that is directed through energy chains 616 so that the tubing does not interfere with the movement of the nozzle manifold 604 over successive pairs of slides in slide tray 618.

As shown in FIG. 16, a slide tray 618 is held in the workstation in tilt pan 620. A Hall-effect sensor 622 is mounted on lower portion 602 of the workstation to detect the presence of slide tray 618 in its proper position in the workstation (which can be used to alert the system's computer to begin a slide processing operation because the slide tray is properly positioned or to suspend the slide processing operation because the slide tray was not properly received into the workstation). Hall-effect sensor 622 detects the tray in the workstation by detecting the presence of magnet 624 which is mounted in a recess on the side of slide tray 618. Tilt pan 620 includes wicking plate 626 that contacts the opening in the end wall of slide tray 618, which aids in removal of spent reagents from slide tray 618. Living hinge 628 is configured to permit rotation of the tilt pan 620 around a single axis such that the end of slide tray 618 adjacent to wicking plate 626 is lowered and the end of slide tray distal to the wicking plate is raised, without substantial torsional movement about the long axis of the tilt pan. In operation, tilt pan 620 can be rotated and spent reagents are guided out of slide tray 618 along wicking plate 626 and into pan 630. It should be understood that other types of workstations that receive slide trays in the disclosed system also can include a Hall-effect sensor for sensing the presence of a tray in the workstation and/or a tilt pan and wicking member (such as a wicking plate) as are illustrated in FIG. 16.

As mentioned above, the solvent exchanger 600 can be used to exchange residual aqueous fluids from a previous staining step with a non-aqueous fluid that is compatible with a subsequent coverslipping process. Thus, in addition to the components already discussed above, the solvent exchanger can include an inline mixing valve (not shown) that can be used to deliver a series of reagent solutions that gradually transition from water through alcohol to a non-aqueous fluid such as D-Limonene. In a working embodiment, deionized water (which can include a surfactant such as Tween 20), alcohol and D-limonene are provided in bulk (or from a laboratory water deionizer in the case of deionized water) and mixed in the inline mixing valve to provide such transitioning solutions. In a particular embodiment, the mixing is performed under computer control.

A typical succession of solutions that can dehydrate a biological sample and leave a solvent that is compatible with coverslipping on a slide is as follows:
1) 100% water;
2) 75% water/25% ethanol;
3) 50% water/50% ethanol;
4) 25% water/75% ethanol;
5) 100% ethanol;
6) 75% ethanol/25% D-limonene;
7) 50% ethanol/50% D-limonene;
8) 25% ethanol/75% D-limonene;
9) 100% D-limonene.

In a particular embodiment, as a last slide processing operation performed in the solvent exchanger, the slides are blown clean using blow-off nozzles 606 and then a controlled amount of D-limonene is dispensed to the slides in a slide tray. The slide tray is then transported to the coverslipper by a transporter without removing the D-limonene from the slides, and the D-limonene dispensed in the solvent exchanger is used as the coverslipping solvent in the coverslipper. This embodiment will be discussed in more detail below.

As shown in FIG. 16, the solvent exchanger also can include one or more blow-off nozzles 606. The blow-off nozzles are carried along rail on nozzle carriage 608 and used to blow excess fluids from the slides between successively more non-aqueous solutions and/or to help spread fluids across a slide to help ensure that a biological specimen is evenly contacted with each successive fluid. Several more detailed views of the blow-off nozzle are shown in FIG. 17 A-C, one of which also shows an air jet formed by the blow-off nozzle that can be used to push fluids across and/or off a slide. An exploded view of a particular embodiment of the blow-off nozzle 606 is shown in FIG. 17A. The blow-off nozzle 606 includes a nozzle body 650 that includes plenum 652 that feeds pressurized gas (typically air) from inlet 654 to the nozzle. The nozzle is formed by the gap in nozzle spacer 660, which is attached to the bottom surface 658 of nozzle body 650 by lower nozzle plate 662. In this embodiment, the lower nozzle plate is held in place by hex screws 664. FIG. 17B shows a cross section of the nozzle orifice 668 formed by the nozzle body 650, nozzle spacer 660 and lower nozzle plate 662. FIG. 17C shows the blow-off nozzle 606 and an air jet 670 formed by passing pressurized air, for example, through the nozzle. This air jet can be passed across a slide 672 to spread a reagent 676 over a tissue sample 674, or to remove at least some of reagent 676 from slide 672. The force exerted by the air jet can be adjusted by altering the pressure of the gas introduced into the inlet 654 and/or adjusting the width of the nozzle orifice 668 by using a different thickness for nozzle spacer 660. The angle of the air jet with respect to the surface of the slide can be adjusted by either altering the angle of the bottom surface 658 of nozzle body 650 or by mounting the entire blow-off nozzle at a different angle. In general, the angle at which the air jet impinges upon a surface of a slide can be adjusted to between about 20 degrees and about 60 degrees, for example, to an angle between about 30 degrees and about 40 degrees such as an angle between about 34 degrees and about 36 degrees. An angle of about 35 degrees is particularly efficient, and permits the use of a lower air pressure while still achieving a low residual volume on a slide after a reagent removal pass.

A blow-off nozzle like the one illustrated in FIG. 17 can be included in one or more workstations of a disclosed system, for example, in both a solvent exchanger workstation and a coverslipper workstation. For example, a working embodiment of the disclosed system includes 2 blow-off nozzles in a solvent exchanger and 2 blow-off nozzles in a coverslipper. Each pair of blow-off nozzles in the two workstations of the working embodiment can be used to simultaneously perform a slide processing operation on a pair of slides held in a slide tray. In these particular embodiments, the blow-off nozzles are used to move reagents across the width (1") of a slide rather than the length of the slide (3").

G. Coverslipper

The disclosed system also can include a coverslipper workstation that receives a slide tray holding a plurality of slides in, for example, a substantially horizontal position, and performs a coverslipping operation wherein coverslips are added to slides held in the tray. In a working embodiment of the disclosed system, the coverslipper is substantially as described in U.S. Patent Application Publication No. 2004/0092024A1, which is incorporated by reference herein.

However, modifications of the coverslipper described in the above application and its operation were implemented in a working embodiment of the disclosed system to increase coverslipper precision, decrease coverslipper complexity and increase system throughput.

Figure 18:
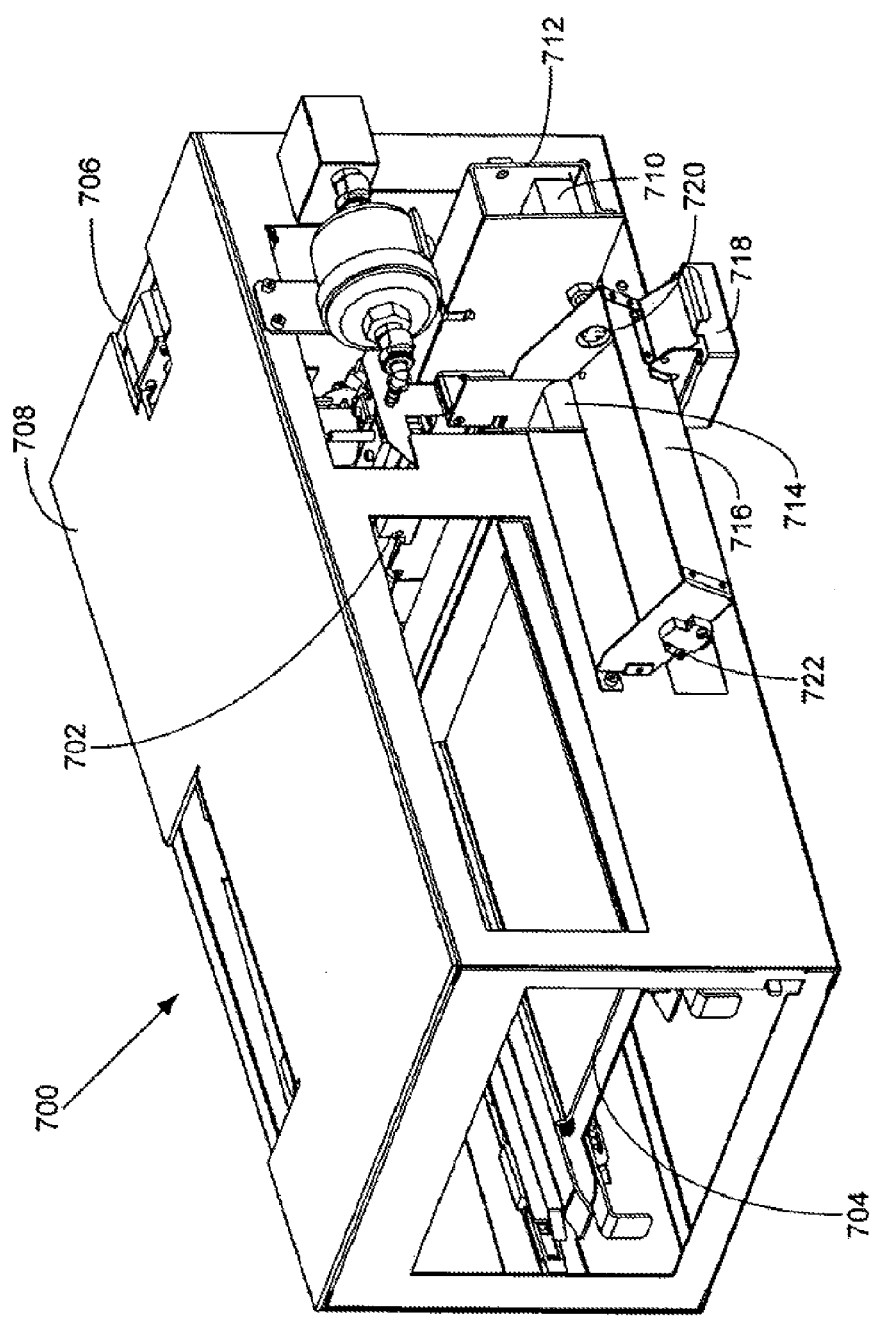
FIG. 18 is a perspective view showing an embodiment of a coverslipper that can be included in the disclosed system.

FIG. 18 shows a perspective view of a coverslipper such as described in U.S. Patent Application Publication No. 2004/0092024A1. Briefly, coverslipper 700 includes a head portion 702 that is moved along a rail (not shown, but similar to other rails previously discussed for other types of workstations) that is located above slide tray docking assembly 704 by stepper motor 706. Slide coverslips in a keyed coverslip cartridge 710 (can be added to system in only one orientation) are introduced to the coverslipper through cartridge portal 712 along a first conveyor belt (not shown). In a particular embodiment, the coverslip cartridge includes an RFID tag that is read/written to inside of coverslipper by an RFID antenna that transmits cartridge information (such as lot number, number of coverslips removed from the cartridge etc.). Spent cartridges and broken coverslips are removed from the coverslipper by a second conveyor belt 714 and fall into cartridge catch tray 716. Broken coverslip pieces slide through a narrow slot in the front of cartridge catch tray 716 into a coverslip catch tray 718. As spent cartridges are added to the cartridge catch tray 716 they are moved away from the end of second conveyor belt 714 by air pressure activated piston 720 so that additional cartridges can be ejected. When cartridge catch tray 716 is full of spent cartridges, sensor 722 can be used to alert a user that the catch tray needs to be emptied. Additional details regarding the design and operation of the coverslipper can be found in U.S. Patent Application Publication No. 2004/0092024A1.

Figure 19:
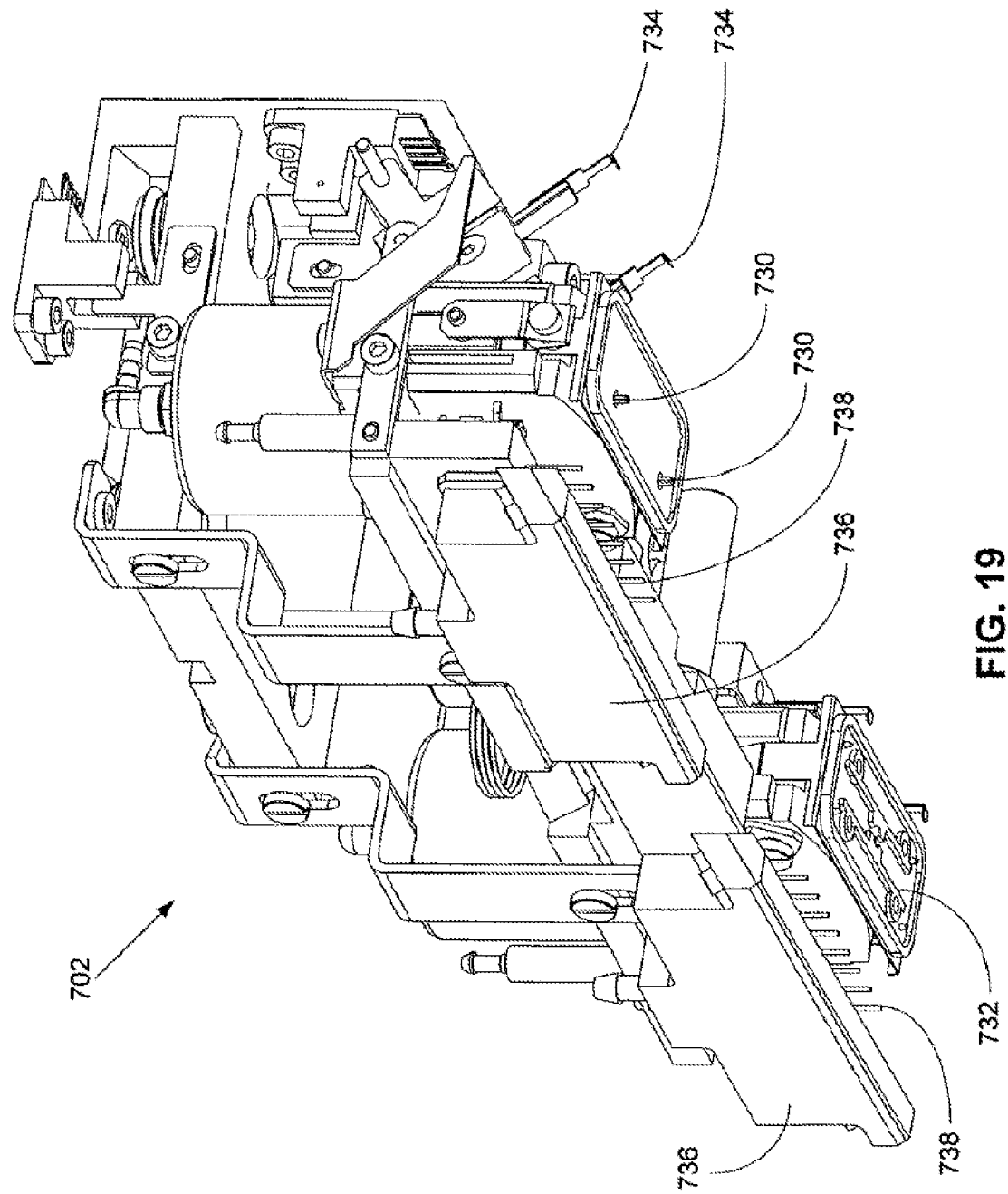
FIG. 19 is a perspective view showing an embodiment of a coverslipper head.

FIG. 19 shows the head portion 702 of the coverslipper in more detail, and in particular shows modifications that can be made to the head portion to improve coverslipper precision, reduce coverslipper complexity and increase system throughput. In particular, head portion 702 comprises tandem units that each can include one or more spring loaded pins 730 (shown on the right unit) that pass through holes in sealing member 732 (shown on the left unit) that is used to grip individual coverslips when a vacuum is applied to the head. The pins 730 normally are urged by springs to extend slightly beyond the surface of sealing member 732, but are forced behind the surface of the sealing member when a coverslip is drawn in contact with the sealing member by applied vacuum. Upon release of the vacuum, the pins 730 are pushed beyond the surface of sealing member 732 and thereby assist in separating coverslips from the head portion 702. Pins 730 also served to hold a coverslip in place on a slide surface as hooks 734 are withdrawn during a coverslipping operation such as the operation described in U.S. Patent Application Publication No. 2004/0092024A1. Pins serve to increase coverslipper precision by holding the coverslip in place during hook removal, which otherwise might cause a coverslip to shift to one side on the slide.

Also show in FIG. 19 are blow-off nozzles 736, which can be essentially of the same design as the blow-off nozzles described above and shown in FIG. 17, but possibly modified with respect to air pressures used and nozzle orifice size. Although these nozzles can be used to clean slide surfaces prior to dispensing a solvent compatible with coverslipping (such as toluene, xylene or D-limonene) onto a slide surface from dispense nozzles 738, in a particular embodiment, D-limonene is dispensed as a last step in another workstation such as a solvent exchanger and then the slides in a slide tray are transported to the coverslipper. When the slide tray arrives in the coverslipper, the D-limonene will have spread across the surface of the slide. Blow-off nozzles, which are in essence functioning as an air broom, can then be used to push the D-limonene on the slide surfaces toward a long edge of the top surface of the slides, after which this bead of D-limonene functions as a bead of solvent that would otherwise be dispensed from dispense nozzles 738 as is described in U.S. Patent Application Publication No. 2004/0092024A1. Thus, since the coverslipping solvent can be added to slides in a separate workstation, dispense nozzles 738 are optional in the embodiment just described. Without the need to dispense coverslipping solvents in the coverslipping station a number of components including metering pumps, delivery lines and the dispense nozzles can be absent from the coverslipper in this embodiment, thereby reducing coverslipper complexity. Furthermore, by dispensing the coverslipping compatible solvent in another workstation, a blow-off step in the other workstation and a dispensing step in the coverslipper can be eliminated, thereby increasing system throughput.

In a particular embodiment, the coverslips applied to slides are coated, on their bottom surface, with a dry, activatable adhesive. The adhesive is activated by a solvent compatible with coverslipping that is placed on the slide (for example, either in a solvent exchanger or a coverslipper). Examples of dry, activatable adhesives include Permount™ (Fisher Scientific, Pittsburgh, Pa.) or ShurMount™ (Triangle Biomedical, Durham, N.C.). U.S. Pat. No. 6,759,011, describes a more particular example of a pre-glued coverslip that can be used in the coverslipper, and is incorporated by reference herein. In an alternative embodiment, glue is applied to slides (such as through dispense nozzles 738) prior to placement of a coverslip onto a slide.

Figure 20:
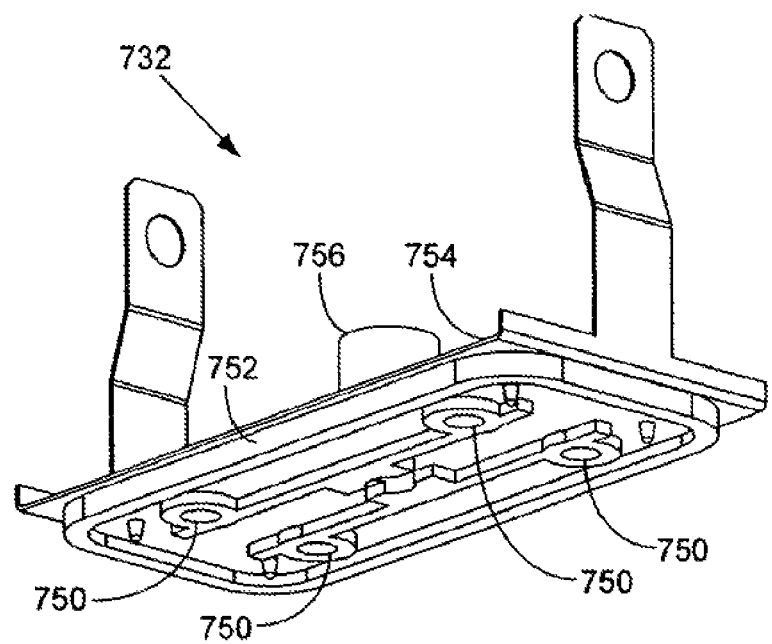
FIG. 20 a perspective view showing an embodiment of a sealing member of a coverslipper head.

FIG. 20 shows a more detailed diagram of a particular embodiment of sealing member 732 that can be easily replaced on the coverslipper head 702 shown in FIG. 19, and that is compatible with pins 730 shown in FIG. 19. Sealing member 732 can be placed onto the coverslipper head 702 in either of two orientations since it includes four blind holes 750 that permit passage of pins 730. Holes 750 are formed in the gripper portion 752 of the sealing member, and the gripper portion is attached to flexible backing 754, which also has corresponding holes. Vacuum is applied to the sealing member through vacuum plenum 756.

H. Transporter

Any means for transporting slide trays between workstations can be employed in the disclosed system. The transport means can include any combination of shuttle tables, conveyor belts, elevators and the like equipped with one or more means to push slide trays off of or to pull slide trays onto the transport means. In a working embodiment, a transporter includes an X-Y shuttle table for moving slide trays horizontally and an elevator for moving the shuttle table up and down vertically within the system. In a working embodiment, an X-Y-Z transporter is used to move slide trays between modular workstations arranged in a vertical stack.

Figure 21:
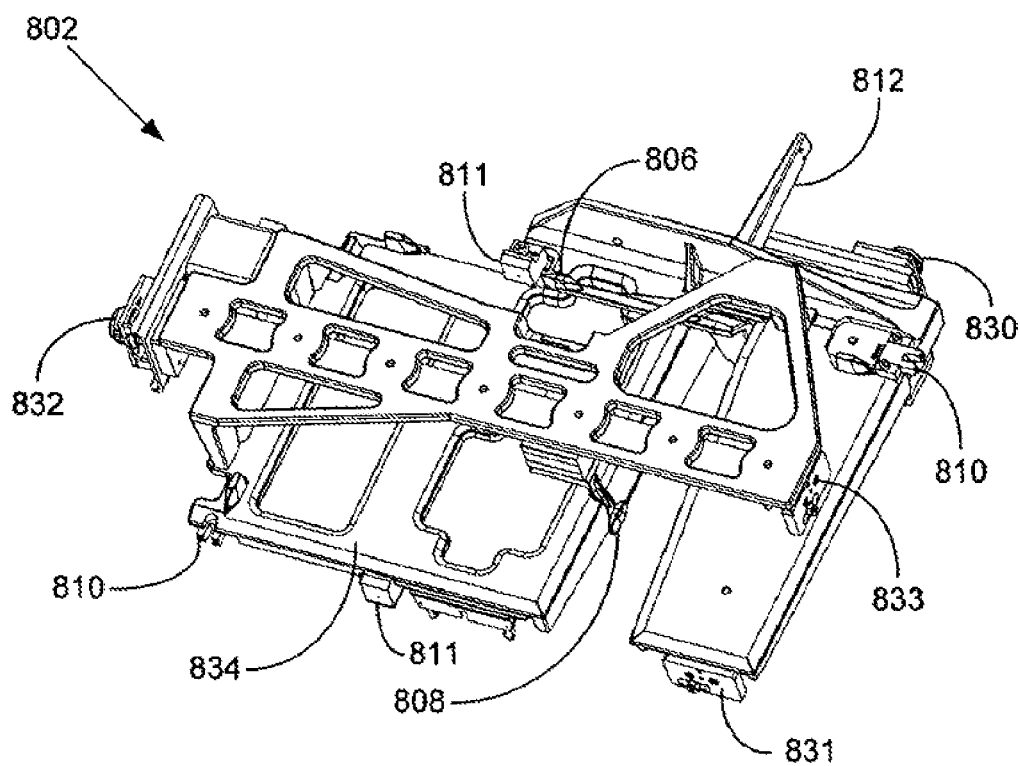
FIG. 21 is a perspective view showing an embodiment of an X-Y shuttle table that can be included in the disclosed system.

FIG. 21 shows one embodiment of an X-Y shuttle table 802. The X-Y shuttle table includes Y-hook 806 that pulls and pushes a slide tray onto and off of table surface 834 in the Y-direction (front to back in the system of FIG. 3) and X-hook 808 that pulls and pushes a slide tray onto and off of table surface 834 in the X-direction (side to side in the system of FIG. 3). The X- and Y-hooks are configured in a working embodiment to engage, for example, a side hook 246 or end hook 246 on the slide tray shown in FIG. 6. Y-hook 806 is moved by stepper motor 830 along rail 831 with a first screw drive mechanism (not shown), and X-hook 808 is moved along by stepper motor 832 along rail 833 with a second screw drive mechanism (also not shown). Sensors 810 (for example, Hall-effect sensors and/or optical sensor) are included on X-Y table 802 to detect table position within the system (which can be used to index the table's position for accurate automated movements within the system). As will be discussed with reference to FIG. 22A below, X-Y shuttle table 802 is moved in the Z-direction (up an down in the system of FIG. 3) using elevator assembly 804. X-Y shuttle table 802 also includes guide member 812 that slides up and down in a vertical track at the back of the system of FIG. 3 (not shown) that keeps the table itself substantially stable in the X and Y directions within the system as it is moved in the Z direction by the elevator assembly discussed below.

Figure 22B:
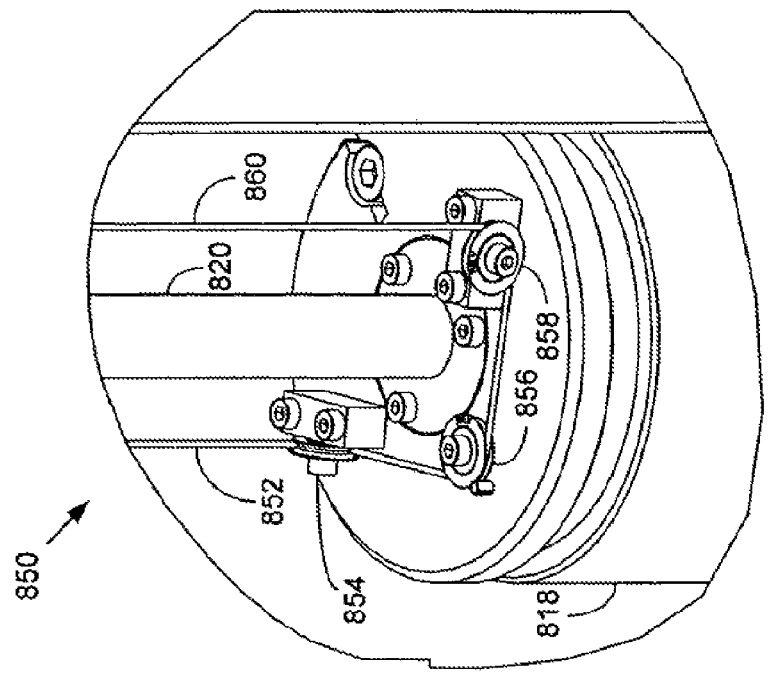
FIGS. 22 A-B are a pair of perspective views showing an embodiment of an X-Y-Z transporter that can be included the disclosed system.
Figure 22A:
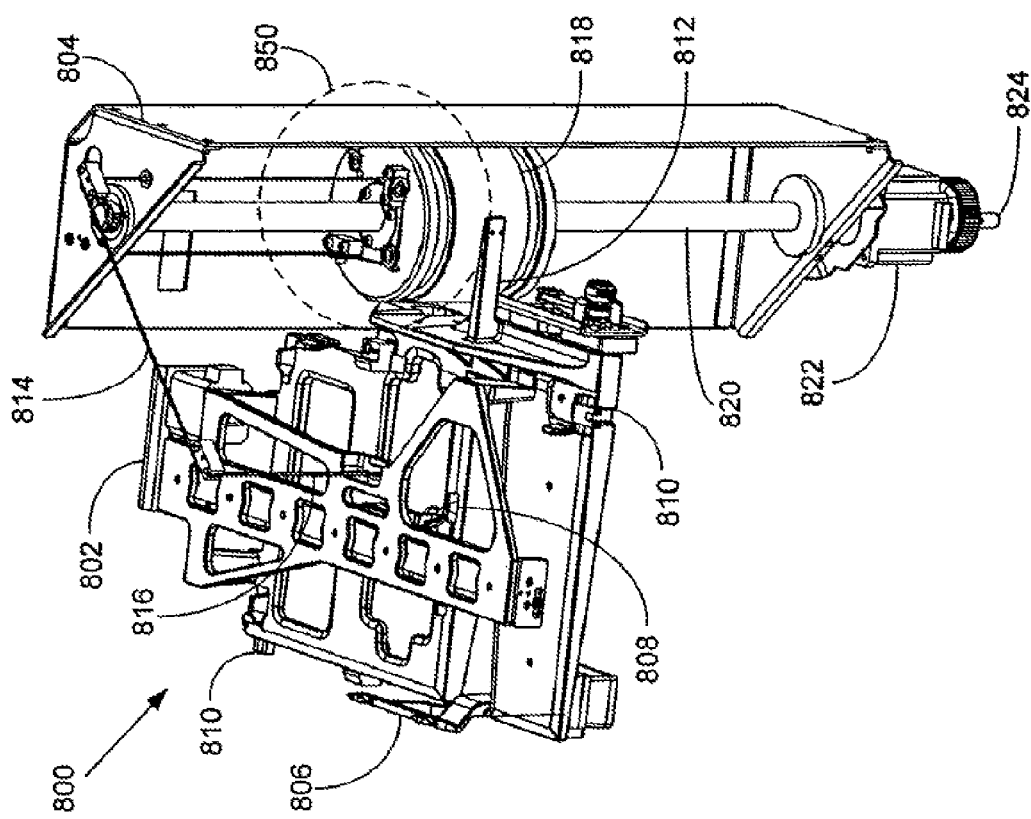

FIG. 22A shows an X-Y-Z transporter 800 for use in the disclosed system that includes X-Y shuttle table 802 and elevator assembly 804. Also shown in FIG. 22A is vertical section 816 of cable 814 that is attached to the shuttle table substantially at the center of gravity of the table. Suspending the X-Y shuttle table at its center of gravity makes it less likely that guide member 812 will bind in its vertical track, thereby reducing friction and making it possible to use lighter, less structurally rigid materials for the guide. Cable 814 connects X-Y shuttle table 802 to elevator system 804 and in particular to counterweight 818. In this embodiment, counterweight 818 is driven rather than the shuttle table itself (although other working embodiments not shown have employed a driven table with a passive counterweight). Counterweight 818 is moved along screw drive 820 in the Z-direction by stepper motor 822. Hand crank 824 also is provided to assist a user, for example, in freeing the transporter in the unlikely event that it should bind during operation. Binding of the counterweight along screw drive 820 is made less likely by also suspending counterweight 818 substantially from its center of gravity. However, in the embodiment of FIG. 22A, the center of gravity of counterweight 818 is located in a position that is occupied by screw drive 820. A unique solution for suspending the counterweight by its center of gravity that also permits the use of a 2:1 pulley system is illustrated in inset 850. The 2:1 system moves the X-Y shuttle twice the distance the counterweight 818 is moved along screw drive 820. Inset 850 is shown in greater detail in FIG. 22B.

FIG. 22B shows a particular system of pulleys that serves to suspend counterweight 818 substantially from its center of gravity. A first vertical section of a cable 852 that is attached to the roof of the elevator assembly runs through a first pulley 854 through offset pulley 856 and through a second pulley 858. A second vertical section of cable 860 is attached to the X-Y shuttle table. The combination of pulleys holds the counterweight through its virtual center of gravity.

Sensors such as 810 (optical) and 811 (Hall-effect) carried on the X-Y shuttle table can be used to sense, for example: (1) a home or first garage position; (2) one or more workstation positions; (3) a bar code reader position; (4) a portal position or (5) presence of a tray on the shuttle table or in a garage or workstation. The signals from the sensors can be sent to a central processor and used to control workflow in the system. The sensors can be an inductive-type sensor for sensing a magnet or magnets placed in the elevator and/or on the side or bottom of the slide trays. Alternatively, optical sensors can be employed. Finally, encoders may be mounted on the lead screw and/or the stepper motors in the transporter and/or workstations to provide feedback on tray position, workstation mechanism positions and/or transporter position. Such information can also be used to detect system malfunctions such as jams.

I. Code Reader

The disclosed automated slide processing system also can include a code reader, for example, an optical bar code reader configured to detect and index individual slides in a slide tray. In this particular embodiment, the code reader includes a single code reading mechanism that works in conjunction with the X-Y shuttle table to index and/or detect slides held in two rows on a slide tray. In a working embodiment, a bar code reader workstation is located above a vertical stack of workstations, and a X-Y shuttle table is used to push the slide tray under the bar code reader assembly to read barcodes on slides in one row in the slide tray, and then the bar code reader assembly is moved to detect and index the other row of slides as the X-Y shuttle table is used to pull the slide tray out from under the bar code reader assembly. In an alternative embodiment, the code reader also can move, either alone or in conjunction with the slide tray to bring individual slides below the bar code reader so that the barcodes can be detected.

Figure 23:
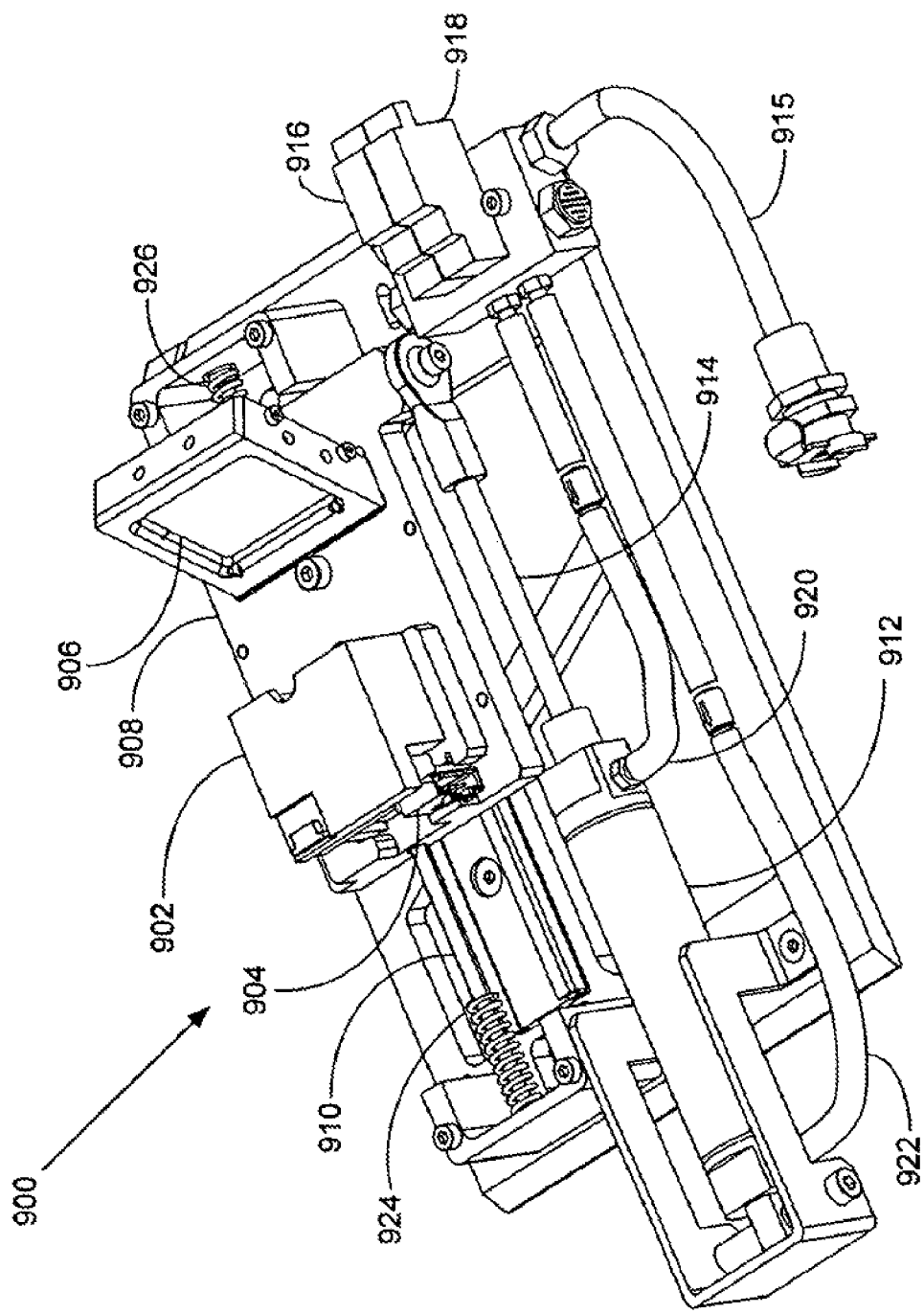
FIG. 23 is perspective view showing an embodiment of a bar code reader assembly that can be included in the disclosed system.

A bottom perspective view of a working embodiment of a bar code reader assembly 900 is shown in FIG. 23, which assembly is configured to read barcodes on slides held in a slide tray such as the one illustrated in FIG. 6. In this embodiment, bar code reader engine 902 (which can use a raster scan to accommodate 2-D barcodes), printed circuit board 904 and first surface mirror 906 are attached to stage 908 that is mounted so that it can slide along shaft 910. Stage 908 is mounted to piston rod 914 of bi-directional air cylinder 912. Air cylinder 912 is driven back and forth using pressurized air from supply hose 915 under control of valves 916 and 918 that feed separate cylinder supply lines 920 and 922 that are connected to opposite ends of air cylinder 912. In operation, pressurized air is passed through valve 918 and cylinder supply line 922 to maintain stage 908 in its illustrated position while the X-Y table moves a first row of slides under the first surface mirror 906 to read barcodes on slides in a slide tray (such as slides detected by an optical slide detector or detectors on the way into the code reader workstation). Once the first row has been detected and/or indexed, valve 918 is closed and valve 916 is opened to supply air to the other end of air cylinder 912 through cylinder supply line 920, which pulls piston rod 914 into the body of air cylinder 912 and moves stage 908 toward dampening spring 924, which spring reduces the shock of movement felt by the code reader engine 902. Then, the X-Y table moves the slide tray out from under the bar code reader assembly 900 in the opposite direction so that the other row of slides in the tray can be read. Another dampening spring 926 is provided to prevent shock when the assembly is returned to its illustrated position by switching valve 918 on and valve 916 off. Data regarding the particular slide tray and/or the individual slides carried thereon may then be transmitted to the central processor so that the tray and slides may be tracked through the system.

As mentioned above, an optical detector or detectors that sense the presence of slides in a slide tray (for example, an Omron EE-SPY sensor, Schaumberg, Ill.) also can be used in conjunction with the X-Y shuttle table. For example, by moving a slide tray underneath a detector(s) fixed within the system (such as a location on a partition between a workstation like the code reader and the elevator space of a X-Y-Z transporter), the presence of slides in particular positions in a slide tray can be detected. Such information can be used, for example, to allow workstations to discriminate between positions in a given slide tray that are actually occupied by a slide and those that are empty, thereby allowing the system to skip over empty locations and avoid dispensing costly reagents directly into the slide tray.

Alternatively, each of the slides can be tagged with an RFID tag, in which case the bar code labels can be eliminated and the bar code reader can be replaced by an RFID reader or readers. Slides also can be tagged with magnetic stripes, and a magnetic stripe reader employed in place of the bar code reader. Or, a combination of bar codes and a bar code reader, RFID tags and RFID reader, and/or magnetic stripes and a magnetic stripe reader can be employed in the code reader. It also is possible to include codes on slide trays in addition to the slides they carry so that particular slide trays can be identified within the system.

J. System Sequencing and Control

Figure 24:
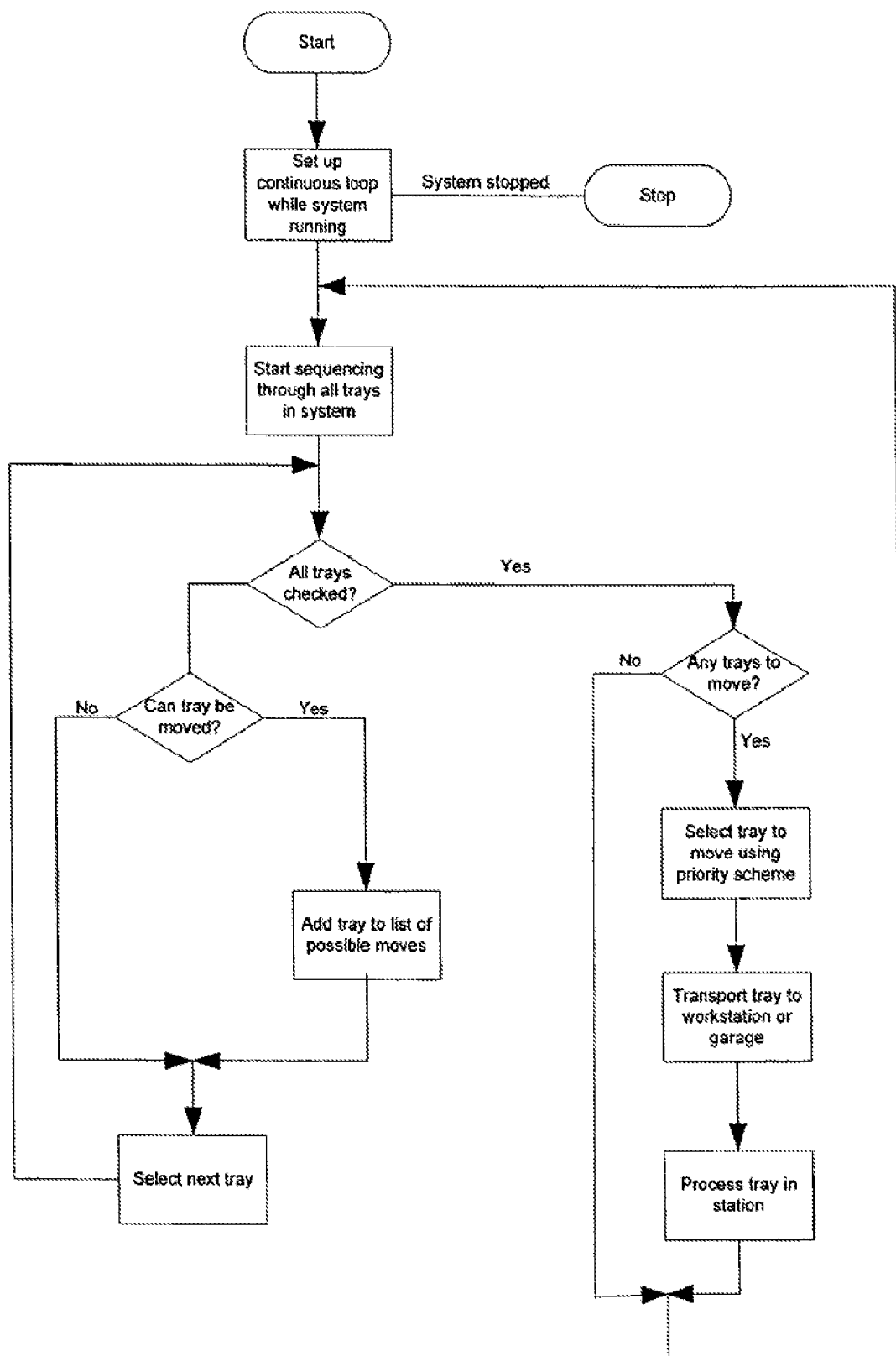
FIG. 24 is a flow chart showing a slide tray sequencing scheme.

A Run Time Executive (RTE) software application can be used to sequence and schedule the operations performed by several workstations on microscope slides held in trays. FIG. 24 shows a flow chart for sequencing and scheduling the movement of slide trays between workstations and a garage during automated processing of a plurality of slide trays holding microscope slides. In a working embodiment, the system can handle 25 slide trays at one time, with each tray undergoing the slide processing operations performed by one or more workstations and perhaps including multiple visits to the same workstation. As described above, trays can be moved within the system by a transporter such as an elevator and shuttle table combination. Together, this elevator and shuttle table combination can move a tray in the X, Y and Z directions as needed. Also, as noted above with reference to FIG. 3, the instrument can include a "parking garage" where trays can be placed while they are waiting for a workstation to become available, or when all scheduled operations are completed. A maximum number of trays handled by the system, 25, can match the number of parking slots in the garage.

A basis of actions performed on a tray can be based on an user-selected protocol which, among other things, designates the workstation operations to be performed on slides in a particular tray and the priority of the tray as "STAT" (expedited) or normal. Using this protocol, the RTE prepares an ordered sequence of workstations to be visited. Since there is only one elevator/table in the working embodiment, it can be viewed as a single server with multiple jobs to perform. Where the schedule for this problem can be calculated, it should be noted that the time of addition of trays to the system by a user cannot be predicted. Likewise, users can change the priority of a tray at any time. With these factors in mind, the schedule is determined dynamically prior to the time the elevator/table becomes available for work. Elevator/table "work" consists of a moving tray from point A to point B. Thus, after completing a move, the elevator/table is available. In anticipation of that time, the executive examines each tray in the system and creates a list of possible moves. Referring to FIG. 24, the process can be as follows:

1. First, determine if a tray can be moved. In order to move a tray, it must be either done in a workstation, "almost" done in a workstation (meaning it is estimated to be done by the time the elevator could next go to the workstation), parked and ready for next workstation, parked and ready for removal, or ready to be parked because of an abnormal condition.

2. If the tray can be moved, its next destination must be identified from its planned sequence and checked for availability. A workstation is considered available if it is both empty and operationally ready. If there is more than one of the target workstations available, the workstation that has been waiting the longest is chosen. If the tray's target workstation is not available, then it will either be routed to the parking garage or it will wait in its current workstation depending on the protocol. If the tray can be parked, the executive always chooses the empty parking slot closest to the tray's next target station.

Once the list of all possible moves is prepared, the executive selects the one move to perform. This selection is based on a determined tray priority and in the event of a tie, the time of arrival (TOA) of the tray to the system (i.e. entry time at the portal). The factors making up a tray's priority are as follows:

1. The highest priority is assigned to a tray if it is currently in the slide detect/bar code reading station. This highest priority is assigned because the shuttle table is involved with this station operation and until it has completed and moved the tray to its next station, no other move can be assigned to the elevator/table.

2. The second highest priority is assigned to a tray with a user-designated STAT priority.

3. The third highest priority is assigned to a tray whose protocol requires that it begin the next process within a certain time limit and that time limit will expire if not moved.

4. The fourth highest priority is assigned to a tray that is either in the portal waiting for entry into the system or in the garage waiting to be removed from the system. This priority accommodates the instances where a user is standing by waiting for the instrument.

5. The lowest priority is assigned to any tray that does meet the other four criteria.

The software mechanics of this selection consists of a record in a dynamic array structure that is made for each tray that can be moved. This record contains tray identification, the determined priority, and the tray's TOA. The array is sorted by priority and then TOA and the entry at the top of the list is the tray given to the elevator/table to perform.

The main system computer is responsible for scheduling and coordinating the movement of all slide trays. It also sends commands to system microcontrollers so that they in turn can operate the valves, pumps, motors, heaters and the like at the appropriate times to perform their individual functions within particular modules such as individual workstations and the fluidics module discussed below. Each of the microcontrollers on the several workstations and the fluidics module has a unique address so that they can be identified and individually controlled by the main controller. Communication between the main controller and the several remote modules is accomplished using a serial RS 232 to RS 485 converter which communicates with the microcontrollers through a shared serial bus. The main system or host computer also can include conventional keyboard and mouse inputs and/or a touch screen. The main system computer also can include one or more USB ports and/or an ethernet port, and/or an LCD display, all of which are conventional and commercially available. Accordingly, details of these several conventional inputs and display devices have been omitted.

As mentioned above, each workstation or module can have its own dedicated microcontroller which is networked to the main system controller, which sends high level commands to the individual microcontrollers. The commands can then be interpreted by the workstation microcontrollers, which then operate the valves, motors, pumps, etc. in each module according to a predetermined sequence.

Distribution of control functions to the microcontrollers located on the workstations allows particular manipulations taking place in the workstations to be more accurately timed.

For example, in a working embodiment, a combined de-paraffinizer/stainer microcontroller serves as the electrical interface to the combined de-paraffinizer/stainer workstation for controlling valves for applying bulk reagents and stains supplied by the fluidics module (discussed below) to the slides in the tray. The solvent exchanger also can have a dedicated microcontroller for controlling nozzle manifold movement and fluid delivery to slides. Proximity sensors in the workstations can sense the presence of a tray and the home position of the nozzles to provide feedback to the microcontroller so that it can keep track of and control nozzle position and timing of reagent delivery. Similarly a drying oven workstation microcontroller can provide the electrical interface to the station, and proximity sensors in the station sense the presence of the tray and the temperature in the drying oven to provide feedback to the microcontroller during the slide processing operation.

In the coverslipper workstation of a working embodiment, a microcontroller provides the electrical interface to the coverslipper station or module. Glass coverslips are applied to slides under the control of the microcontroller. Vacuum is monitored by the coverslipper controller using a vacuum sensor, and a drop in vacuum can be used by the microcontroller to detect a situation where a coverslipper is attempting to pick up a broken coverslip. The coverslipper station also can include a microcontroller for controlling an air broom for leveling fluid on the slides, for controlling a motor for moving the coverslip cassettes in and out of the coverslipper and for controlling motors that position the coverslipper head over the cassettes and slides held in a slide tray. Proximity sensors in the station sense the presence of the tray, the home position of the transport mechanism and the position of coverslip cassettes.

An automated fluidics module controller provides the electrical interface to the automated fluidics module, bulk fluid pumps, the baking station radiant heater, the transporter and consumable fluid sensors, which in a particular embodiment include RFID tag readers and RFID antennae.

K. Fluidics Module

A fluidics module can be included in the disclosed system. In one embodiment, the fluidics module can continuously deliver reagents in packaged concentration, in diluted concentrations and/or in bulk to workstations, even as reagent supplies are being replenished, thereby reducing work flow disruptions. In a more particular embodiment, the fluid motivating components of the fluidics module operate on pressure differentials to achieve continuous availability of reagents for delivery from a dispensing means, even during recharge of the dispensing means. In a working embodiment, high pressure is used to drive recharge fluid from a pump chamber into a lower pressure dispense chamber, and the dispense chamber maintains a particular dispense pressure by back-relieving the high pressure used for recharge of the dispense chamber through an air system pressure regulator. Reagent pumps, reagent dilution systems, DI water and alcohol delivery systems all can be operated according to this method.

Figure 25:
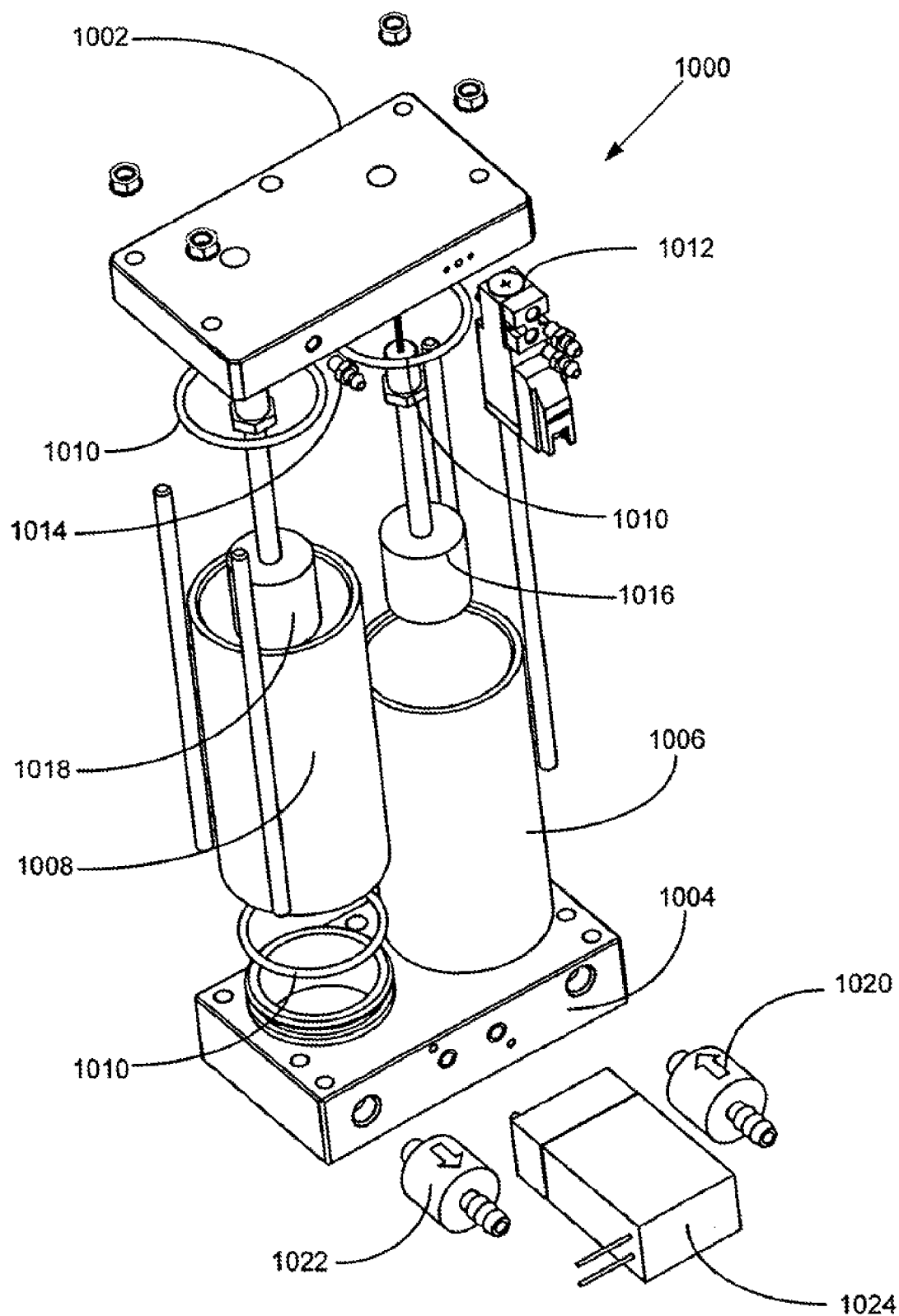
FIG. 25 is an exploded perspective view showing an embodiment of a dual chamber reagent pump.

In a working embodiment, the fluidics module includes one or more dual chamber reagent pumps 1000 as shown in FIG. 25, which can be used to deliver, for example, stains and bulk fluids such as deionized water and alcohol to a workstation. Dual chamber reagent pump 1000 includes an upper manifold 1002 and a lower manifold 1004 (both of which manifolds can be of any material such as metal, plastic or composite, but in a working embodiment are machined from a polyethylene terephthalate, PET, material). A pump chamber 1006 and a dispense chamber 1008 are sealed between the upper and lower manifolds by O-rings 1010, which can be made of ethylene/propylene (EP), Fluorosilicone or other material compatible with liquids handled by the pump. Suitable O-rings can be obtained, for example, from State Seal, Co., Phoenix, Ariz.). The pump and dispense chambers can be of any shape and/or material (such as plastic, metal, composite or glass), and can be sealed to the upper and lower manifolds by any means (such as glued, welded or by compression seal). The material chosen for the chambers is typically a material that exhibits chemical compatibility with a reagent to be dispensed therefrom, and can be translucent to aid in viewing internal fluid levels. However, in a working embodiment, the pump and dispense chambers are formed from a composite material that is compatible with a reagent that is delivered to the system by the pump, and in particular are fiberglass epoxy tubes that are mandrel wound and coated with an ester gel on the inside surfaces to increase their chemical resistance (Amalga Composites, West Allis, Wis.). In alternative embodiments, the chambers are formed (such as by injection molding or machining) from acrylic, polycarbonate, polyethylene, polypropylene or PET materials. The size of the pump and dispense chambers can vary according to the demand for a particular reagent by the system. For example, larger dual chamber pumps are typically employed for bulk reagents such as deionized water or alcohol, whereas smaller pumps can be sufficient for reagents used less frequently or in lesser amounts such as staining solutions.

Upper manifold 1002 of the dual chamber pump of FIG. 25 is connected to 3-way liquid compatible air valve 1012 and dispense pressure inlet fitting 1014. Lower manifold 1004 is connected to inlet check valve 1020, outlet check valve 1022 and transfer valve 1024. Inside of the pump chamber 1006 and dispense chamber 1008 are fluid level switches 1016 and 1018, respectively. In a working embodiment, the fluid level switches are 2-point fluid level switches (high and low; Madison Co., Branford, Conn.).

Figure 26:
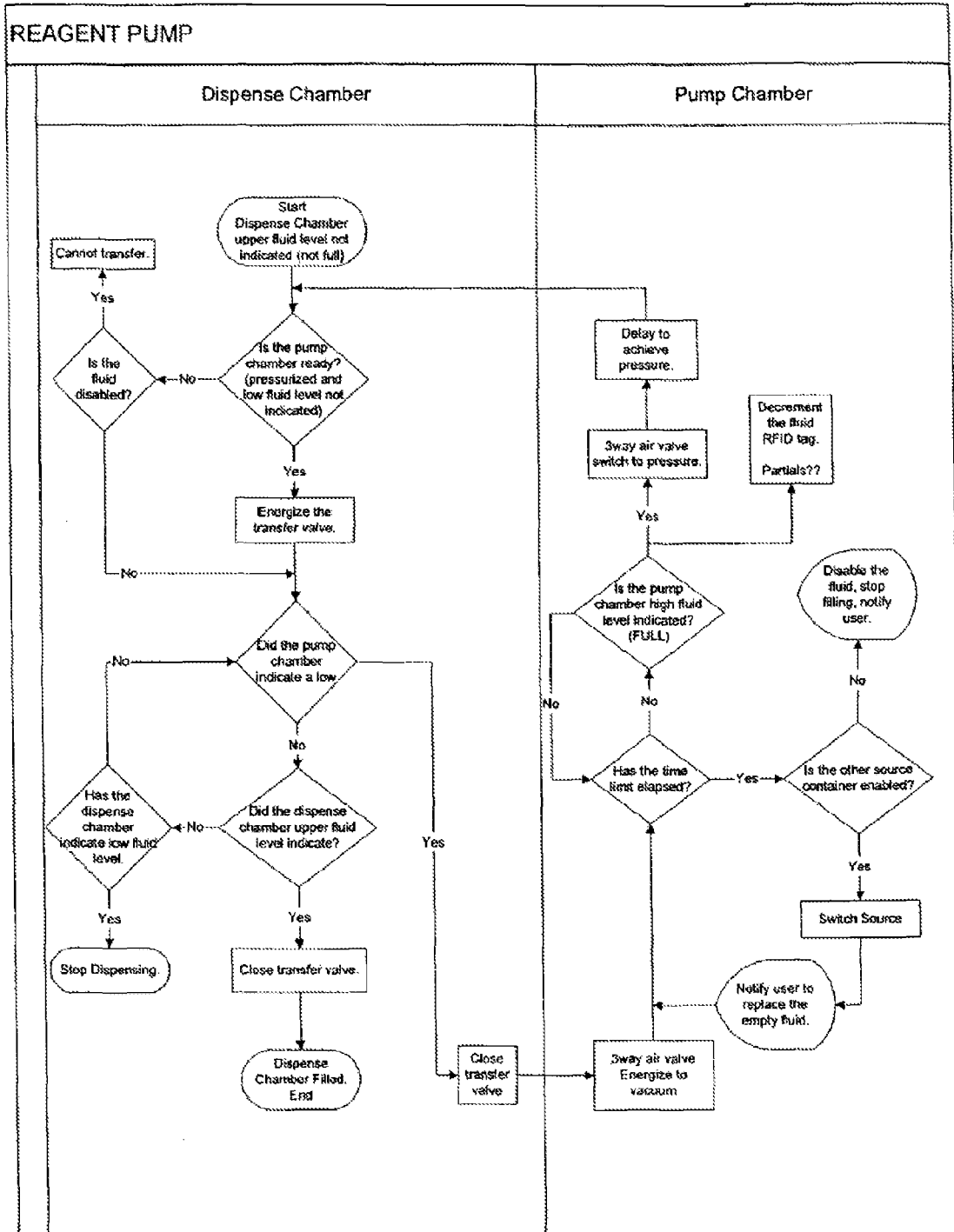
FIG. 26 is a flow chart illustrating a method of operating the pump of FIG. 25 in a manner that enables uninterrupted delivery of reagents to system components even while reagents are being replenished in the system.

In operation, each of the two chambers of the pump is dedicated to a specific purpose. Referring to both FIG. 25 and the flow chart of FIG. 26, fluid levels in the pump chamber are controlled by inlet check valve 1020, 2-point fluid level switch 1016 and 3-way liquid compatible air valve 1012. When the low level switch of 2-point fluid level switch is activated, the 3-way valve selects vacuum, a fluid is drawn into the pump chamber from a reagent supply (such as a bag-in-a-box container discussed below) through the inlet check valve 1020. Once the pump chamber has filled and the high level switch of the 2-point level switch is activated, the air valve switches to high pressure (such as 25 psi). The volume between the high and low switch points can be measured and used to track reagent use by the system, for example, and can be used to determine or verify an empty supply or update reagent data such as reagent data stored in an RFID tag. Control of the pump chamber (such as by the fluidics module microprocessor) also includes a time-out function during recharge; if the time out is reached prior to the high level being activated, the fluidics module switches sources via a source selection liquid valve (not shown) to a second reagent supply (such as a second "bag-in-a-box"). If the time-out is reached again prior to the high switch being activated, the fluid is disabled in the system and a user can be alerted. Backflow to the inlet is prevented by the inlet check valve. Typically, only during a failure would the time-out function on a second container be reached because continuous information regarding remaining volume in a container can be provided to a user, who if alert will have already replaced the reagent in the system.

Transfer valve 1024 links pump chamber 1006 to dispense chamber 1008 through lower manifold 1004, and it is the dispense chamber that dispenses fluid to the system. The dispense chamber is under constant low pressure (such as 15 psi) which is maintained through dispense pressure inlet fitting 1014 by a low pressure supply having an air pressure regulator (not shown). Fluid transfer between the two chambers is initiated by the fluid level dropping below the high level switch of fluid level switch 1018. As fluid is dispensed to the system, the transfer valve opens and fluid passes from the high pressure pump chamber into the low pressure dispense chamber to keep the high fluid level switch in the dispense chamber activated. Dispense pressure is maintained by air pressure back-relieving through the air pressure regulator of the low pressure supply. This process continues until the pump chamber reaches its low switch and is recharged. Fluid leaves the dispense chamber through outlet check valve 1022 to prevent drain back from the system. The constant pressure maintained in the dispense chamber makes it possible to deliver reagent on demand without any interruptions while it is being filled from the pump chamber (dispense chamber can be simultaneously recharged while dispensing). Delivery of reagents to the system is not typically interrupted unless the reagent supply (or supplies) is exhausted, and a low level switch event in the dispense chamber serves as a warning that the dispense chamber has not been recharged. To guard the fluidics module in the event of a failure in the system, distribution chambers for pressure, liquid and vacuum can be employed, and sensors can be used to signal an overflow event by detecting the overflow. Valves can be used to purge overflow to waste during an overflow condition.

Figure 27:
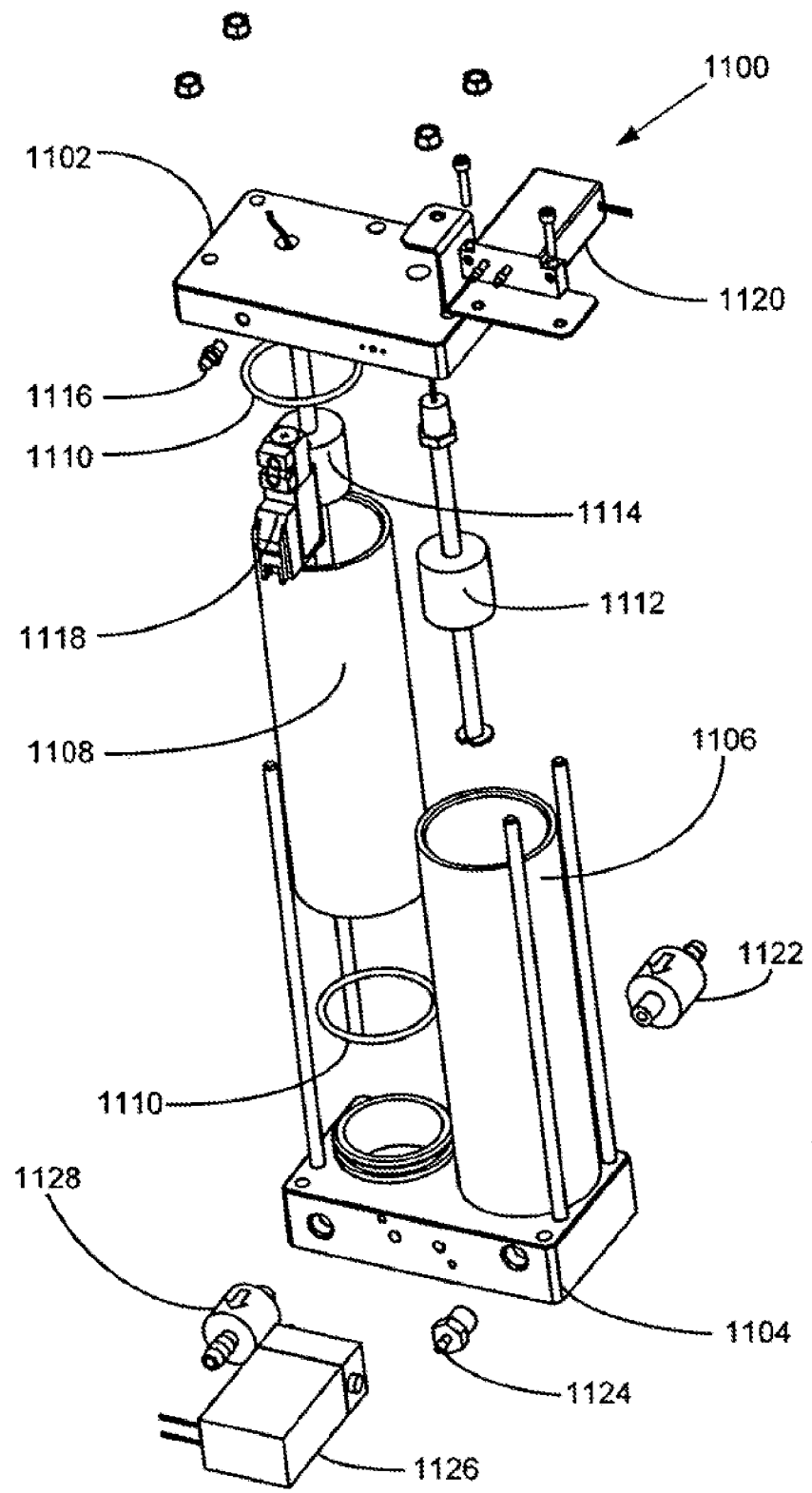
FIG. 27 is an exploded perspective view showing an embodiment of a dual chamber dilution and dispensing pump.

In addition to reagents that can be supplied to the system in packaged concentrations (such as stains like hematoxylin, eosin, EA and OG) other reagents (such as bluing solutions and wash solutions) can be delivered to the system as concentrates and diluted prior to delivery to a workstation. Thus, another component that can be included in the disclosed system is a dilution and delivery system. In a particular embodiment, the dilution and delivery system is configured to continuously deliver reagents at diluted concentration even as the diluted reagent is being prepared from a concentrated solution. A dual chamber dilution and dispensing pump 1100 is shown in FIG. 27 that includes top manifold 1102 and bottom manifold 1104. The bottom and top manifolds are sealed to dilution chamber 1106 and diluted reagent dispense chamber 1108 with O-rings 1110 (shown only on diluted reagent dispense chamber side, but are present on both sides). In a working embodiment of dual chamber dilution and dispensing pump 1100, the chambers are of the same construction discussed above with respect to the working embodiment of the dual chamber reagent pump, but as before, the dual chamber dilution and dispensing pump can be made in any size or shape and from any material, including those discussed above with respect to the dual chamber reagent pump. Inside the dilution chamber 1106 and diluted reagent dispense chamber 1108 are fluid level switches 1112 and 1114, respectively, and which in a working embodiment are 2-point fluid level switches (high and low; Madison Co., Branford, Conn.). Attached to top manifold 1102 are dispense pressure inlet fitting 1116, high pressure/vent valve 1118 and metering valve 1120. Solvent inlet check valve 1122, dilution chamber inlet fitting 1124 (which is connected, for example, by tubing, to metering valve 1120), transfer valve 1126 and outlet check valve 1128 are all connected to bottom manifold 1104.

Dual chamber dilution and dispensing pump 1100 is operated by a method that is similar to that discussed above for the dual chamber reagent pump 1000 of FIG. 25, but with additional steps to prepare a diluted reagent from a concentrate in the dilution chamber 1106. A low switch condition on fluid level switch 1112 in dilution chamber 1106 indicates recharge is needed and activates metering valve 1120 to deliver a pre-determined amount of a concentrated reagent solution to the dilution chamber through dilution chamber inlet fitting 1124. Metering valve 1120 can provide a particular amount of concentrate to dilution chamber 1106 in a time-based manner where the amount is determined by a particular flow rate for a particular amount of time. After metering of the concentrate into the dilution chamber, a solvent such as DI water is delivered to the dilution chamber through solvent inlet check valve 1122 (such as under water system pressure), which remains open until a high switch condition is indicated on fluid level switch 1112. The concentrate and the de-ionized water are mixed in this process, and the solvent check valve also prevents back flow of reagent solution into the solvent supply. High pressure/vent valve 1118 vents dispense chamber 1106 while the concentrate and solvent are added, and then switches to high pressure (such as 25 psi, which can be obtained from the same or different high pressure supply as that used for the dual chamber reagent pump discussed above) to transfer diluted reagent to diluted reagent dispense chamber 1108 once fluid level switch 1112 indicates a high level condition.

Transfer valve 1126 connects dilution chamber 1106 to diluted reagent dispense chamber 1108 through bottom manifold 1104, and it is the diluted reagent dispense chamber that delivers fluid to the system. The diluted reagent dispense chamber is under constant low pressure (such as 15 psi) which is maintained through dispense pressure inlet fitting 1116 by a low pressure supply having an air pressure regulator (not shown, but which can be the same or different from the low pressure air supply and air pressure regulator discussed with reference to FIG. 25). Fluid transfer between the two chambers is initiated by the fluid level dropping below the high level switch of fluid level switch 1114. As fluid is dispensed to the system, the transfer valve opens and fluid passes from the high pressure pump chamber into the low pressure dispense chamber to keep the high fluid level switch in the dispense chamber activated. Dispense pressure is maintained by air pressure back-relieving through the air pressure regulator of the low pressure supply. This process continues until the dilution chamber reaches its low switch and is recharged in the dilution process described above. Fluid leaves the diluted reagent dispense chamber through outlet check valve 1128 to prevent drain back from the system. The constant pressure maintained in the diluted reagent dispense chamber makes it possible to deliver reagent on demand without any interruptions while it is being filled from the dilution chamber (diluted reagent dispense chamber can be simultaneously recharged while dispensing). Delivery of reagents to the system is not typically interrupted unless the reagent supply (or supplies) is exhausted, and a low level switch event in the dispense chamber serves as a warning that the dispense chamber has not been recharged. To guard the fluidics module in the event of a failure in the system, distribution chambers for pressure, liquid and vacuum can be employed, and sensors can be used to signal an overflow event by detecting the overflow. Valves can be used to purge overflow to waste during an overflow condition.

Figure 28:
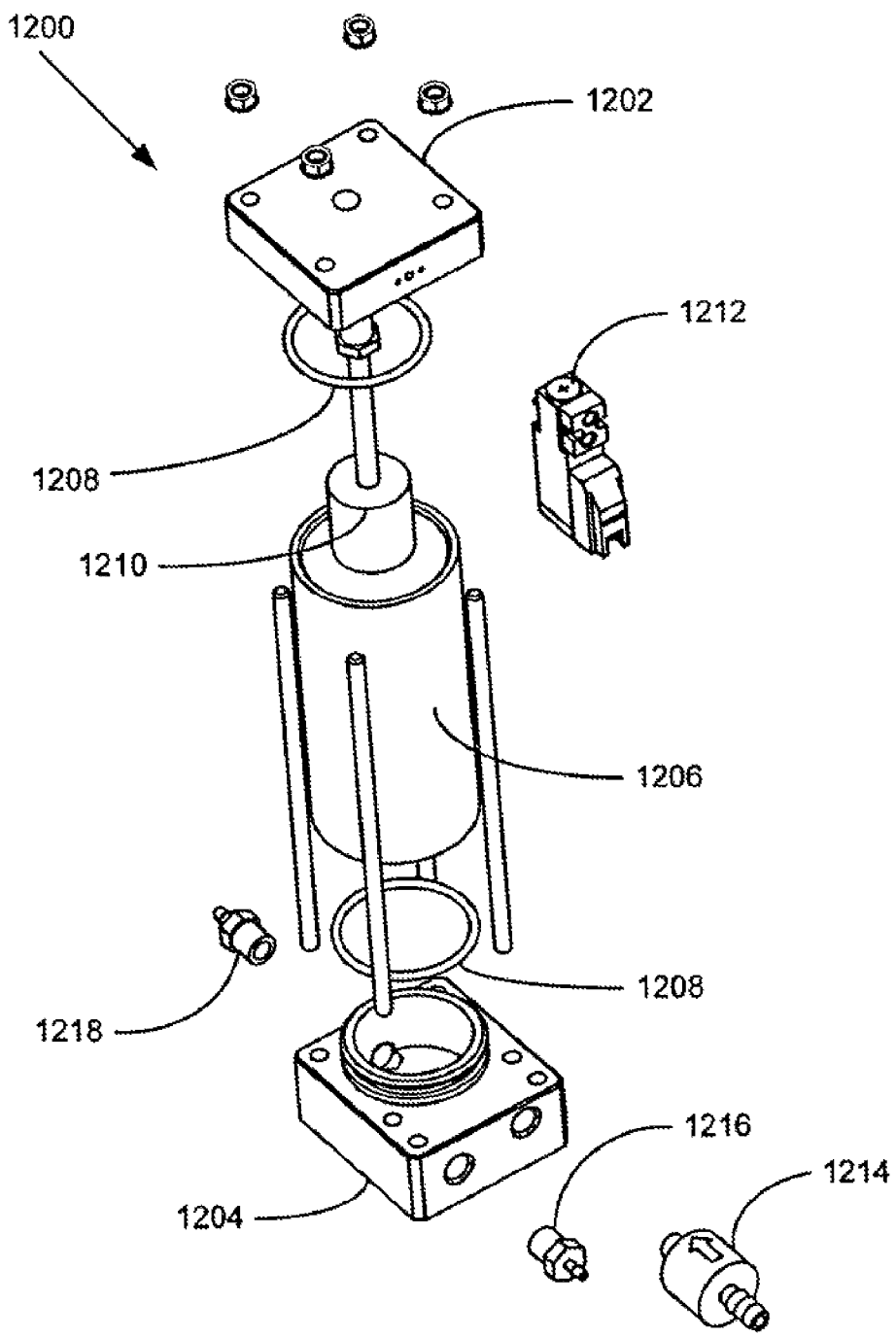
FIG. 28 is an exploded perspective view showing an embodiment of a single chamber concentrate pump.

Concentrated reagent can be delivered to the dilution chamber of the dual chamber dilution and dispensing pump of FIG. 27 using the single chamber concentrate pump 1200 shown in FIG. 28, which is similar in design and function to the pump chamber of the dual chamber reagent pump of FIG. 25. Concentrate pump 1200 includes upper end cap manifold 1202 and lower end cap manifold 1204. Concentrate pump chamber 1206 is sealed to upper end cap manifold 1202 and lower end cap manifold 1204 with O-rings 1208. The concentrate pump chamber can be of any size or shape, and made from any material, for example, the materials already discussed above for the chambers of the dual chamber reagent pump. Inside of concentrate pump chamber 1206 is fluid level switch 1210, which in a working embodiment is a 2-point fluid level switch (high and low; Madison Co., Branford, Conn.). Attached to upper end cap manifold 1202 is vacuum/high pressure valve 1212. Lower end cap manifold 1204 is attached to concentrate inlet check valve 1214, concentrate outlet 1216 (which can be connected to metering valve 1120 of FIG. 27) and concentrate purge outlet 1218.

As indicated above, the single chamber concentrate pump of FIG. 28 can operate in a manner similar to the pump chamber of the dual chamber reagent pump previously described. Concentrated reagent is pushed out of single chamber concentrate pump 1200 under high pressure (such as 25 psi) that is provided to concentrate pump chamber 1206 through vacuum/high pressure valve 1212 until fluid level switch 1210 indicates a low switch condition. Then, vacuum/high pressure valve 1212 switches to vacuum and concentrated reagent is drawn into concentrate pump chamber 1206 until a high switch condition is indicated by fluid level switch 1210, at which time vacuum/high pressure valve 1212 closes. If a high switch condition is not achieved in an allotted time then the reagent supply is switched, and if no fill is achieved, failure is reported, the system stops functioning and a user can be alerted (the time-out value can be reagent specific and stored in a database). The volume between the high and low switch points can be measured and used to track the concentrated reagent consumed by the system, which data can be used to determine or verify an empty supply or to update reagent data such as reagent data stored in an RFID tag.

Figure 29:
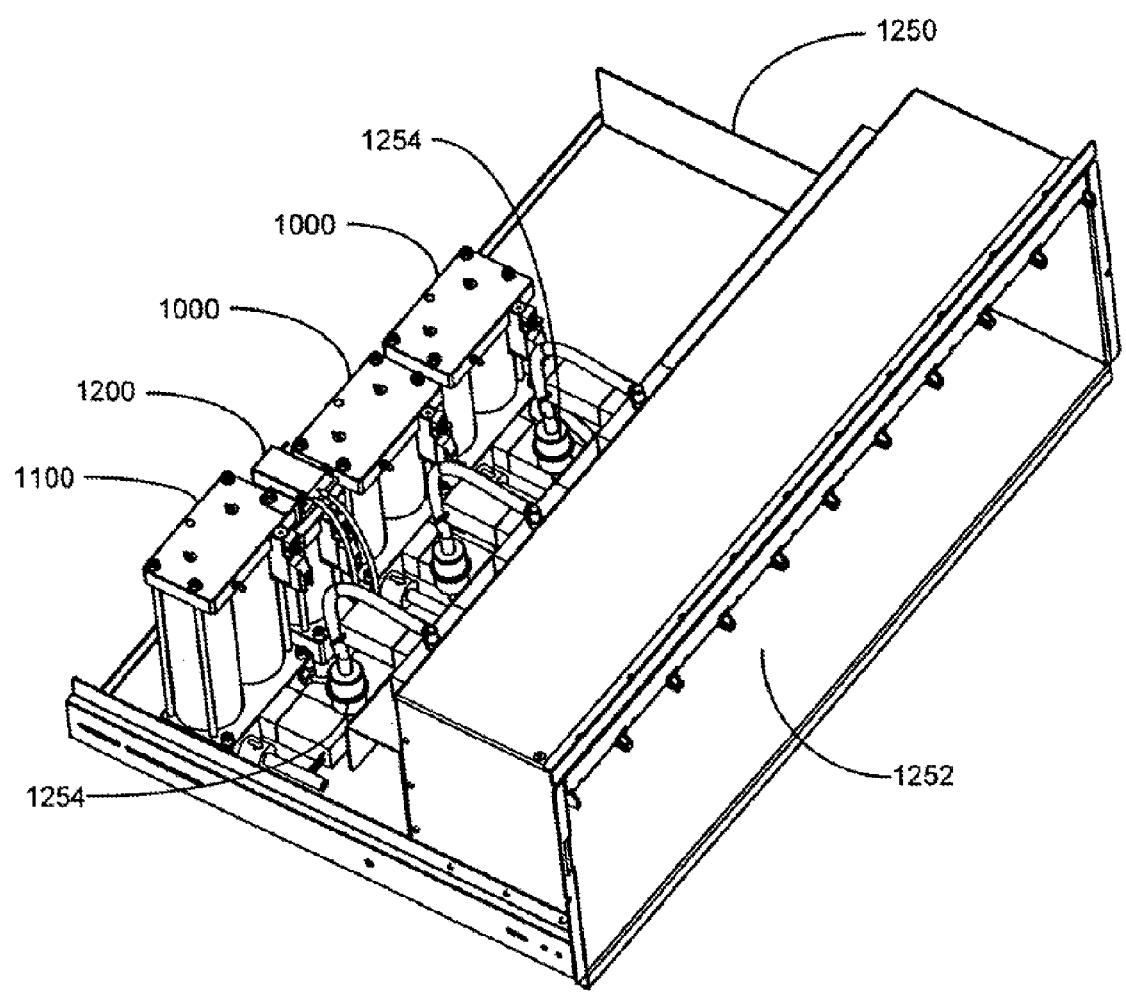
FIG. 29 is a perspective view showing a reagent drawer that can be included in the disclosed system.

Referring to FIG. 29 shows a reagent supply drawer 1250 that can be included in the disclosed system, which drawer can include one or more dual chamber reagent pumps 1000, one or more dual chamber dilution and dispensing pumps 1100 and one or more single chamber concentrate pumps 1200. Reagent supply drawer 1250 further includes a plurality of reagent container slots 1252 for holding a plurality of reagent containers (such as the keyed "bag-in-a-box containers discussed below). Reagent containers placed in reagent container slots 1252 are connected to the various pumps, and inline filters 1254 (such as 45-90 micron filters) can also be included to help ensure that particulates that might be present in a reagent solution will not clog the fluidics module.

Typically, two boxes or containers of each reagent are installed in the instrument. Thus, when one box is emptied, the system may automatically switch over to a new box, and can alert a user so that the empty box may be replaced by a new box without interrupting system workflow. Reagents used in greater quantities, such as fluids used in a solvent exchanger (such as alcohol) or a de-paraffinizer (such as limonene) can be supplied from bulk fluid containers. Deionized water can be supplied to the system from a deionized water source external to the instrument. Wash reagents and solvent exchange reagents can be made by diluting metered concentrates of surfactant, alcohol and/or Limonene with a solvent such as deionized water.

L. Reagent Handling and Storage

A shipping container is disclosed that can be directly installed in the disclosed system (or other biological reaction apparatus) as a reagent supply. The container can include a key or keys for minimizing the potential that a user will inadvertently install the container in an incorrect position in the system, helping to ensure that the correct fluids are pumped to workstations in the system. Since the container can be factory filled, the possibility of spillage by a user also is reduced. A means to store reagent data such as a barcode, a magnetic stripe or an RFID tag also can be included on the container. For example, where an RFID tag is included on the container, the disclosed system can read the RFID tag to further check that the fluid has been installed correctly, and the instrument can update the RFID tag during operation of the system to track reagent use. Data regarding the volume of a reagent pulled from the container by a reagent pump (see discussion above regarding fluidics module) is one example of data that can be used to track reagent use, and such data can be used to determine the amount of reagent remaining in a container. When used in conjunction with the pumps of the fluidics module described above, the disclosed containers are not continually stressed by vacuum or pressure, and are thus less likely to rupture.

Figure 30:
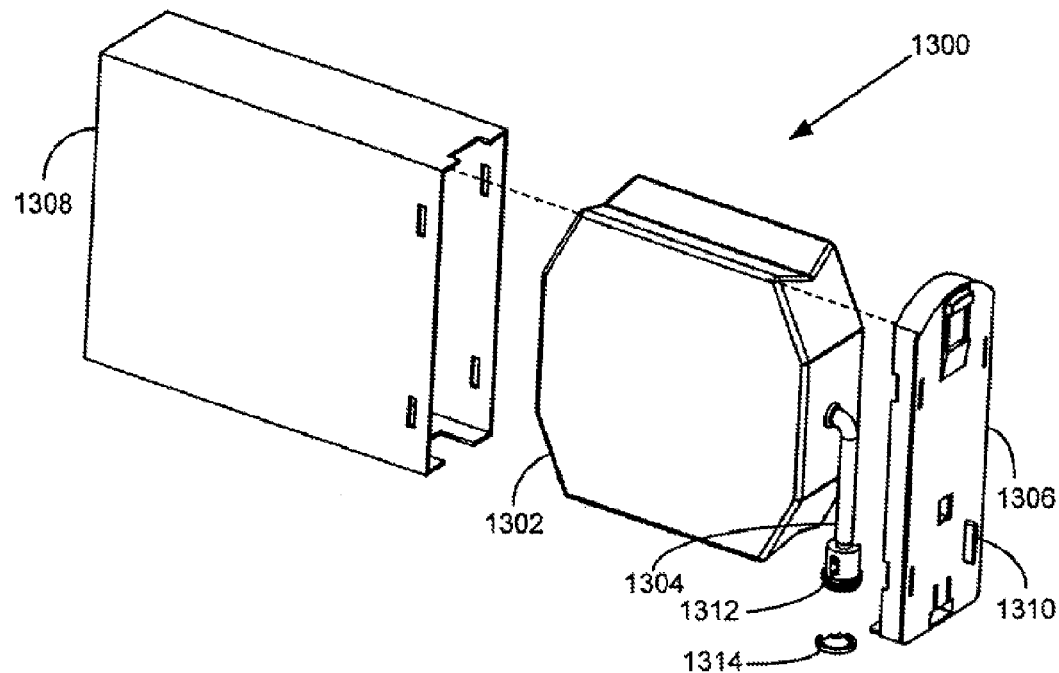
FIG. 30 is an exploded perspective view of a disclosed reagent supply container.

A disclosed shipping/reagent supply container is shown in FIG. 30, which is described generally as a "bag-in-a-box" container. In one embodiment, the container 1300 includes a collapsible, membranous bag 1302, a tube 1304 sealed into the bag, a cover 1306 and a box (such as a paper box) 1308 inside of which the bag fits, wherein the cover and box form a casing inside of which the collapsible bag is contained. The cover typically includes a key 1310 that mates with a corresponding key in a biological reaction apparatus such as the disclosed automated slide processing system. A fitting 1312 that can hold the tube to the cover and an elastomeric seal 1314 can be attached to the end of the tube.

Figure 31A:
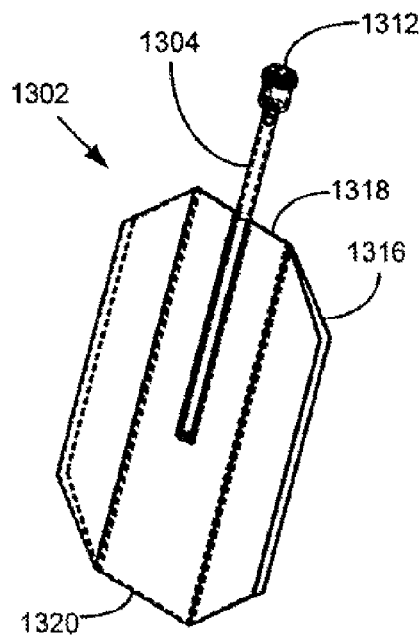
FIGS. 31 A-B are perspective views of a collapsible bag of a disclosed reagent supply container in its unfilled and filled states.
Figure 31B:
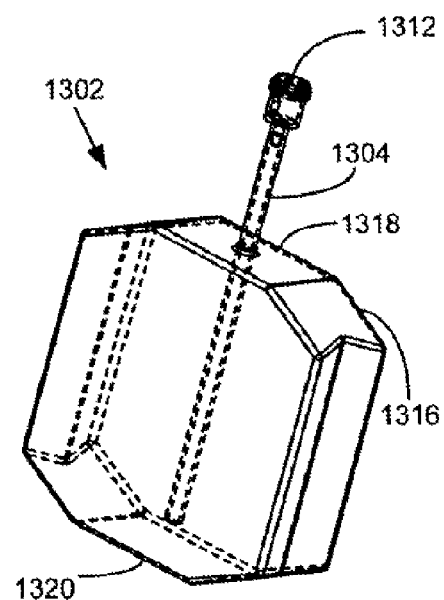

Collapsible, membranous bag 1302 with tube 1304 and fitting 1312 is shown in both its un-filled and filled forms in FIGS. 31A and 31B, respectively. The membrane is folded into an octagonal shape with two wings 1316 on each sidewall, and welded so that it can fold into a flat shape when empty (FIG. 31A), yet expand as it is filled (FIG. 31B). In a working embodiment, the bag expands so that its width is about 25% of its length. As shown, the tube 1304 that is sealed to the top wall 1318 of the bag can extend to near the bottom of the bag 1320 when it is filled. The membrane from which the bag is constructed can be chosen to be compatible with the several fluids that might be used on an automatic staining instrument, and can be chosen to limit diffusion of gases such as oxygen (which helps prevent reagent oxidation) or block light (which helps slow degradation of reagents). These fluids could be, for example, aqueous with a wide range of pHs (such as from pH 3 to 9), or could be alcohol- or aqueous/alcohol-based, such as ethanol n-propanol, or aqueous solutions of ethanol or n-propanol. In a particular embodiment, the membrane is Flexigon™, which is a three layer laminate material (Flexicon, Chicago, Ill.). The inner layer of Flexigon™ that directly contacts the fluid is made from a linear copolymer of ethylene with one or more alpha-olefins (LLDPE), the middle layer is a polyethylene terephthalate (PET), and the outer layer is nylon. Although the size of the bag and the box that contains it can vary, a working embodiment, is 9" long by 5.75" wide with 1" wide interior folds on each long edge which are trimmed at 45° at each corner as shown FIG. 31. The expanded thickness is about 2", and the expanded length and width decrease as the folds expand also as indicated in FIG. 31. The tube 1304 can be made of any flexible polymer, but in a working embodiment, the tube is made from a flexible polyethylene such as Flexelene™ (Eldon James, Loveland, Colo.) and has a total length of 9" of which 6.2" extends inside the top of the bag with the balance outside. The bags are cut, folded, welded (such as heat welded) together and welded to the tube. When the bag is filled, the tube extends to within about an inch of the bottom. The tube 1304 is welded to the top wall of the bag 1318 so that the interior of the bag and interior of the tube are open to the outside only through the top end of the tube.

Figure 32:
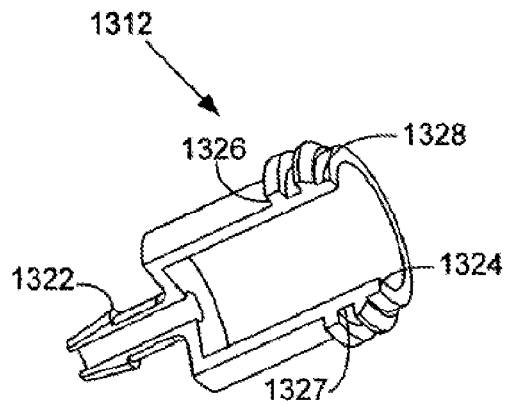
FIG. 32 is a perspective view of a fitting of a disclosed reagent supply container.
Figure 33:
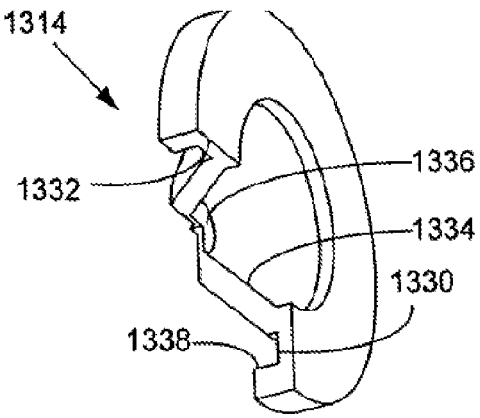
FIG. 33 is a perspective view of an elastomeric seal of a disclosed reagent supply container.

Respectively, FIGS. 32 and 33 show fitting 1312 and elastomeric seal 1314 in greater detail. Fitting 1312 is attached to the tube by barbs 1322 that press into the inside of the tube forming a seal between the barbs and the interior of the tube. On the end of the fitting opposite the barbs 1322 is a face 1324 that is perpendicular to the axis of the fitting and has a smooth surface, such as a surface with no more than 32 RMS variation in surface height. Face 1324 is adapted for mating to an indented face 1330 of elastomeric seal 1314 shown in FIG. 33. These two faces can form a leak-proof connection between the two parts. The normal force between these two parts is formed as a result of the elastic force provided by compressing the elastomeric material of the seal 1314 that is between surfaces 1330 and 1332. This thickness, as molded in a working embodiment, is 0.030", and is compressed to a nominal thickness of 0.008" to provide sealing pressure on the interface between 1330 and 1324. Compression of the elastomeric seal can be accomplished by placing the parts together into the cover portion of the container shown in FIG. 34. For example, the fitting and elastomeric seal can be pressed together and into the cover by engaging indent 1327 of the fitting into lip 1348 on the cover, and snapping surface 1326 against a tab 1342 formed in the cover. Although fitting 1312 can be made from any material, in a working embodiment, the fitting is molded from polypropylene (Advanced Technology, Corona, Calif.). Elastomeric seal 1314 can be made from any elastomeric material, but in the working embodiment the seal is made from an injection moldable material (Santoprene™ 111-35 available from Advanced Technology, Corona, Calif.).

Elastomeric seal 1314 serves to seal a filled bag to prevent its contents from leaking out and to prevent outside contaminates from getting in and to act as a septum which can be fractured when the container is installed into an apparatus, thereby allowing the contents of the bag to be extracted. The septum forms a seal around the piercing tube (discussed below) so that a vacuum can be drawn on the interior of the bag during extraction of the liquid from the bag. The septum feature will now be described. Radially inward from face 1332 starts a conical surface 1334 inclined at about 45° from the axis that leads to septum surface 1336 forming a small disk which is flat and perpendicular to the axis. Conical surface 1334 is thicker than septum surface 1336 (about 0.050" versus about 0.10" in a working embodiment). The reason the material of this small disk is so thin is to provide a weak area where the seal will fracture when stressed by insertion of a piercing tube, leaving the thicker conical surface 1334 to form a seal around the piercing tube. Outer flange 1338 of elastomeric seal 1314, which fits around the mating surface 1328 of fitting 1312, restrains surface 1332 from being able to move radially inward while a piercing tube is stretching conical surface 1334 and septum surface 1336. An advantage of this embodiment is that the seal can be re-used, that is, the piercing tube can be extracted, and the seal will contract to its original position. While this does not revert to a perfect seal, it does not leave an open hole, but rather a slit. Thus, it can be reinstalled on the same or another piercing tube on the same or a different apparatus, forming a good seal and again allowing liquid to be vacuum extracted.

Figure 34A:
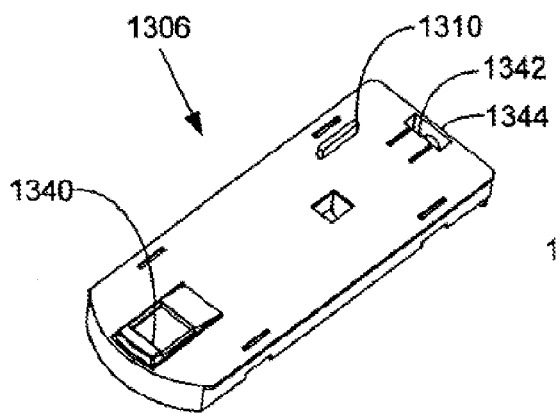
FIGS. 34 A-B are upper and lower perspective views, respectively, of a cover of a disclosed reagent supply container.

Cover 1306 of a working embodiment of the disclosed container is shown in more detail in FIG. 34. As shown in FIG. 34A cover 1306 has a key 1310 formed onto its top, the purpose of which is to prevent the container, which contains a specific reagent, from being placed into the wrong position in the disclosed system and thereby delivering an incorrect reagent to a workstation of the system. For example, in a working embodiment, interference fit keys of differing position that mate into mating slots in a reagent supply drawer of the system provide this function. The key in the working embodiment extends upward about 0.20" from the top surface of the cover and is about 0.10" wide and 0.75" long. However, it is the position of the key relative to the sides of the cover that determines which slot the cover will mate with in the reagent drawer. In the working embodiment, there are eleven different positions that key 1310 can have, and each distance is correlated with a different reagent that is to be placed in the bag. There are eleven matching slots on a reagent supply drawer of the system (not shown) that allow only the appropriate bag-in-a-box to be installed into the system in a certain position. The cover can further be color-coded, and the same color can indicate the proper position on the system for a container holding a certain reagent. A further feature of a working embodiment of cover 1306 is retaining tab 1340. The front surface of the retaining tab is inclined so that as the assembled bag-in-a-box containing a reagent is installed into the system, another mating surface (also not shown) pushes the tab down, and when the box is seated and the piercing tube has pierced the septum, the tab snaps up behind the mating surface, thereby retaining the box in the system. To remove the box, the tab is depressed. Surfaces 1342 (on the end of the flexible tab) and 1344 are the surfaces that provide the compression force between the elastomeric seal and the fitting as they are pressed into the cover. Lip 1348 engages indent 1327 of the fitting as the elastomeric seal and fitting are pressed into the cover during assembly.

Figure 34B:
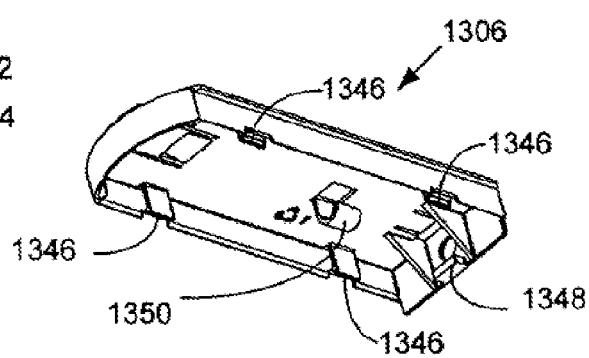

As shown in FIG. 34B, cover 1306 also can include a plurality of clips 1346 that engage holes in the box portion of the container (shown but not labeled in FIG. 30) to hold the cover on the box. A hook 1350 formed in the cover also can be included to hold the tube portion of the container in place under the cover. Although the cover can be formed in a variety of ways from a variety of materials, a working embodiment is molded from Cycolac ABS MG38 (Advanced Technologies, Corona, Calif.).

Figure 35A:
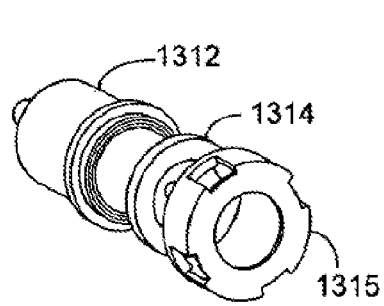
FIGS. 35 A-B are a perspective and cut-away view of an alternative septum/fitting combination for use in a disclosed reagent supply container.
Figure 35B:
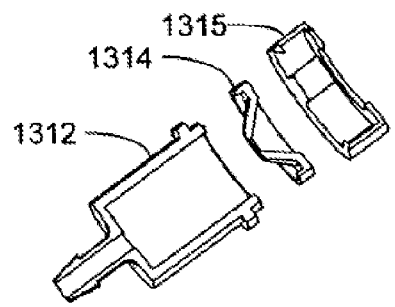

FIGS. 35A and 35B shows two views of an alternative embodiment of a fitting and septum combination for a bag-in-a-box container that does not require the cover portion to have tabs to hold the fitting and septum together. Rather, as shown in FIGS. 35A and 35B, a simplified fitting 1312 is used and septum 1314 is held onto the fitting using a septum cap 1315. Septum cap 1315 can include tabs that engage the lip on fitting 1312 or can simply be crimped onto the fitting as is standard practice for septum vials.

Figure 36:
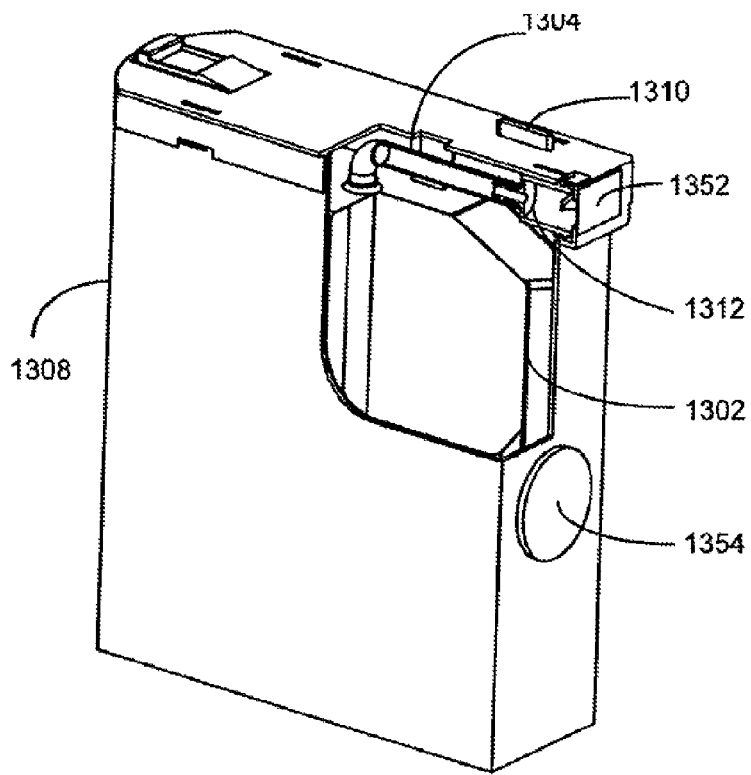
FIG. 36 is perspective view of a disclosed reagent supply container as assembled.

An assembled container is shown in FIG. 36. The components are indicated as before, with two additional features, namely, an optional sealing tape 1352 and optional RFID tag 1354. Collapsible bag 1302 can be easily filled by hanging it from the fitting 1312 and pumping the desired fluid into the bag. The filled bag can then be assembled to the elastomeric seal, and the fitting and seal are pressed into cover 1306 as described before. Tube 1304 is then draped over the hook of the cover and the entire assembly is inserted inside box 1308. The box can be made of many different materials, but in a working embodiment is made from B flute cardboard (Triple A Containers of Cerritos, Calif.). Cutouts can be provided at the top of the box to provide clearance for the fitting and elastomeric seal, and for the retention tab. Sealing tape 1352 can be applied to prevent debris from getting into the elastomeric seal during shipping. RFID tag 1354 can be adhered to the surface of the box as shown, and can function to keep track of how much fluid remains in a bag and to serve as a second check on whether the correct bag is inserted into a specific reagent slot in the system. An RFID antenna in the system can read the RFID tag of the installed container.

Figures 37A, 37B:
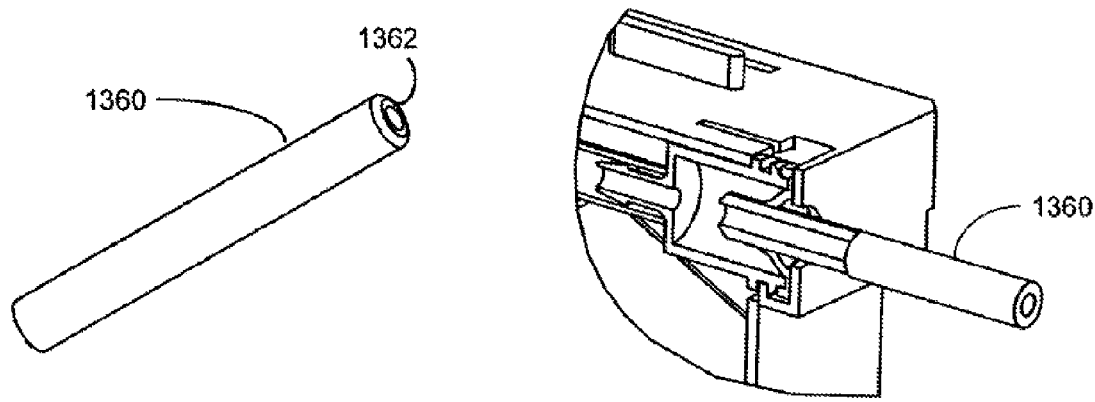
FIGS. 37 A-B are, respectively, a perspective view showing a piercing tube and a perspective view showing a piercing tube inside of a disclosed reagent supply container.

A piercing tube 1360 is shown in FIG. 37A that can be installed in the disclosed system, for example, at the back of a keyed reagent drawer and connected to the components of the fluidics module. The end 1362 of the piercing tube that pierces the septum has a radius but is not so sharp as to injure a user who might accidentally contact the piercing tube. Nonetheless, the interaction between the piercing tube and the elastomeric seal is such that, as the piercing tube is inserted into the conical portion of the elastomeric seal 1334, the wall of the cone does not thin significantly. However, the flat surface of the septum portion 1336 is thin, and it stretches and ruptures forming a relatively small hole. The thicker cone portion then elastically expands around the piercing tube, allowing it to pass through and forming a seal (see FIG. 37B) around the piercing tube 1360 that is sufficient to allow a vacuum to be formed inside the bag while a reagent is extracted from the bag.

Figure 38:
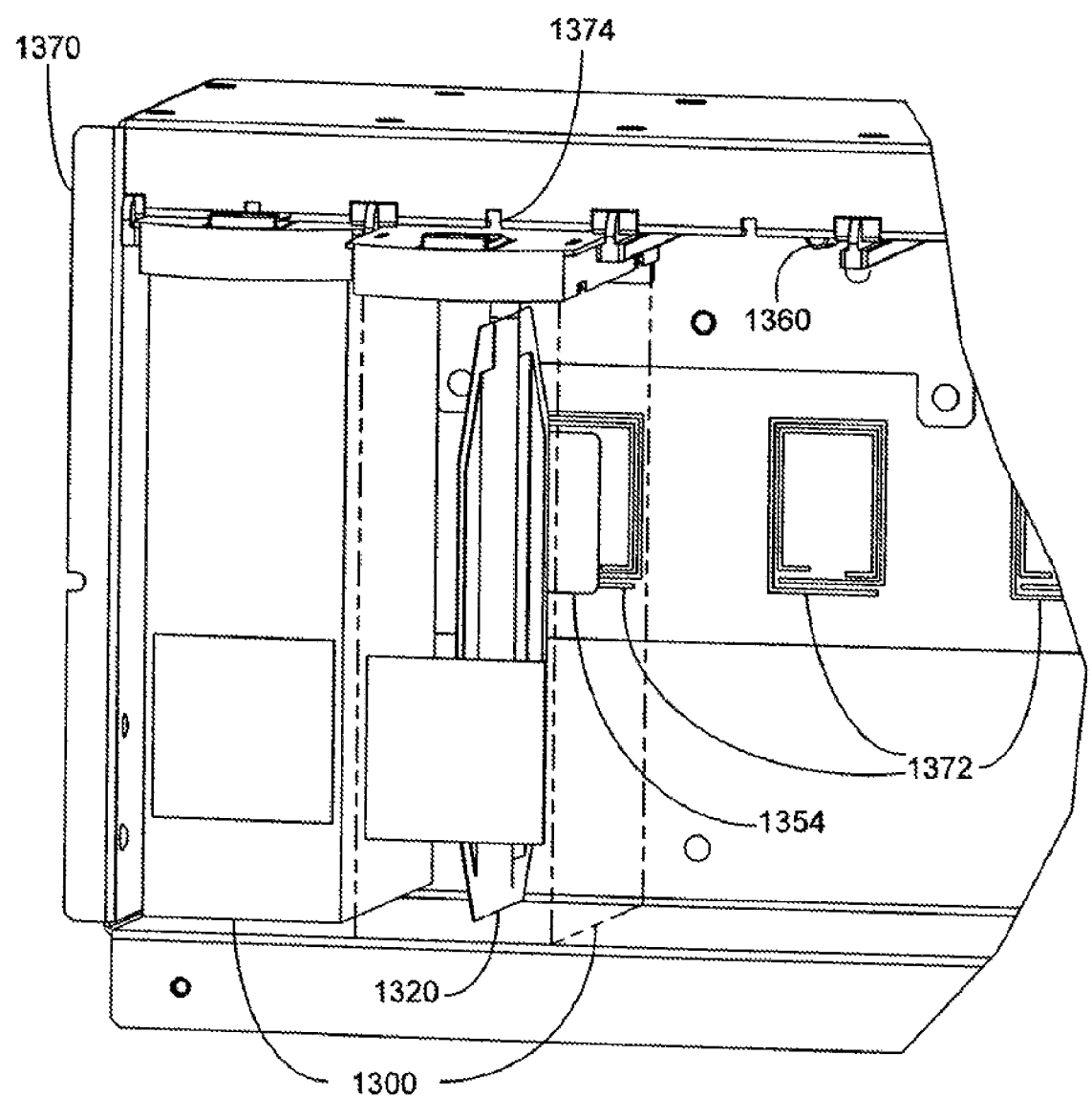
FIG. 38 is a perspective view showing a disclosed reagent supply container mounted in a reagent drawer of the disclosed system.

FIG. 38 shows a pair of bag-in-a-box reagent containers 1300 mounted in a reagent drawer 1370 of a working embodiment of the disclosed system. The walls of the bag-in-a-box on the right are shown in transparency so that collapsible bag 1320 can be seen, as well as RFID tag 1354, which is located at the back of the box. As can be seen in FIG. 38, RFID tag 1354 is located next to a RFID antennae 1372 when bag-in-a-box 1300 is mounted in reagent drawer 1370. FIG. 38 also shows an interference key slot 1374 that mates with a key on a bag-in-a-box container, and a piercing tube 1360 located at the back or reagent drawer 1370 that pierces a septum and connects a bag-in-a-box container to a fluidics module of the system.

M. Consumables Tracking

In a particular embodiment, a system and method for using read/write enabled RFID tags to manage reagents in the disclosed automated slide processing system also is provided. In this embodiment, one or more reagent containers and coverslip cartridges include self-contained read-write memory devices affixed thereto for keeping track of data related to the container or cartridge. The memory device may be a "touch memory" device such as a DS 1985 F5 16 Kbit add-on touch memory EPROM (Dallas Semiconductor Corporation, Dallas, Tex.) such as disclosed in U.S. Patent Application Publication No. 2002/0110494, which is incorporated by reference herein. However, in one embodiment, lot-controlled consumables (reagents and glass coverslips) have an RFID tag embedded in a label attached to their respective containers. While RFID chip tags may be used, i.e. RFID tags containing a microchip, chipless RFID tags are of significantly lower cost. During the manufacturing and packaging process, product and container-specific manufacturing data can be recorded on both the label and in the embedded RFID tag. In the case of the RFID tag, this manufacturing data can include, for example the following:
1) Catalog or part number,
2) Lot number,
3) Container serial number,
4) Catalog package name,
5) Bulk fluid name for reagents,
6) Volume in milliliters for reagents or coverslip count for glass coverslips,
7) Expiration date, and
8) Manufacturing data (such as date/location of manufacture)

The manufacturing data in the RFID tag typically will be encrypted and then encoded to allow automated transmission error detection and correction before being written to the tag. After the write, the sections of the tag that store this manufacturing data are write-protected to prevent alteration and misidentification.

Once the consumable having an RFID tag is loaded on the instrument, the software can access a consumable's RFID tag through an on-board RFID reader and antennae. (It should be noted that while RFID reader is the common term used for the device, it will be understood that an RFID reader provides both read and write access to RFID tags). Typically, the disclosed instrument will have one antenna at each possible location where a consumable can be loaded. See, for example, FIG. 38.

These antennae are connected to the RFID reader through a multiplexor controllable by software commands. Each antenna is designed to only provide access to an RFID tag at its specific location. Thus, the software can switch the RFID-reader to a specific consumable location and read from and write to the RFID tag on that specific consumable whenever required. One suitable RFID tag, which is commercially available is the Tag-it™ HF-1 transponder Inlay Rectangle RFID tag available from Texas Instruments, Dallas, Tex. The RFID tag may be affixed to or incorporated into the fluid container or cartridge and contains information pertaining to the contents of the fluid container or cartridge such as the contents, type, lot number, expiration and related information. The RFID tag enables communication between the container or cartridge and the system processor, thus adding an element of intelligence to the overall system. The RFID tag includes a memory device which can be mounted on the container or coverslipper cartridge. The memory device functions to initiate the system for each new fluid container or coverslipper cartridge that is presented to the system, and to keep track of the fluid or coverslip slide covers remaining. In operation, the memory device is initially read in the information regarding, e.g., type, volume, type, lot number, expiration and related information in the case of the fluid containers, or number and type of coverslips, etc. in the case of a coverslipper cartridge holder. An RFID antenna is positioned behind each of the boxes and also the coverslipper cartridge to read each of the tags and send a signal to the host computer.

During normal tray processing, a Run Time Executive application may access the RFID tags for a variety of reasons. For example, the initial access to each RFID tag typically may be used to confirm the presence of the consumable and that it can be used; i.e., that the contents have not expired. From that point forward, the Run Time Executive can treat the RFID tags as ancillary memory. Using the memory space, the Run Time Executive records the initial date the consumable was used and the identification of the instrument on which it was first registered. Thus, consumables may be moved from instrument to instrument. As the contents of the consumable are used, the memory space is updated with the current estimated remaining or consumed volume or count, along with the date of the last update and the instrument's identification. The Run Time Executive both assesses and maintains this on-board inventory of consumables so sufficiency of the consumables can be ascertained to determine if all trays loaded into the system can be processed. The Run Time Executive also keeps the operator or user informed as to the estimated capacity for slides in terms of consumables, and can automatically reorder reagents from a supplier when reagents are close to being depleted.

Thus, a user is free to remove or replace any consumable on the instrument at any time during processing, or when the instrument is powered off. By using the RFID tag's memory space to store information about the current contents, a previously removed consumable can be re-loaded and the Run Time Executive is able to track the consumable's contents from where it left off. Furthermore, when RFID tags are used during reagent manufacture as described below, and reagents are scanned into an instrument(s) for use therein, it is also possible to track reagent use on a laboratory-wide basis, and enable automatic re-ordering of reagents as a laboratory's supply is depleted, even when the reagents installed on a given instrument are full, but represent the last few remaining in a laboratory.

N. RFID Tag Use During Reagent Manufacturing

Lot-controlled consumables (such as reagents and coverslips) can have an RFID tag embedded in a label attached to their respective container, and such labels can be prepared and attached during manufacturing. In one embodiment, the process utilizes a standard PC, a computer program (that can, for example, provide encryption during label preparation), a database, and a device referred to as an RFID printer. The RFID printer simultaneously prints a paper label and writes to a RFID tag, and also is capable of reading RFID tags. Typically, each RFID tag also is uniquely identified by a number. A bar code scanner optionally can be connected to the PC and employed for data entry. This scanner can be connected such that its data is input to the computer via the keyboard. The process described below is an exemplary sequence of steps that can be used during reagent manufacture:

Prior to starting the computer application, the user loads the RFID Printer with a sufficient quantity of labels/tags. The labels/tags are in a roll and the RFID Printer advances the roll one label/tag at a time. The user then starts the computer program (also referred to as the application) and logs in. The user's name and password are confirmed in a database table so that only authorized users can proceed. The user identifies the product for which labels and RFID tags are to be prepared, including both the product's catalog number and the specific manufacture lot number. This information is keyed into a form presented on a screen by the application. Alternatively, this information can be in bar code form and scanned with a bar code scanner.

The application reads product data from the database using the entered catalog number as a unique database key. Product data can include the catalog package name, the product's bulk fluid name for reagents or coverslip name for coverslips, the package's volume in milliliters for reagents or coverslip count for coverslips, date of manufacture, product expiry date, the usable period of the product after date of first use (such as in units of days), the label type etc. In addition, the application can determine the last container serial number used by accessing container data stored in the database, and if none is found, the last container serial number is initialized to zero. The user then enters the quantity of labels and tags to prepare—one for each container. Alternatively, this quantity can be in bar code form and scanned with a bar code reader.

The application loop then can perform each of the following sub steps until the desired quantity of labels and tags have been prepared:

1. Compute the next container's serial number by adding the loop counter to the last container serial number as determined from the database.

2. Using the RFID Printer, read the unique identification number of the RFID tag in the current print position.

3. Assemble the data to be written to the RFID tag. Exemplary types of product/container data are catalog number, lot number, container serial number, catalog package name, bulk fluid name for reagents, volume in milliliters for reagents or coverslip count for coverslips, usable period in days, expiry, and manufacture date.

4. Encrypt the data using the RFID tag's unique identification number as the encryption key. This helps prevent production of unauthorized copies of an RFID tag and ensures data integrity between the physical labels and the database.

5. Encode the encrypted data using an error correction encoding scheme (such as a Reed-Solomon error correction encoding scheme). This helps ensure reliable data transmission from the RFID tag to the instrument on which the container is installed.

6. Assemble data to be printed on the label. The specific data are listed below.

7. Combine the label data and the tag data into a single data packet.

8. Send the data packet, along with appropriate commands, to the RFID Printer. This causes the label to be printed, the tag to be written and write-protected, and the label/tag to be advanced one print position. The label type is not printed, but is used to trigger the printing of graphics stored in the RFID Printer's memory that are specific to the product.

9. Write a record to the database which represents the physical container, such record containing product/container data and timestamp.

10. The application then cycles back to Step 3 to allow the user to enter data for other containers.

O. Waste Emulsification

Figure 39:
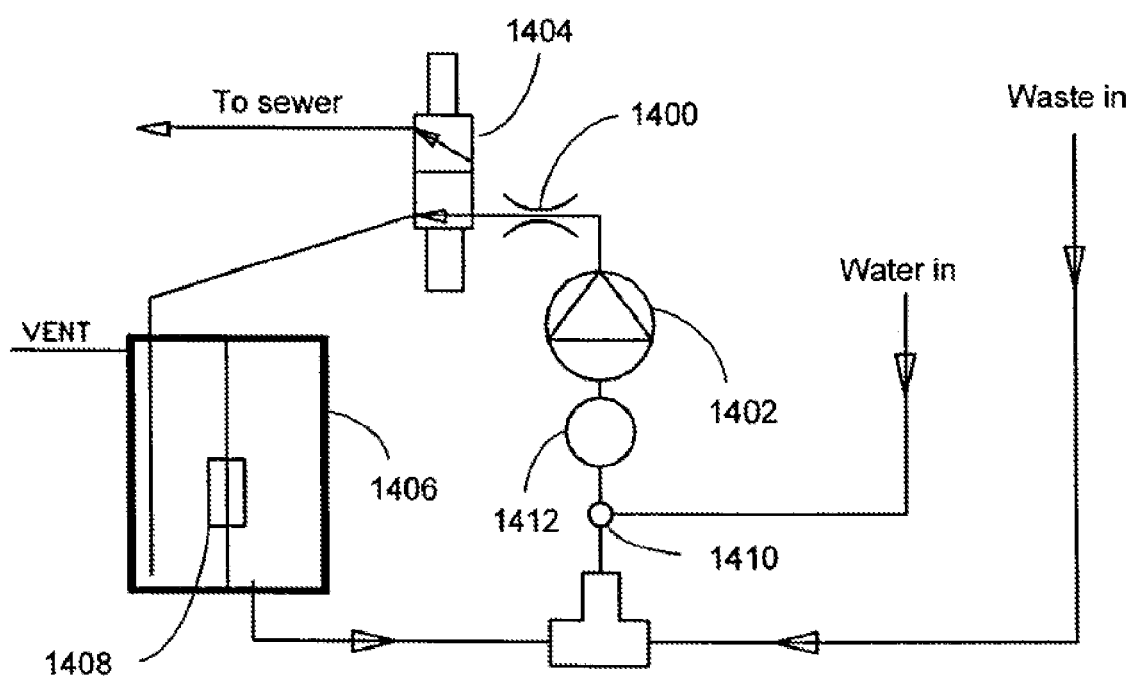
FIG. 39 is a schematic diagram of an embodiment of a waste emulsification scheme.

In a particular embodiment, non-toxic waste solvents such as limonene and ethanol can be emulsified and disposed of through a drain to a municipal water treatment plant. A mechanical emulsification apparatus that can be included in the disclosed system is shown in FIG. 39. Waste streams from workstations are collected and pumped through a small restrictor 1400 at high velocity by pump 1402, which generates high shear forces in the fluid that breaks immiscible liquids into small enough droplets that their surface tension keeps them from agglomerating and their motion is determined by surface forces (Brownian motion) rather that body forces (buoyancy/gravity). A diverter valve 1404 can either send the emulsified waste to the sewer or into waste container 1406. Cycling of a fluid a few times through the restrictor improves emulsification, so typically, waste is continuously cycled into the waste container 1406 until the waste container is full as indicated by float switch 1408. Once the waste container is full, water can be added to the emulsified waste to dilute it at valve 1410 as diverter valve 1404 sends the waste stream to a sewer system. Mesh filter 1412 can be included in the emulsification system to prevent debris from clogging the pump and the restrictor.

P. Tray and Slide Tipping

Figure 40:
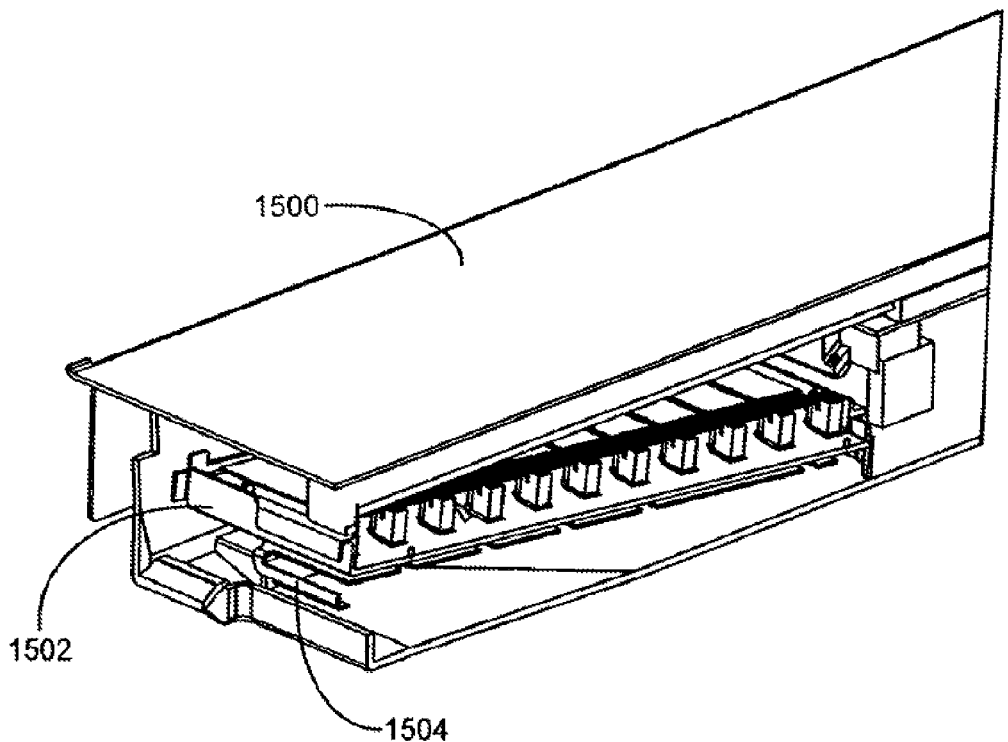
FIG. 40 is a perspective diagram showing an embodiment of an apparatus for, and a method of, removing reagents from slides in a slide tray.

As illustrated in FIG. 40, one disclosed method for removing reagents from slides and/or a slide tray is to tilt a slide tray 1502 within a workstation 1500 using a tilt pan 1504 to tilt one end of the tray upward. Tray tilting can be done prior to removing a slide tray from a workstation or at any time during slide processing by a workstation. In one embodiment, tray tilting can be accomplished using a transporter, which engages the tilt pan lip (such as an X-hook of an X-Y shuttle table) and then lifts the tilt pan (such as with the Z-elevator) and lifts the tilt pan. Alternatively, a separate mechanism can be provided in a workstation to raise a tilt pan within a workstation.

Figure 41A:
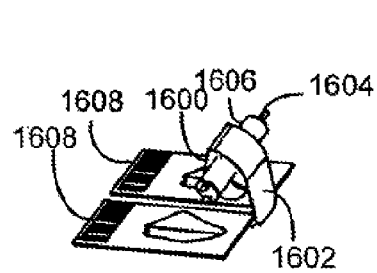
FIGS. 41 A-B are diagrams illustrating an alternative apparatus for, and a method of, removing reagents from slides in a slide tray.
Figure 41B:
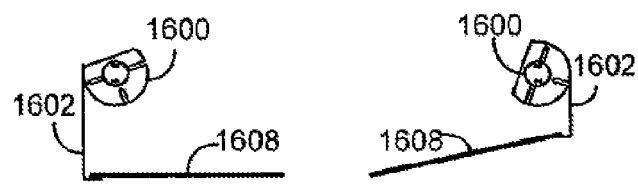

Another method that can be performed to remove reagents from individual slides is to tilt the slide themselves. A particular system and method for lifting slides is shown in FIG. 41. As shown in FIG. 41A, a sector 1600 can be carried on a track (not shown) to position a ribbon 1602 underneath one or more individual slides 1608. A motor 1606 is mounted on a locked shaft 1604. Motor 1606 lifts one end of the slide or slides upward by rotating sector 1600 and wrapping ribbon 1602 around the sector, thereby lifting the slide or slides 1608 as shown in FIG. 41B.

Q. System Control and Electronics

Figure 42:
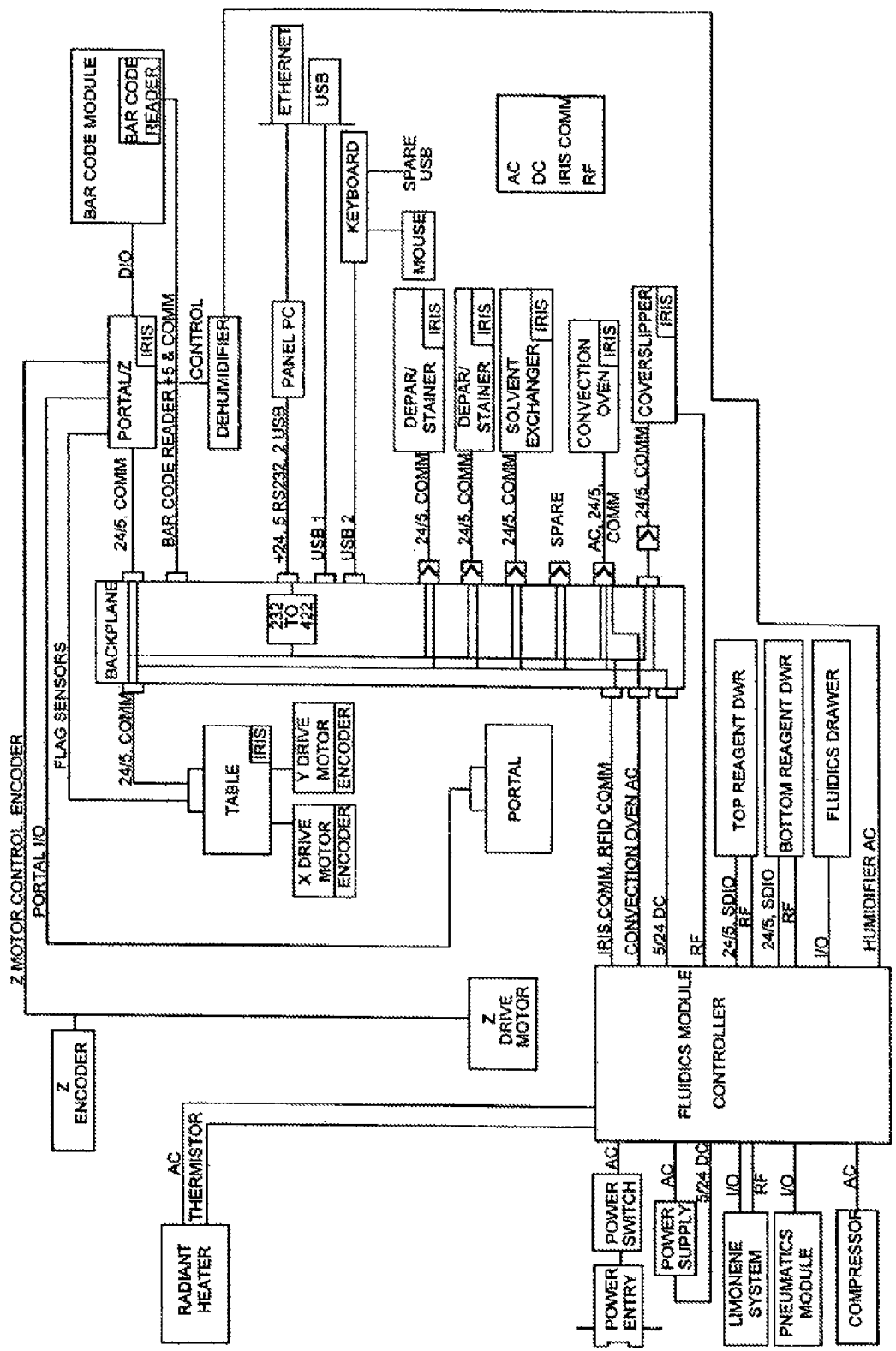
FIG. 42 is a schematic diagram showing electrical and communication connections of a working embodiment of the disclosed slide processing apparatus.

FIG. 42 shows a diagram outlining the electrical and communications connections used in a working embodiment of the disclosed system. The system's main control computer includes a PC running a standard Windows™ operating system. The PC serves as the interface to the user [so, for example, the user can design, control and/or expedite (STAT) the processing of each slide/slide tray, monitor the progress of the process, and be alerted to system conditions requiring attention] and functions as the master controller of the high level system functions. In one embodiment, the PC provides one-touch operation for a user defined default protocol.

Multiple microcontrollers that serve as the interface between the main PC and the low level system functions can be connected to the main computer (for example, via a shared serial RS485 communications bus). Microcontrollers can be allocated between system components, for example, one microcontroller can be allocated to each of several components (such as to each of several workstations, for example, each of a combined de-paraffinizer/stainer, a solvent exchanger, and a coverslipper) or allocated to multiple components or subcomponents (such as a portal and an elevator of a transporter). Such microcontrollers, also known as an IRIS (Independent Remote Input/Output System) can manage the electrical and electromechanical devices within a given system module, workstation or component. A third layer of microcomputer hardware can be implemented where fast and precise mechanical motion is desired (such as for controlling a moveable nozzle assembly). The third layer can include a microstepping motor controller, which includes a dedicated microcontroller and a motor driver that moves a stepping motor in response to serially transmitted commands from the IRIS.

While it is possible to add interface PC boards to a PC to directly connect low level devices such as valves and motors, the separation and isolation of the PC and the low level devices with the IRIS relieves the PC of the burden of low level functions such as fast valve operation and motor microstepping. Separation of the functions helps to increase timing accuracy at the device level since clock functions in the IRIS are not disrupted by other tasks as they can be in a PC. In a working embodiment, the PC delivers sets of instructions for controlling system components in the form of a macro that is used by the IRIS to control lower level functions of system components. The PC can also be connected to a larger laboratory information system (such as the Ventana Lab Manager and/or the Ventana Interface Point, Ventana Medical Systems, Inc, Tucson, Ariz.).

In a working embodiment, an IRIS includes a single printed circuit board employing a microcontroller (such as Microchip Corporation part number PIC18F452, Chandler, Ariz.) with sufficient memory and speed to:

1. Communicate with the main PC over a serial communications link.
2. Operate up to twenty-four valves, DC motors, relays or similar devices.
3. Monitor up to twenty digital devices, such as optical and Hall-effect proximity sensors.
4. Monitor up to eight analog devices such as pressure and temperature sensors.
5. Control up to four stepping motors, each via its own serial communications link.
6. Monitor the output of a motor encoder circuit (a second microcontroller on the IRIS can be dedicated to this function) to confirm the rotation of the stepper motors under its control.

A working embodiment of a microstepping motor controller similarly employs a microcontroller (such as Microchip Corporation part number PIC18F258, Chandler, Ariz.) which accepts motor move commands from the IRIS. The motor controller desirably has sufficient speed and computing power to microstep a motor at step rates of up to 16,000 steps per second, and can accurately control acceleration and deceleration of an inertial load without step loss.

P. Aspects and Alternative Embodiments

In one aspect, an automated slide processing system is disclosed that includes at least one slide tray holding a plurality of slides in substantially horizontal positions and one or more workstations that receive the slide tray and perform a slide processing operation on a slide in the slide tray while the slides remain in substantially horizontal positions. In particular, a workstation in the system can dispense a reagent to slides in the slide tray without a substantial amount of the reagent that contacts a first slide contacting a second slide, thereby minimizing cross-contamination between slides, and the system can further include a transporter to move the slide tray into and out of the one or more workstations. In particular embodiments, the one or more workstations can include a radiant heater, a combined de-paraffinizer and stainer, an automated coverslipper, a drying oven, a solvent exchanger and/or a combined de-paraffinizer/stainer/solvent exchanger. Where two or more workstations are included in the system, they can be arranged in a directly vertical stack.

In one particular embodiment, a system is disclosed for complete processing of slides from baking through coverslipping. Such a system includes a plurality of workstations including a combined de-paraffinizer/stainer/solvent exchanger, a radiant heater, a drying oven and a coverslipper, at least one slide tray holding a plurality of slides in substantially horizontal positions, and a transporter for moving said slide tray between said plurality of workstations.

In another aspect a method is disclosed for automated processing of a plurality of biological samples on slides wherein the slides are held in substantially horizontal positions in a slide tray. Such a method includes moving the slide tray to a first workstation, staining the samples on the slides in the first workstation, moving the slide tray to a second workstation, and coverslipping the slides in the second workstation. Moving the slide tray can include moving the slide tray with an X-Y-Z transporter, and the slides can remain in substantially horizontal positions in the slide tray throughout processing by a workstation(s).

In a particular embodiment, the disclosed method can further include de-paraffinizing the samples in the first workstation, for example, by delivering a de-paraffinizing fluid such as limonene to the samples. In other particular embodiments, staining can include dispensing a hematoxylin solution and dispensing an eosin solution to the samples, or dispensing a hematoxylin solution, dispensing an Orange-G solution and dispensing an Eosin-azure solution to the samples. In addition, the method can further include dehydrating said samples at any time, but particularly between dispensing the hematoxylin solution and dispensing the Orange-G and Eosin-azure solutions to samples.

In yet another particular embodiment, the method can further include moving the slide tray under a radiant heater prior to moving the slide tray to the first workstation and melting paraffin in the samples held under the radiant heater.

In some particular embodiments, the method can further include solvent exchanging said samples through a series of two or more different solvents or solvent mixtures in the first workstation. Solvent exchanging can include dehydrating the samples, rehydrating the samples, or both, in any order one or more times. In still other particular embodiments, the method further includes moving the slide tray to a third workstation and solvent exchanging the samples through a series of two or more different solvents or solvent mixtures in the third workstation. As before, solvent exchanging can include dehydrating the samples, rehydrating the samples, or both, in any order, one or more times.

In other embodiments, the method further includes moving the slide tray to a third or fourth workstation and drying the samples in the third or fourth workstation. In addition, the method can include heating the slide tray in the second or third workstation prior to moving the slide tray to the third or fourth workstation for drying.

In particular embodiments, the method can further include prioritizing any given slide tray, thereby completing all operations on that slide tray first. And in other particular embodiments, the method can include communicating tray status to a laboratory information system. In other particular embodiments, the biological samples include cytological samples, and in yet others, the biological samples can include tissue sections. Of course a mix of different types of biological samples can be included on a particular slide or between different slides held in a particular slide tray.

In yet another aspect, a reagent container is disclosed for containing a reagent (for example, a reagent such as a biological stain, a rinse, a de-paraffinizing fluid, a solvent or a solvent mixture) for use in an automated biological reaction apparatus such as an automated stainer, or any type of automated system for the treatment or processing of biological samples. The disclosed container includes a casing having a bottom, sidewalls and a cover, a collapsible bag compatible with a reagent to be contained therein, held within the casing, the collapsible bag including a bottom, sidewalls and a top wall configured and dimensioned to substantially fill the casing when expanded, the collapsible bag also having a tube sealed to the top wall of the bag and extending into an interior of the bag, wherein said top wall of the casing is keyed to mate with a corresponding key in said biological reaction apparatus. Typically, the collapsible bag is formed of a flexible polymer or some type of laminated material such as a three-layer laminate. Also typically, the tube is attached in some manner to the top wall of the casing, and the tube extends to or near said bottom of the bag. A sealing fitting can be attached to a distal end of the tube, for example, an elastomeric seal can be attached to the distal end of the tube. Such an elastomeric seal con include a thin material that is easily punctured by manual insertion of a piercing tube. The fitting can be fixedly located under or to the cover, and the cover and or a sidewall can include a cutout for providing access to the fitting. A removable sealing tape can be placed over the cutout, for example, to protect the fitting and its seal during shipping.

In a particular embodiment, the container can be keyed, such as with a color code or an interference fit (for example, a protrusion or shape that permits insertion of the container into one or more particular positions in a biological reaction apparatus but not into other similar positions on the same biological reaction apparatus). A barcode and/or an RFID tag can be associated with a wall of the container, for example, associated with an outer wall.

Various changes may be made without departing from the spirit and scope of the invention. For example, not all system functions need to be performed on a given tray. Thus, for example, a tray may be inserted into the apparatus for coverslipping only. Alternatively, the apparatus may include two or more de-paraffinizing/staining/solvent exchange station modules and/or two or more other modules in order to increase through-put. A feature of a particular embodiment is that additional station modules can be added vertically without increasing the footprint of the system. Other reagents may be utilized on the instrument to perform other tests, including those used for in situ hybridization (typically DNA/RNA probes), or immunohistochemistry (typically antibodies). In addition to microscope slides, tissue, DNA, RNA and protein arrays may also be accommodated with minimal or no modification of the slide trays. Yet other changes may be made in the invention without departing from the spirit and scope thereof, the scope of the invention being defined by the appended claims to be interpreted in light of the foregoing specification.

We claim:
1. An automated method for processing a plurality of slides, the method comprising:
robotically transporting a slide carrier to a stainer workstation while the slide carrier carries the plurality of slides;
staining biological samples carried by the slides by separately dispensing reagent onto individual slides of the plurality of slides via a dispense manifold, which is fluidically coupled to a first container and a second container, after robotically transporting the slide carrier to the stainer workstation, wherein separately dispensing the reagent onto the individual slides includes:
pumping a first staining solution out of the first container, through at least one line, and out the dispense manifold such that a first volume of the first staining solution is delivered onto a first one of the plurality of slides to stain a first biological sample of the biological samples,
clearing the first staining solution from the at least one line, and
pumping a second staining solution out of the second container, through the at least one line, and out the dispense manifold such that a second volume of the second staining solution is delivered onto a second one of the plurality of slides to stain a second biological sample of the biological samples; and after staining the biological samples, robotically removing the slide carrier from the stainer workstation while the slide carrier carries the plurality of slides.

2. The method of claim 1, wherein the plurality of slides includes a first slide and a second slide, wherein the first biological sample is positioned on the first slide and the second biological sample is positioned on the second slide, and wherein staining the biological samples comprises:
performing a first set of slide processing operations on the first slide, the first set of slide processing operations includes at least
depositing the first volume of the first staining solution onto an upper surface of the first slide,
maintaining contact between the first staining solution deposited onto the upper surface of the first slide and the first biological sample for a predetermined first period of time, and
performing a second set of slide processing operations on the second slide, the second set of slide processing operations includes at least
depositing the second volume of the second staining solution onto an upper surface of the second slide, and
maintaining contact between the second staining solution deposited onto the upper surface of the second slide and the second biological sample for a predetermined second period of time.

3. The method of claim 1, wherein staining the biological samples carried by the slides includes delivering reagent towards one of the slides without contacting any other slides of the plurality of slides with the delivered reagent.

4. The method of claim 1, further comprising:
flowing the first staining solution from the first container, into the dispense manifold, and out one or more nozzles of the dispense manifold.

5. The method of claim 1, wherein separately dispensing the reagent includes sequentially delivering streams of the reagent toward upper surfaces of the slides.

6. The method of claim 1, wherein separately dispensing the reagent includes:
(a) positioning a dispense manifold relative to a slide of the plurality of slides;
(b) delivering the reagent from the dispense manifold to the slide of the plurality of slides; and
(c) repeating (a) and (b) to deliver reagent onto all the slides.

7. The method of claim 1, wherein separately dispensing the reagent includes separately dispensing hematoxylin and/or eosin to each of the slides.

8. The method of claim 1, wherein staining the biological samples includes:
removing dispensed reagent from at least one slide of the plurality of slides; and
dispensing another reagent onto the at least one slide.

9. The method of claim 8, wherein removing dispensed reagent includes delivering fluid toward the at least one slide such that the fluid causes removal of the dispensed reagent.

10. The method of claim 9, wherein the fluid is air, reagent, and/or wash solution.

11. The method of claim 1, wherein staining the biological samples includes removing reagent that has been dispensed onto at least one slide of the plurality of slides by directing air and/or reagent toward the at least one slide.

12. The method of claim 11, wherein directing air and/or reagent toward the first slide includes delivering air and/or reagent out of nozzles positioned above the slide carrier.

13. The method of claim 1, wherein robotically transporting the slide carrier to the stainer workstation includes moving the slide carrier into a chamber of the stainer workstation using a transporter mechanism.

14. The method of claim 1, wherein the slide carrier is a slide tray that holds the slides at substantially horizontal orientations.

15. The method of claim 1, wherein after robotically removing the slide carrier from the stainer workstation, the method further comprises:
transporting the slide carrier to an automated coverslipper workstation while the slide carrier carries the plurality of slides; and
coverslipping each individual slide of the plurality of slides with a respective coverslip using the automated coverslipper workstation while the individual slides are held in spatially co-planar, substantially horizontal positions in the slide carrier such that the coverslips on the slides are spaced apart from one another.

16. The method of claim 1, further comprising pumping reagents that have been dispensed by the stainer workstation out of the stainer workstation.

17. An automated method for processing a plurality of slides individually bearing biological samples, comprising:
transporting a slide carrier to a stainer workstation using a transporter mechanism while the slide carrier holds the plurality of slides in a spaced apart horizontal arrangement;
after transporting the slide carrier to the stainer workstation, separately delivering reagent onto each individual slide of the plurality of slides held by the slide carrier such that a substantial amount of the reagent applied to one slide of the plurality of slides does not contact any other slides of the plurality of slides, wherein separately delivering the reagent onto each individual slide includes
pumping staining solutions from containers located outside of the stainer workstation into the stainer workstation, through a movable dispense manifold within the stainer workstation, and out of the movable dispense manifold; and
after separately delivering the reagent onto the individual slides, removing the slide carrier from the stainer workstation.

18. The method of claim 17, wherein separately delivering the reagent onto the slides includes directing reagent streams of reagent toward respective slides.

19. The method of claim 18, wherein
the plurality of slides includes a first slide and a second slide, and
directing reagent streams of reagent toward the respective slides includes:
directing a first reagent stream toward the first slide; and
directing a second reagent stream toward the second slide.

20. The method of claim 17, wherein separately delivering the reagent onto the slides includes flowing the staining solutions from at least one of the containers, through a fluidics module, and out at least one dispense nozzle positioned above the slide carrier.

21. The method of claim 17, further comprising:
performing a first stain protocol on a first slide of the plurality of slides; and
performing a second stain protocol on a second slide of the plurality of slides, wherein the first stain protocol is different from the second stain protocol.

22. The method of claim 17, wherein separately delivering the reagent includes delivering hematoxylin and/or eosin onto two or more of the slides.

23. The method of claim 17, wherein the slide carrier is a slide tray that holds the slides at substantially horizontal orientations.

24. The method of claim 17, further comprising:
after delivering the reagent onto a first slide of the plurality of slides, removing the reagent from the first slide, and
after removing the reagent from the first slide, dispensing another reagent onto the first slide.

25. The method of claim 17, wherein separately delivering the reagent onto the individual slides includes delivering a first reagent onto a first slide of the plurality of slides, and the method further comprises:
removing at least a portion of the first reagent from the first slide; and
delivering a second reagent onto the first slide.

26. The method of claim 25, wherein delivering the second reagent onto the first slide includes dispensing hematoxylin and/or eosin onto the first slide.

27. The method of claim 17, wherein separately delivering the reagent onto the individual slides includes delivering a first reagent onto a first slide of the plurality of slides, and the method further comprises:
after delivering the first reagent onto the first slide, delivering a second reagent onto the first slide.

28. The method of claim 27, further comprising removing at least a portion of the first reagent prior to delivering the second reagent.

29. The method of claim 17, wherein the dispense manifold is fluidically coupled to a first container located outside of the stainer workstation and the dispense manifold is fluidically coupled to a second container located outside of the stainer workstation, and wherein the method further comprises:
pumping a first stain solution out of the first container, through at least one fluid line of a fluidics module, and through the dispense manifold such that the stainer workstation dispenses the first stain solution onto a first one of the plurality of slides; and
pumping a second stain solution out of the second container, through the fluidics module, and through the dispense manifold such that the dispense manifold dispenses the second stain solution onto a second one of the plurality of slides.

30. The method of claim 17, further comprising
pumping reagents, which have been dispensed by the stainer workstation, away from the slide carrier positioned within the stainer workstation; and
delivering the reagents out of the stainer workstation.

31. The method of claim 17, wherein the plurality of slides includes a first slide and a second slide, wherein a first biological sample is positioned on the first slide and a second biological sample is positioned on the second slide, and wherein the method further comprises:
dispensing reagent out of an array of spaced apart dispense nozzles of the dispense manifold to deliver the reagent toward different locations along the first slide; and
dispensing reagent out of the array of spaced apart dispense nozzles of the dispense manifold to deliver the reagent toward different locations along the second slide.

32. An automated method for processing a plurality of slides, the method comprising:
robotically transporting a slide carrier into a stainer workstation while the slide carrier carries the plurality of slides;
separately dispensing staining solutions onto individual slides of the plurality of slides by pumping staining solutions from containers located outside of the stainer workstation into the stainer workstation, through a movable dispense manifold within the stainer workstation, and out of the movable dispense manifold;
delivering staining solution, which has been dispensed by the movable dispense manifold, out of the stainer workstation; and
robotically removing the slide carrier from the stainer workstation.

33. The method of claim 32, further comprising:
combining the staining solutions from the containers using a mixing manifold in fluid communication with the containers to produce the staining solutions that are delivered onto the individual slides, and
wherein the containers include
a first container containing hematoxylin solution,
a second container containing eosin solution, and
a third container containing a solvent.

34. The method of claim 32, wherein the containers include a first container and a second container, the method further comprising:
pumping a first staining solution out of the first container, through at least one line, and out the dispense manifold such that the first staining solution is delivered onto a first one of the plurality of slides to stain a first biological sample;
clearing the first staining solution from the at least one line;
pumping a second staining solution out of the second container, through the at least one line, and out the dispense manifold such that the second staining solution is delivered onto a second one of the plurality of slides to stain a second biological sample; and
delivering the first staining solution and/or the second staining solution, which has been delivered out of the dispense manifold, out of the stainer workstation.

35. The method of claim 32, wherein the staining solutions include a hematoxylin solution and an eosin solution, and wherein all of the staining solutions dispensed onto the plurality of slides are pumped from the containers and through fluid lines in fluid communication with the dispense manifold.

36. The method of claim 32, wherein the staining solutions include hematoxylin solution and eosin solution, the method further comprising delivering the hematoxylin solution and the eosin solution onto each of the plurality of slides.

* * * * *